United States Patent
Amaravadi et al.

(10) Patent No.: US 10,774,047 B2
(45) Date of Patent: Sep. 15, 2020

(54) DIMERIC QUINACRINE DERIVATIVES AS AUTOPHAGY INHIBITORS FOR CANCER THERAPY

(71) Applicant: THE TRUSTEES OF THE UNIVERSITY OF PENNSYLVANIA, Philadelphia, PA (US)

(72) Inventors: Ravi K. Amaravadi, Media, PA (US); Jeffrey Winkler, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 127 days.

(21) Appl. No.: 15/567,187

(22) PCT Filed: Apr. 26, 2016

(86) PCT No.: PCT/US2016/027920
§ 371 (c)(1),
(2) Date: Oct. 17, 2017

(87) PCT Pub. No.: WO2016/168721
PCT Pub. Date: Oct. 20, 2016

(65) Prior Publication Data
US 2018/0111904 A1    Apr. 26, 2018

Related U.S. Application Data

(60) Provisional application No. 62/148,804, filed on Apr. 17, 2015.

(51) Int. Cl.
| | |
|---|---|
| *C07D 219/12* | (2006.01) |
| *A61K 31/473* | (2006.01) |
| *A61K 45/06* | (2006.01) |
| *A61K 31/7068* | (2006.01) |
| *A61P 37/00* | (2006.01) |
| *A61P 17/00* | (2006.01) |
| *A61P 19/02* | (2006.01) |
| *A61P 33/06* | (2006.01) |
| *A61P 35/04* | (2006.01) |
| *A61P 35/00* | (2006.01) |

(52) U.S. Cl.
CPC .......... *C07D 219/12* (2013.01); *A61K 31/473* (2013.01); *A61K 31/7068* (2013.01); *A61K 45/06* (2013.01); *A61P 17/00* (2018.01); *A61P 19/02* (2018.01); *A61P 33/06* (2018.01); *A61P 35/00* (2018.01); *A61P 35/04* (2018.01); *A61P 37/00* (2018.01); *Y02A 50/411* (2018.01)

(58) Field of Classification Search
None
See application file for complete search history.

(56) References Cited

U.S. PATENT DOCUMENTS

| | | |
|---|---|---|
| 5,886,185 A | 3/1999 | Chou et al. |
| 2004/0229898 A1 | 11/2004 | Prusiner et al. |
| 2014/0050696 A1 | 2/2014 | Amaravadi |
| 2016/0168099 A1 | 6/2016 | Amaravadi et al. |
| 2017/0166530 A1 | 6/2017 | Amaravadi et al. |
| 2017/0275252 A1 | 9/2017 | Amaravadi et al. |

FOREIGN PATENT DOCUMENTS

| | | | |
|---|---|---|---|
| SU | 52430 A1 * | 1/1938 | ........... C07D 219/12 |
| WO | 2012149186 A2 | 11/2012 | |
| WO | 2016022956 A2 | 2/2016 | |

OTHER PUBLICATIONS

Gerchuck et al., CAS SciFinder English language (database CAPLUS Acc No. 1940:24321) abstract of RU 52430 (Jan. 31, 1938).*
Caffrey et al., Antimicrobial Agents and Chemotherapy (2007), 51(6), pp. 2164-2172.*
Lum JJ, et al. Autophagy in metazoans: cell survival in the land of plenty. Nat Rev Mol Cell Biol, 2005;6: 439-448.
Amaravadi RK, Thompson CB. The roles of therapy-induced autophagy and necrosis in cancer treatment. Clin Cancer Res, 2007;13: 7271-7279.
Amaravadi RK, et al. Autophagy inhibition enhances therapy-induced apoptosis in a Myc-induced model of lymphoma. J Clin Invest, 2007;117: 326-336.
Degenhardt K, et al. Autophagy promotes tumor cell survival and restricts necrosis, inflammation, and tumorigenesis. Cancer Cell, 2006;10: 51-64.
Amaravadi RK Autophagy-induced tumor dormancy in ovarian cancer. J Clin Invest., 2008;118(12):3837-3841.
Carew JS, et al. Targeting autophagy augments the anticancer activity of the histone deacetylase inhibitor SAHA to overcome Bcr-Abl-mediated drug resistance. Blood. 2007;110:313-322.
Degtyarev M, et al. Akt inhibition promotes autophagy and sensitizes PTEN-null tumors to lysosomotropic agents. J Dell Biol, 2008;183: 101-116.
Sotelo J, et al. Adding chloroquine to conventional treatment for glioblastoma multiforme: a randomized, double-blind, placebo-controlled trial. Ann Intern Med, 2006;144: 337-343.
Amaravadi RK, et al. et al. Principles and Current Strategies for Targeting Autophagy for Cancer Treatment. Clin Cancer Res, 2011;17: 654-666.
Rebecca VW, et al. Inhibition of autophagy enhances the effects of the AKT inhibitor MK-2206 when combined with paclitaxel and carboplatin in BRAF wild-type melanoma. Pigment Cell Melanoma Res, 2014;27: 465-478.
Mahalingam D, et al. Combined autophagy and HDAC inhibition: A phase I safety, tolerability, pharmacokinetic, and pharmacodynamic analysis of hydroxychloroquine in combination with the HDAC inhibitor vorinostat in patients with advanced solid tumors. Autophagy, 2014;10.1403-1414.

(Continued)

*Primary Examiner* — Brian J Davis
(74) *Attorney, Agent, or Firm* — BakerHostetler

(57) ABSTRACT

The invention provides dimeric quinacrine derivatives and related compounds and compositions, methods of treatment and syntheses. The novel compounds exhibit unexpected anticancer activity and are useful in the treatment of a variety of autophagy-related disorders.

4 Claims, 31 Drawing Sheets

(56) References Cited

OTHER PUBLICATIONS

Rangwala R, et al. Combined MTOR and autophagy inhibition: Phase I trial of hydroxychloroquine and temsirolimus in patients with advanced solid tumors and melanoma. Autophagy, 2014;10:1391-1402.
Rangwala R, et al. Phase I trial of hydroxychloroquine with dose-intense temozolomide in patients with advanced solid tumors and melanoma. Autophagy, 2014;10.1369-1379.
Rosenfeld MR, et al. A phase I/II trial of hydroxychloroquine in conjunction with radiation therapy and concurrent and adjuvant temozolomide in patients with newly diagnosed glioblastoma multiforme. Autophagy, 2014;10.1359-1368.
Vance D, et al. Polyvalency: a promising strategy for drug design. Biotechnol Bioeng, 2008;101: 429-434.
Shrivastava A, et al. Designer peptides: learning from nature. Curr Pharm Des, 2009;15: 675-681.
Girault S. et al. Antiplasmodial activity and cytotoxicity of bis-, tris-, and tetraquinolines with linear or cyclic amino linkers. J Med Chem, 2001;44: 1658-1665.
Vennerstrom JL, et al. Bisquinolines. 2. Antimalarial N,N-bis(7-chloroquinolin-4-yl)heteroalkanediamines. J Med Chem, 1998;41: 4360-4364.
Burnett JC, et al. Novel small molecule inhibitors ofbotulinum neurotoxin A metalloprotease activity. Biochem Biophys Res Commun, 2003;310: 84-93.
Aits S, et al. Sensitive detection of lysosomal membrane permeabilization by lysosomal galectin puncta assay. Autophagy, 2015;11:1408-1424.
Bar-Peled L, et al. Ragulator is a GEF for the rag GTPases that signal amino acid levels to mTORC1. Cell, 2012;150:1196-1208.
Carroll B, et al.Control of TSC2-Rheb signaling axis by arginine regulates mTORC1 activity. eLife, 2016;5:e11058.
Efeyan A, et al. Amino acids and mTORC1: from lysosomes to disease. Trends Mol Med, 2012;18:524-533.
Egan DF, et al. Small Molecule Inhibition of the Autophagy Kinase ULK1 and Identification of ULK1 Substrates. Mol cell, 2015;59:285-297.
Eng CH, et al. Macroautophagy is dispensable for growth of KRAS mutant tumors and chloroquine efficacy. Proc Natl Acad Sci, 2016;113:182-187.
Honda A, et al. Potent, Selective, and Orally Bioavailable Inhibitors of VPS34 Provide Chemis Tools to Modulate Autophagy in Vivo. ACS medicinal chemistry letters, 2016;7:72-76.
Inoki K, et al. TSC2 integrates Wnt and energy signals via a coordinated phosphorylation by AMPK and GSK3 to regulate cell growth. Cell, 2006;126:955-968.
Jennings BR, Ridler PJ. Interaction of chromosomal stains with DNA. An electrofluorescence study. Biophysics of structure and mechanism, 1983;10:71-79.
Jiang X, et al. Autophagy in cellular metabolism and cancer. J Clin Invest, 2015;125:47-54.
Kim DH, et al. mTOR interacts with raptor ro form a nutrient-sensitive complex that signals to the cell growth machinery. Cell, 2002;110:163-175.
Kim J, et al. AMPK and mTOR regulate autophagy through direct phosphorylation of Ulk1. Nature cell biology, 2011;13:132-141.
Klionsky DJ, Zuckerbraun B. Guidelines for the use and interpretation of assays for monitoring autophagy. Autophagy, 2012;8:445-544.
Korfel A, et al. Phase II Trial of Temsirolimus for Relapsed/Refractory Primary CNS Lymphoma. J Clin Oncol, 2016;34(15):1757-1763.
Liu J, et al. Beclin1 controls the levels of p53 by regulating the deubiquitination activity of USP10 and USP13. Cell, 2011;147:223-234.

McAfee Q, et al. Autophagy inhibitor Lys05 has single-agent antitumor activity and reproduces the phenotype of a genetic autophagy deficiency. Proc Natl Acad Aci USA, 2012;109:8253-8258.
O'Reilly KE, et al. Phosphorylated 4E-BP1 is associated with poor survival in melanoma. Clinical cancer research: an official journal of the American Association for Cancer Research, 2009:15:2872-2878.
Perera RM, et al.Transcriptional control of autophagy-lysosome function drives pancreatic cancer metabolism. Nature, 2015;524:361-365.
Rangwala R, et al. Combined MTOR and autophagy inhibition: phase I trial of hydroxychloroquine and temsirolimus in patients with advanced solid tumors and melanoma. Autophagy, 2014:141:290-303.
Sancak Y, et al. Ragulator-Rag complex targets mTORC1 to the lysosomal surface and is necessary for its activation by amino acids. Cell, 2010;141:290-303.
Twyman-Saint Victor C, et al. Radiation and dual checkpoint blockade activate non-redundant immune mechanisms in cancer. Nature, 2015;520:373-377.
Vogl DT, et al. Combined autophagy and proteasome inhibition: a phase 1 trial of hydroxychloroquine and bortezomib in patients with relapsed/refractory myeloma. Autophagy, 2014;10:1380-1390.
Wolpin BM, et al. Phase II and pharmacodynamics study of autophagy inhibition using hydroxychloroquine in patients with metastatic pancreatic adenocarcinoma. The oncologist, 2014;19:637-638.
Yang A, et al. Autophagy is critical pancreatic tumor growth and progression in tumors with p53 alterations. Cancer Discov, 2014;4:905-913.
Anderson MO, et al. Parallel synthesis of 9-aminoacridines and their evaluation against chloroquine-resistant Plasmodium falciparum. Bioorganic & Medicinal Chemistry, 2006;14:334-343.
Girault, Sophie et al.; Antimalarial, antitrypanosomal, and antileishmanial activities and cytotoxicity of Bis(9-amino-6-chloro-2-methoxyacridines): Influence of the Linker; J. Med. Chem., 2000, vol. 43, pp. 2646-2654.
Wang, S.-S. et al.; Linker-modified triamine-linked acridine dimers: Synthyesis and cytotoxicity properties in vitro and in vivo; Bioorganic & Medicinal Chemistry (2007); vol. 15, pp. 735-748.
Moisan, M. et al.; New alpha, omega-Diamino Mono-and Bi-Bridged Acridine Dimers; Monatshefte Fur Chemie (1993); vol. 124, pp. 23-35.
Hansen, J.B. et al.; 9-Acridinyl and @-Methoxy-6-chloro-9-acridinyl Derivatives of Aliphatic Di-, Tri-, and Tetraamines. Chemistry, Cytostatic Activity, and Schistosomicidal Activity; Journal of Medicinal Chemistry (1983); vol. 26, pp. 1510-1514.
Atwell, G.J. et al.; Potential Antitumor Agents: 45. Synthesis, DNA-Binding Interaction, and Biological Activity of Triacridine Derivatives; Journal of Medicinal Chemistry (1986); vol. 29, pp. 69-74.
Wright, R.G., McR. et al.; Effects of Ring Substituents and Linker Chains on the Bifunctional Intercalation of Diacridines into Deoxyribonucleic Acid; Biochemistry (1980); vol. 19, pp. 5825-5836.
Ackerman, N. B. et al.; Preparation and Screening of Aminoacridines for Induction of Lung Tumor Fluorescence in Rats; Journal of Medicinal Chemistry (1968); vol. 11, nr. 12, pp. 315-321.
Monge et al.; Synthesis and Preliminary Cytotoxic Activity of Dimethoxy-acridines and Dimethoxy-nitroacridines; Journal of Heterocyclic Chemistry (1994); vol. 31, pp. 1455-1460.
Denny, W.A. et al.; Potential Antitumour Agents. 44. Synthesis and Antitumour Activity of New Classes of Diacridines. Importance of Linkier Chain Rigidity for DNA Binding Kinetics and Biological Activity; Journal of Medicinal Chemistry (1985); vol. 28, nr. 11, pp. 1568-1574.
Bailey GS et al.; Carcinogenic aflatoxin B1 is located preferentially in internucleosomal deoxyribonucleic acid following exposure in vivo in rainbow trout.; Biochemistry (1980); vol. 19, pp. 5836-5842.

* cited by examiner

A

6-Methoxyquinaldine          Quinacrine

Meflaquine          Primaquine

DIMERIC QUINACRINE DERIVATIVES AS AUTOPHAGY INHIBITORS FOR CANCER THERAPY

This application is a United States national phase patent application based upon international patent application number PCT/US2016/027920 of international filing date Apr. 26, 2016, which claims the benefit of priority of United States provisional application number U.S. 62/148,804, filed 17 Apr. 2015, of identical title, the entire contents of which two applications is incorporated by reference herein.

CLAIM OF PRIORITY AND GOVERNMENT INTEREST

The invention was made with government support under Grant Number P01-CA114046 awarded by the National Institutes of Health. The government has certain rights in the invention.

FIELD OF THE INVENTION

The invention provides dimeric quinacrine and related compounds, methods of treatment and syntheses. The novel compounds exhibit unexpected anticancer activity and are useful in the treatment of a variety of autophagy-related disorders.

BACKGROUND OF THE INVENTION

Autophagy consists of the sequestration of organelles and proteins in autophagic vesicles (AV) and degradation of this cargo through lysosomal fusion [1]. Autophagy allows tumor cells to survive metabolic and therapeutic stresses [2-5]. Multiple publications indicate therapy-induced autophagy is a key resistance mechanism to many anticancer agents. Chloroquine (CQ) (Compound 1, FIG. 1) derivatives block autophagy by inhibiting the lysosome [3,6,7]. Based on these findings, clinical trials combining cancer therapies with hydroxychloroquine (HCQ; FIG. 1 Compound 2), (which is safer than CQ to dose escalate) have been launched. Preliminary results indicate these combinations have activity [9-14], but it is still unclear if this activity is consistently due to the addition of HCQ. High micromolar concentrations of HCQ are required to inhibit autophagy.

While there is some pharmacodynamic evidence of autophagy inhibition with HCQ in cancer patients, it is inconsistent because adequate concentrations are not achieved in all patients. There is an unmet need to develop more potent inhibitors of autophagy. The design and synthesis of dimeric analogs of CQ, that exploit the thermodynamic advantages imparted by polyvalency [15,16], has been a subject of intensive study for over 10 years [17-19]. An early report by Vennerstrom[18] described the synthesis of heteroalkane-bridged bisquinolines as potential antimalarials, but none of the compounds had sufficient antimalarial activity to warrant further investigation. Subsequently, Sergheraert [17] reported that tetraquinolines, i.e., dimers of bisquinolines, afforded potent antimalarials, confirming the possibility that the application of the polyvalency strategy could afford increased potency, at least with respect to antimalarial activity. More recently, Lee[20] has described the potentiation of AKT inhibitors by fluorinated quinoline analogs. Solomon[21] has reported the preparation of "repositioned" chloroquine dimers, based on the use of a piperazine connector. These results suggest that these chloroquine analogs could serve as bases for the development of a new group of effective cancer chemotherapeutics.

We have examined the application of the strategy of polyvalency [15,16] to the synthesis of novel autophagy inhibitors by preparing a dimeric chloroquine from commercially available materials. We have recently reported a series of bis-4-aminoquinoline autophagy inhibitors (BAIs) that potently inhibit autophagy and impair tumor growth in vivo[22]. The structural motifs that are necessary for improved autophagy inhibition compared to CQ include the presence of two aminoquinoline rings and a triamine linker.

The multi-protein serine/threonine kinase mTORC1 (mammalian target of rapamycin complex 1) is a master regulator of catabolism and anabolism (Kim et al., 2002). For full activation, mTORC1 requires amino acid/Rag GTPase/Ragulator-dependent lysosomal localization to be in close proximity of Rheb (Ras homologue enriched in brain). The pentameric Ragulator protein complex (p18, p14, MP1, HBXIP, c7orf59) resides on the lysosomal surface and serves as a docking site for Rag GTPases when amino acids are present, which in turn directly interact with the raptor component of mTORC1, resulting in the lysosomal recruitment of mTORC1 (Bar-Peled et al., 2012; Sancak et al., 2010). Once on the lysosomal surface mTORC1 is fully activated by Rheb, which also resides on the cytoplasmic surface of the lysosome (Carroll et al., 2016). Rheb, the master activator of mTORC1, is negatively regulated by the tuberous sclerosis complex 1 (TSC1), TSC2 and TBC1D7 proteins. Environmental signals and intracellular conditions, including growth factor (GF) and amino acid (AA) availability, converge on TSC2, which in turn exerts its GTPase-activating protein (GAP) activity towards Rheb, shifting Rheb from its active GTP-bound state to its inactive GDP-bound conformation when GF/nutrient levels are low (Inoki et al., 2006). Therefore with the lysosomal residence of the Rag GTPases and Rheb, considered the two most proximal regulators of mTORC1, the lysosomal surface represents a critical signaling pivot where global cellular health information is integrated and translated into the activation status of mTORC1.

Lysosomal fusion and subsequent degradation of cargo-filled autophagic vesicles (AVs) allows for intracellular replenishment of nutrients, including AAs, sugars and nucleic acids (Jiang et al., 2015). Autophagy, an evolutionarily conserved homeostatic mechanism that allows cells to mitigate metabolic stresses of anabolism and catabolism, is directly regulated by mTORC1 via inhibitory phosphorylation of Unc-51-like kinase 1 (ULK1) at its serine-757 residue (Kim et al., 2011). When cellular health is compromised such as in the case of low AA levels, mTORC1 is inactivated due to its inability to be recruited by Rag GTPases to the lysosome, resulting in the initiation of autophagy, which recycles misfolded proteins into AA building blocks to restore cellular homeostasis. Aberrant autophagic-lysosomal activity and dysregulated mTORC1 signaling each have been demonstrated to allow tumor cells to resist therapeutic stresses of chemotherapy and targeted therapy, however attempts to clinically address these intertwined pro-tumorigenic mechanisms independently have had few durable responses with either PI3K/AKT/mTORC1-pathway targeted or autophagy-lysosome targeted monotherapy (Korfel et al., 2016; Wolpin et al., 2014). The combination of PI3K/AKT/mTORC1-pathway targeted agents with HCQ has been performed clinically with encouraging safety, tolerability and activity (Rangwala et al., 2014). However, pharmacokinetic (PK)-pharmacodynamic (PD) studies performed in patients receiving HCQ as cancer therapy have reported evidence of autophagy inhibition only in patients treated with the highest concentrations of HCQ that are inconsistently achieved in humans (Vogl et al., 2014). Therefore, there is an unmet need to develop more potent lysosomal inhibitors that can simultaneously influence autophagy and mTORC1 activity. Here we report the synthesis of a dimeric quinacrine (DQ) analog DQ661 that concurrently inhibits autophagy and mTORC1 by way of lysosome membrane permeabilization (LMP) and displacement of mTORC1 from the lysosomal compartment through disruption of Rag/Ragulator/lysosome interactions. This work identifies a novel pharmacological strategy to inhibit mTORC1 with in vivo activity in melanoma xenograft and pancreatic syngeneic mouse models.

SUMMARY OF THE INVENTION

The inventors demonstrate the preparation and the unexpected biological activity of dimeric quinacrine derivatives as set forth herein.

The present invention relates to compounds of the general chemical formula I:

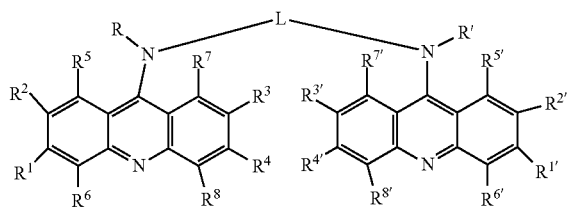

wherein $R^1$, $R^2$, $R^3$, $R^4$, $R^5$, $R^6$, $R^7$, $R^8$, $R^{1'}$, $R^{2'}$, $R^{3'}$, $R^{4'}$, $R^{5'}$, $R^{6'}$, $R^{7'}$ and $R^{8'}$ are each independently H, halogen (F, Cl, Br or I) CN, $NO_2$, OH, COOH, an optionally substituted $C_1$-$C_6$ alkyl (when substituted, preferably substituted with 1 or 2 hydroxyl groups or 3-5 fluoro groups, preferably a $CF_3$ group), optionally substituted O—$C_1$-$C_6$ alkyl (preferably $OCH_3$), optionally substituted $C_1$-$C_7$ preferably $C_2$-$C_7$ acyl (preferably acetyl), $NR_AR_B$ where $R_A$ and $R_B$ are each independently H, an optionally substituted $C_1$-$C_6$ alky or an optionally substituted $C_1$-$C_7$ acyl group, (thus forming an amide or diamide group), an optionally substituted $C_2$-$C_7$ ester (oxycarbonyl ester or carboxyester, preferably carboxyester), —$SO_2NR_AR_B$, where $R_A$ and $R_B$ are the same as above, —$SO_3R^S$ or $SO_4R^S$, where $R^S$ is H or an optionally substituted $C_1$-$C_6$ alkyl;

R and R' are each independently H, a $C_1$-$C_6$ optionally substituted alkyl group, a $C_1$-$C_7$ (preferably $C_2$-$C_7$) optionally substituted acyl group, a $C_2$-$C_7$ optionally substituted carboxy ester group (which forms a urethane group with the nitrogen atom to which R or R' is bonded);

L is a linker group which covalently links the two exocyclic amine groups at the 9 position of the acridine moiety to each other as otherwise described herein, and preferably is a $-(CH_2Y)_n-X-(Y'CH_2)_n-$ group or a A-$(CH_2-CH_2-Z)_n$-A' group (either A or A' may be bonded to either of the two amine groups in compound I) wherein at least one of the $CH_2$ groups in L is optionally substituted, preferably with a $C_1$-$C_3$ alkyl group which itself is optionally substituted, preferably with one or two hydroxyl groups;

X is absent, $(CH_2)_j$, O, S or N—R";

Y is absent, $CH_2$, O, $CH_2O$ or N—R" and Y' is absent $CH_2$, O, $OCH_2$ or N—R", with the proviso that when one or more of X, Y and Y' is present, each of X and Y, X and Y' or Y and Y', when present, forms a stable bond;

R" is H, an optionally substituted $C_1$-$C_{12}$ alkyl group, Cy' or (C=O)$_z$-G, where Cy' is an optionally substituted cycloalkyl, aryl or heteroaryl group, G is H or an optionally substituted $C_1$-$C_{12}$ (preferably $C_1$-$C_8$, often $C_1$-$C_3$ alkyl) alkyl, alkene or alkynyl group (wherein optional substituents include a $C_1$-$C_{12}$ (preferably $C_1$-$C_8$) alkyl, alkene or alkynyl group substituted by (N—$R^J$)—($C_1$-$C_8$ alkyl, alkene or alkynyl group)$_z$-(Cy$^2$)$_x$, where $R^J$ is H or a $C_1$-$C_8$ alkyl, alkene or alkynyl group, z is 0, 1, 2, 3, 4 or 5, x is 0 or 1 and Cy$^2$ is an optionally substituted aryl or heteroaryl group (most preferably benzyl, quinolinyl, especially 4-aminoquinolinyl or acridinyl, especially 9-aminoacridinyl);

j is 1, 2, 3, 4 or 5 (preferably 1 or 2);

Each n is independently an integer between 0-20, preferably 1-15, often 0, 1, 2, 3, 4, 5, 6, 7, 8, 9 or 10 with the proviso that when n is 0, X is $(CH_2)_j$ where j is at least 1 and at least one $CH_2$ group is optionally substituted, preferably with a $C_1$-$C_3$ alkyl group which itself is optionally substituted with one or two hydroxyl groups;

A is absent or $(CH_2)_j$ and A' is $(CH_2)_j$ wherein at least one $CH_2$ group in A or A' is optionally substituted, preferably with a $C_1$-$C_3$ alkyl group which is itself optionally substituted with one or two hydroxyl groups;

Z is O or N—$R^Z$;

$R^Z$ is H or an optionally substituted $C_1$-$C_3$ alkyl group, or a pharmaceutically acceptable salt, enantiomer, diastereomer, solvent or polymorph thereof.

In s preferred embodiment, the invention provides a compound of Formula IA:

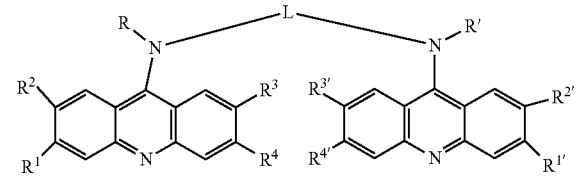

IA wherein $R^1$, $R^2$, $R^3$, $R^4$, $R^{1'}$, $R^{2'}$, $R^{3'}$ and $R^{4'}$ are each independently H, halogen (F, Cl, Br or I) CN, $NO_2$, OH, COOH, an optionally substituted $C_1$-$C_6$ alkyl (when substituted, preferably substituted with 1 or 2 hydroxyl groups or 3-5 fluoro groups, preferably a $CF_3$ group), optionally substituted O—$C_1$-$C_6$ alkyl (preferably $OCH_3$), optionally substituted $C_1$-$C_7$ preferably $C_2$-$C_7$ acyl (preferably acetyl), $NR_AR_B$ where $R_A$ and $R_B$ are independently H or an optionally substituted $C_1$-$C_6$ alky group, —(NH)—$C_1$-$C_7$ acyl (forming an amide group), optionally substituted $C_2$-$C_7$ ester (oxycarbonyl ester or carboxyester, preferably carboxyester), —$SO_2NR_AR_B$, where $R_A$ and $R_B$ are the same as above, —$SO_3R^S$ or $SO_4R^S$, where $R^S$ is H or an optionally substituted $C_1$-$C_6$ alkyl;

R and R' are each independently H, a $C_1$-$C_6$ optionally substituted alkyl group, a $C_1$-$C_7$ (preferably $C_2$-$C_7$) optionally substituted acyl group, a $C_2$-$C_7$ optionally substituted carboxy ester group (which forms a urethane group with the nitrogen atom to which R or R' is bonded);

L is a linker group which covalently links the two exocyclic amine groups at the 9 position of the acridine moiety to each other as otherwise described herein, preferably L is a $-(CH_2Y)_n-X-(Y'CH_2)_n-$ group or a A-$(CH_2-CH_2-Z)_n$-A' group (either A or A' may be bonded to either of the two amine groups in compound I) wherein at least one of the $CH_2$ groups in L is optionally substituted with a $C_1$-$C_3$ alkyl group which itself is optionally substituted with one or two hydroxyl groups;

X is absent, $(CH_2)_j$ O, S or N—R";

Y is absent, $CH_2$, O, $CH_2O$ or N—R" and Y' is absent $CH_2$, O, $OCH_2$ or N—R", with the proviso that when one or more of X, Y and Y' is present, each of X and Y, X and Y' or Y and Y', when present, forms a stable bond;

R" is H, an optionally substituted $C_1$-$C_{12}$ alkyl group, $Cy^1$ or $(C=O)_z$-G, where $Cy^1$ is an optionally substituted cycloalkyl, aryl or heteroaryl group, G is H or an optionally substituted $C_1$-$C_{12}$ (preferably $C_1$-$C_8$, often $C_1$-$C_3$ alkyl) alkyl, alkene or alkynyl group (wherein optional substituents include a $C_1$-$C_{12}$ (preferably $C_1$-$C_8$) alkyl, alkene or alkynyl group substituted by $(N-R^J)$—$(C_1$-$C_8$ alkyl, alkene or alkynyl group$)_z$-$(Cy^2)_x$, where $R^J$ is H or a $C_1$-$C_8$ alkyl, alkene or alkynyl group, z is 0, 1, 2, 3, 4 or 5, x is 0 or 1 and $Cy^2$ is an optionally substituted aryl or heteroaryl group (most preferably benzyl, quinolinyl, especially 4-aminoquinolinyl, acridinyl, especially 9-aminoacridinyl);

j is 1, 2, 3, 4 or 5 (preferably 1 or 2);

Each n is independently an integer between 0-20, preferably 1-15, often 0, 1, 2, 3, 4, 5, 6, 7, 8, 9 or 10 with the proviso that when n is 0, X is $(CH_2)_j$ where j is at least 1 and at least one $CH_2$ group is optionally substituted with a $C_1$-$C_3$ alkyl group which itself is optionally substituted with one or two hydroxyl groups;

A is absent or $(CH_2)_j$ and A' is $(CH_2)_j$ wherein at least one $CH_2$ group in A or A' is optionally substituted with a $C_1$-$C_3$ alkyl group which is itself optionally substituted with one or two hydroxyl groups;

Z is O or N—$R^Z$;

$R^Z$ is H or an optionally substituted $C_1$-$C_3$ alkyl group, or a pharmaceutically acceptable salt, enantiomer, diastereomer, solvent or polymorph thereof.

In preferred aspects of the invention, $R^1$ and $R^{1'}$ are each independently H, a halo group, a nitro group or a trifluoromethyl group, preferably a chloro group. R and R' are preferably each independently H, a $C_1$-$C_3$ optionally substituted alkyl group itself preferably substituted with at least one hydroxyl group, an alkoxy group, an amine, monoalkyl amine or dialkyl amine group, wherein said amine group or said monoalkyl amine group is optionally substituted on the amine position with one or two 7-substituted-4-quinolinyl group(s) wherein the amine binds to the 4-position of the quinolinyl group and the 7-position of each quinolinyl group is optionally substituted, preferably with a $R^1$ and/or $R^{1'}$ group as broadly described for generic structure I above, or one or both alkyl groups of said monoalkyl amine or dialkyl amine is itself further optionally substituted with at least one hydroxyl group, an alkoxy group, an amine, a monoalkyl amine or a dialkyl amine wherein the amine or monoalkyl amine is optionally substituted on the amine position with one or two 7-substituted-quinolinyl group(s) wherein the amine binds to the 4-position of the quinolinyl group and the 7-position of each quinolinyl group is optionally substituted, preferably with $R^1$ and/or $R^{1'}$ as broadly described for generic structure I above, and each of said alkoxy groups (e.g. methoxy or ethoxy) is optionally further substituted with an alkoxy group, preferably a methoxy group, thus forming a diether substituent.

In certain aspects of the invention L is a $-(CH_2Y)_n-$X$-(Y'CH_2)_n-$ group, where X is N—R", Y and Y' are each independently absent or $CH_2$, (when Y or Y' is absent n is preferably at least 2) and R" is H or a $C_1$-$C_3$ alkyl group which is optionally substituted with at least one hydroxyl group, an alkoxy group, an amine, monoalkyl amine or dialkyl amine group, wherein said amine group or said monoalkyl amine group is optionally substituted on the amine position with one or two 7-substituted-4-quinolinyl group or 9-aminoacridinyl group wherein the amine binds to the 4-position of the quinolinyl group or the 9-position of the acridinyl group and the 7-position of each quinolinyl group or 9-amino acridinyl group is optionally substituted, or one or both alkyl groups of said monoalkyl amine or dialkyl amine is itself further optionally substituted with at least one hydroxyl group, an alkoxy group, an amine, a monoalkyl amine or a dialkyl amine wherein the amine or monoalkyl amine is optionally substituted on the amine position with one or two 7-substituted-quinolinyl group(s) or 9-aminoacridinyl groups, wherein the amine binds to the 4-position of the quinolinyl group or the 9-position of the acridinyl group and the 7-position of each quinolinyl group or the 9-aminoacridinyl group is optionally substituted, preferably with $R^1$ and/or $R^{1'}$ as broadly described for generic structure I above, and each of said alkoxy groups (e.g. methoxy or ethoxy) is optionally further substituted with an alkoxy group, preferably a methoxy group, thus forming a diether substituent.

In certain embodiments according to the present invention, L is a moiety according to the chemical structure:

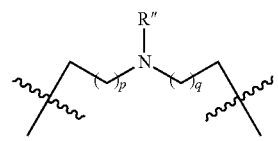

Where R" is H, an optionally substituted $C_1$-$C_{12}$ alkyl group, $Cy^1$ or $(C=O)_z$-G, where $Cy^1$ is an optionally substituted cycloalkyl, aryl or heteroaryl group, G is H or an optionally substituted $C_1$-$C_{12}$ (preferably $C_1$-$C_8$, often $C_1$-$C_3$ alkyl) alkyl, alkene or alkynyl group (wherein optional substituents include a $C_1$-$C_{12}$ (preferably $C_1$-$C_8$) alkyl, alkene or alkynyl group substituted by $(N-R^J)$—$(C_1$-$C_8$ alkyl, alkene or alkynyl group$)_z$-$(Cy^2)_x$, where $R^J$ is H or a $C_1$-$C_8$ alkyl, alkene or alkynyl group, z is 0, 1, 2, 3, 4 or 5, x is 0 or 1 and $Cy^2$ is an optionally substituted aryl or heteroaryl group (most preferably benzyl, quinolinyl, especially 4-aminoquinolinyl or acridinyl, especially 9-aminoacridinyl); and p and q are each independently an integer between 1 and 15, preferably 1, 2, 3, 4, 5, 6, 7, 8, 9 or 10 (in certain aspects, p and q in a molecule are different) with at least one of p or q preferably being at least 2;

and the pharmaceutically acceptable salts, enantiomers, diastereomers, solvents and polymorphs thereof, wherein the length of designated linker group L may vary and wherein the substituents are the same as defined for Formula I.

In still other aspects of the invention L is a moiety according to the chemical structure:

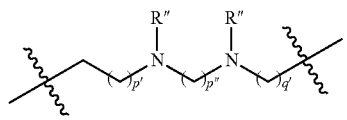

Where each R" is independently H, a $C_1$-$C_{12}$ optionally substituted alkyl group, $Cy^1$ or $(C=O)_z$-G, where $Cy^1$ is an optionally substituted $C_5$-$C_7$ cycloalkyl or an optionally substituted aryl or heteroaryl group, G is H or an optionally substituted $C_1$-$C_{12}$ (preferably $C_1$-$C_8$, often $C_1$-$C_3$ alkyl) alkyl, alkene or alkynyl group (wherein optional substituents include a $C_1$-$C_{12}$ (preferably $C_1$-$C_8$) alkyl, alkene or alkynyl group substituted by $N(R^J)(C_1$-$C_8$ alkyl, alkene or alkynyl group$)_z$-$(Cy^2)_x$, where $R^J$ is H or a $C_1$-$C_8$ alkyl, alkene or alkynyl group, z is 0, 1, 2, 3, 4 or 5 (preferably 0, 1, or 2), x is 0 or 1 and $Cy^2$ is an optionally substituted aryl or heteroaryl group (most preferably benzyl, quinolinyl, especially 4-aminoquinolinyl or acridinyl, especially 9-aminoacridinyl); and p' is an integer from 1-10, preferably 1, 2, 3, 4, 5, 6, 7, 8, 9 or 10;

p" and q' are each independently an integer from 2-10, and preferably at least one of p', p" or q' is different, or a pharmaceutically acceptable salt, enantiomer, diastereomer, solvate or polymorph thereof, wherein the remaining substituents are the same as defined for Formula I or Ia.

In still other embodiments of the invention L is a moiety according to the chemical structure:

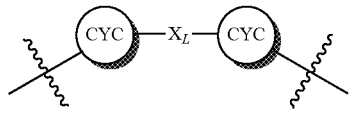

wherein each

is independently an optionally substituted fully or partially saturated 4-7 membered carbocyclic group (e.g. cyclobutyl, cyclopentyl, cyclohexyl, cycloheptyl, optionally substituted with up to 5 hydroxyl or 5 halo groups), or an optionally substituted phenyl group;

$X_L$ is $CR^{CYC}R^{CYC}$, O or $NR^{CYC}$ where $R^{CYC}$ is H or a $C_1$-$C_{12}$ optionally substituted alkyl group, $Cy^1$ or $(C=O)_z$-G, where $Cy^1$ is an optionally substituted $C_5$-$C_7$ cycloalkyl or an optionally substituted aryl or heteroaryl group, G is H or an optionally substituted $C_1$-$C_{12}$ (preferably $C_1$-$C_8$, often $C_1$-$C_3$ alkyl) alkyl, alkene or alkynyl group (wherein optional substituents include a $C_1$-$C_{12}$ (preferably $C_1$-$C_8$) alkyl, alkene or alkynyl group substituted by $N(R^J)(C_1$-$C_8$ alkyl, alkene or alkynyl group$)_z$-$(Cy^2)_x$, where $R^J$ is H or a $C_1$-$C_8$ alkyl, alkene or alkynyl group, z is 0, 1, 2, 3, 4 or 5 (preferably 0, 1, or 2), x is 0 or 1 and $Cy^2$ is an optionally substituted aryl or heteroaryl group (most preferably benzyl, quinolinyl, especially 4-aminoquinolinyl or acridinyl, especially 9-aminoacrindinyl group) or a pharmaceutically acceptable salt, enantiomer, diastereomer, solvate or polymorph thereof, wherein the substituents are the same as defined for Formula I above.

In still other embodiments of the invention, L is a moiety according to the chemical structure:

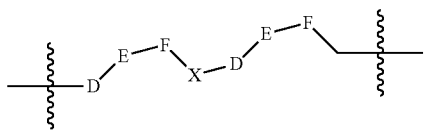

wherein D, E and F are each independently $CH_2$, $CH_2CH_2$, O or NR with the proviso that O is not bonded to NR directly or through a methylene group nor is NR bonded to another NR or X when X is $NR^{CYC}$ either directly or through a methylene group and;

R is H or a $C_1$-$C_{12}$ (preferably $C_1$-$C_8$) optionally substituted alkyl group;

X is $CR^{CYC}R^{CYC}$, O or $NR^{CYC}$; and $R^{CYC}$ is H or a $C_1$-$C_{12}$ optionally substituted alkyl group, $Cy^1$ or $(C=O)_z$-G, where $Cy^1$ is an optionally substituted $C_5$-$C_7$ cycloalkyl or an optionally substituted aryl or heteroaryl group, G is H or an optionally substituted $C_1$-$C_{12}$ (preferably $C_1$-$C_8$, often $C_1$-$C_3$ alkyl) alkyl, alkene or alkynyl group (wherein optional substituents include a $C_1$-$C_{12}$ (preferably $C_1$-$C_8$) alkyl, alkene or alkynyl group substituted by $N(R^J)(C_1$-$C_8$ alkyl, alkene or alkynyl group$)_z$-$(Cy^2)_x$, where $R^J$ is H or a $C_1$-$C_8$ alkyl, alkene or alkynyl group, z is 0, 1, 2, 3, 4 or 5 (preferably 0, 1, or 2), x is 0 or 1 and $Cy^2$ is an optionally substituted aryl or heteroaryl group (most preferably benzyl, quinolinyl, especially 4-aminoquinolinyl, acridinyl, especially 9-aminoacridinyl) or a pharmaceutically acceptable salt, enantiomer, diastereomer, solvate or polymorph thereof, wherein the substituents are the same as defined for Formula I above.

In still embodiments of the invention L is a moiety according to the chemical structure:

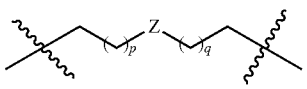

Where Z is CHR or O;

R is H or a $C_1$-$C_{12}$ (preferably $C_1$-$C_8$) optionally substituted alkyl group; and p and q are each independently an integer between 0 and 15, preferably 1, 2, 3, 4, 5, 6, 7, 8, 9 or 10 (in certain aspects, p and q in a molecule are different) with at least one of p or q being at least 1 (especially where Z is O); or a pharmaceutically acceptable salt, enantiomer, diastereomer, solvate or polymorph thereof, wherein the substituents are the same as defined for Formula I above.

In preferred embodiments, in the compound of Formula I, $R^1$, $R^2$, $R^3$, $R^4$, $R^5$, $R^6$, $R^7$, $R^8$, $R^{1'}$, $R^{2'}$, $R^{3'}$, $R^{4'}$, $R^{5'}$, $R^{6'}$, $R^{7'}$ and $R^{8'}$ are each independently H, halo (F, Cl, Br, I), $CH_3$, $CF_3$, OH, COOH, $NH_2$, $NO_2$, CN, $C(O)CH_3$, $OCH_3$, $CH_2OH$, $SO_2NH_2$ and $SO_3H$. In certain preferred embodiments according to the present invention, $R^1$, $R^2$, $R^3$, $R^4$ and $R^{1'}$, $R^{2'}$, $R^{3'}$, $R^{4'}$ are each independently H, F, Cl, $CH_3$, $CF_3$, OH, COOH, $NH_2$, $NO_2$, CN, $C(O)CH_3$, $OCH_3$ and $CH_2OH$.

In preferred embodiments, in the compound of Formula I or IA, $R^1$, $R^2$, $R^3$, $R^4$ and $R^{1'}$, $R^{2'}$, $R^{3'}$, $R^{4'}$ are each independently H, F, Cl or $OCH_3$. In other preferred embodiments, one of $R^1$ and $R^2$ and $R^{1'}$ and $R^{2'}$ is Cl and one of $R^3$ and $R^4$ and $R^{3'}$ and $R^{4'}$ is $OCH_3$ and the remaining substitutents on the acridine ring are hydrogen.

In preferred aspects of the invention, L is a $-(CH_2Y)_n-X-(Y'CH_2)_n-$ group where X is N—R where R is H or $CH_3$ and each n is independently 1, 2, 3, 4, 5, 6, 7, 8, 9, 10, 11 or 12 and Y and Y' are absent or $CH_2$. The linker may be symmetrical (each n is the same integer) or asymmetrical (each n is a different integer).

Preferred compounds according to the present invention include the compounds which are presented in the examples section of the present application as well as FIG. 7 hereof.

In other embodiments, the invention provides methods of treatment and pharmaceutical compositions which use therapeutically-effective amounts of at least one diacridinyl compound according to the present invention (i.e., a compound of Formulae I and/or IA or as otherwise described in the present application) and the pharmaceutically acceptable salts, enantiomers, diastereomers, solvents or polymorphs thereof as otherwise described herein, alone or combination with additional bioactive agents, especially including one or more additional autophagy modulator compounds, further in combination with a pharmaceutically acceptable carrier, additive and/or excipient.

Methods of treatment according to the present invention are directed to the treatment of a disease state and/or condition which is modulated by autophagy as otherwise described herein in a patient in need comprising administering an effective amount of at least one diacridinyl compound according to the present invention, optionally in combination with an additional bioactive agent, including at least one additional autophagy modulator compound or an additional anticancer agent to treat cancer and other autophagy-related disorders.

As described further hereinafter, compounds of the invention exhibit an unexpectedly high level of cytotoxicity in a variety of cancer cells and evidence effective autophagy inhibition at surprising low doses, indicating their effectiveness in the treatment of a broad spectrum of autophagy-related disorders.

The quinacrines reported here show IC50's as low as 0.1 nM, whereas the best chloroquine analog earlier reported has an IC50 of 1.3 µM, a huge difference in activity (thirteen thousand fold). Biological activity is presented in detail in the examples section herein.

These and other aspects of the invention are illustrated further in the Detailed Description of the Invention which follows.

DETAILED DESCRIPTION OF THE INVENTION

Figure 1:
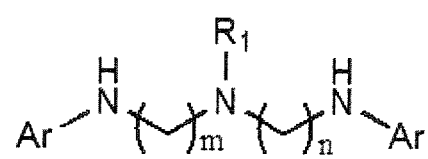
FIG. 1: Dimeric quinacrine have superior anti cancer efficacy amongst dimeric anti-malarials. (A) Schematic of dimeric antimalarials (B) A375P cells were plated in a 384-well highthroughput format and treated with the quinacrine-, mefloquine- and primaquine-based compounds shown (72 hr, 1 nM-30 µM). Viability was standardized to vehicle (water) treated controls and shown are Log IC$_{50}$ values calculated using GraphPad Prism. Alamar blue. (C) A375P cells were treated with the DQ compound library (72 hr, 1 nM-30 µM) MTT. (D) PANC1 cells were treated identically to (C). (E) PANC1 cells were treated with the DQ compound library as well as Lys05, Spautin and SBI-0206965 (72 hr, 3 µM). Apoptosis was assessed by Annexin-V/flow cytometry.
Figure 1:
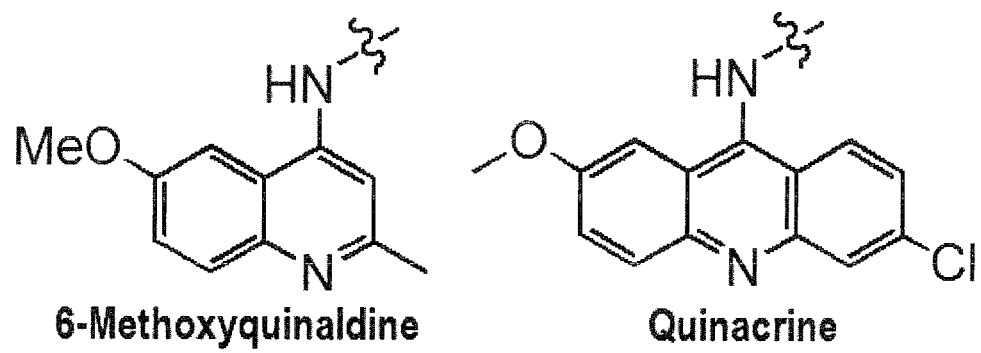
Figure 1:
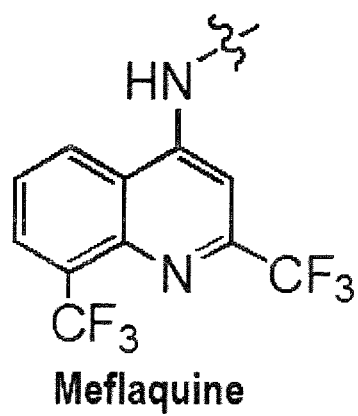
Figure 1:
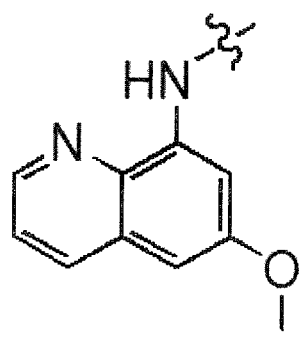
Figure 1:
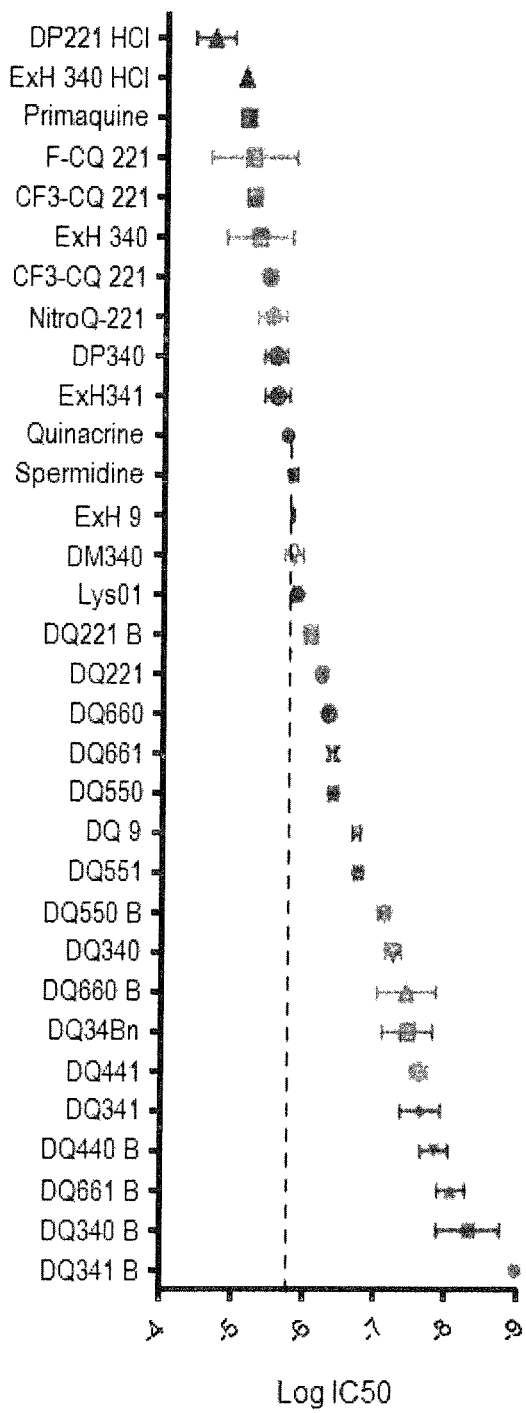
Figure 1:
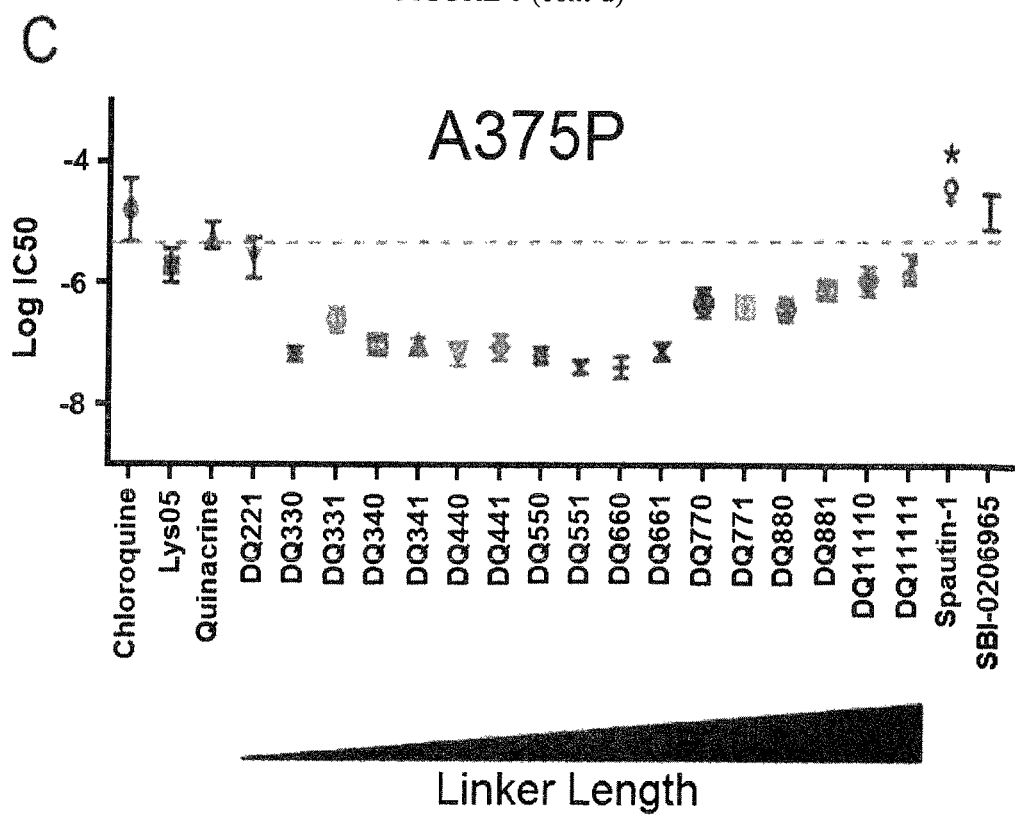
Figure 1:
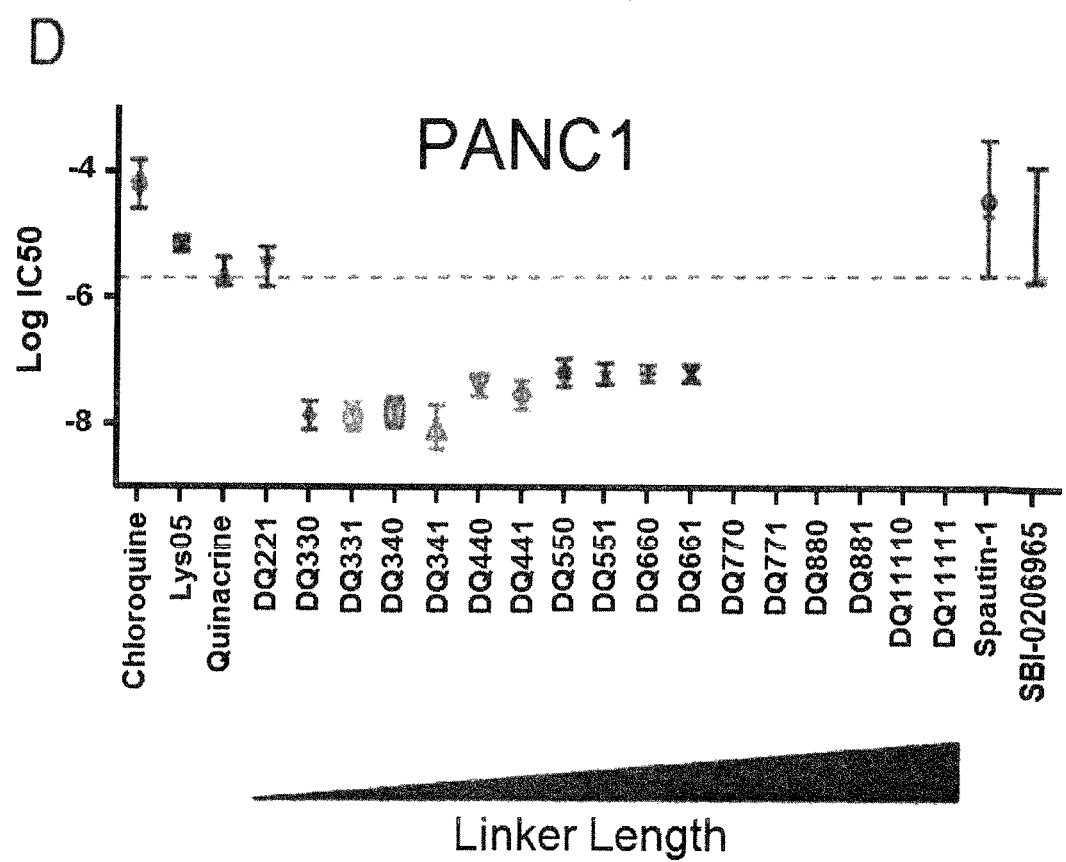
Figure 1:
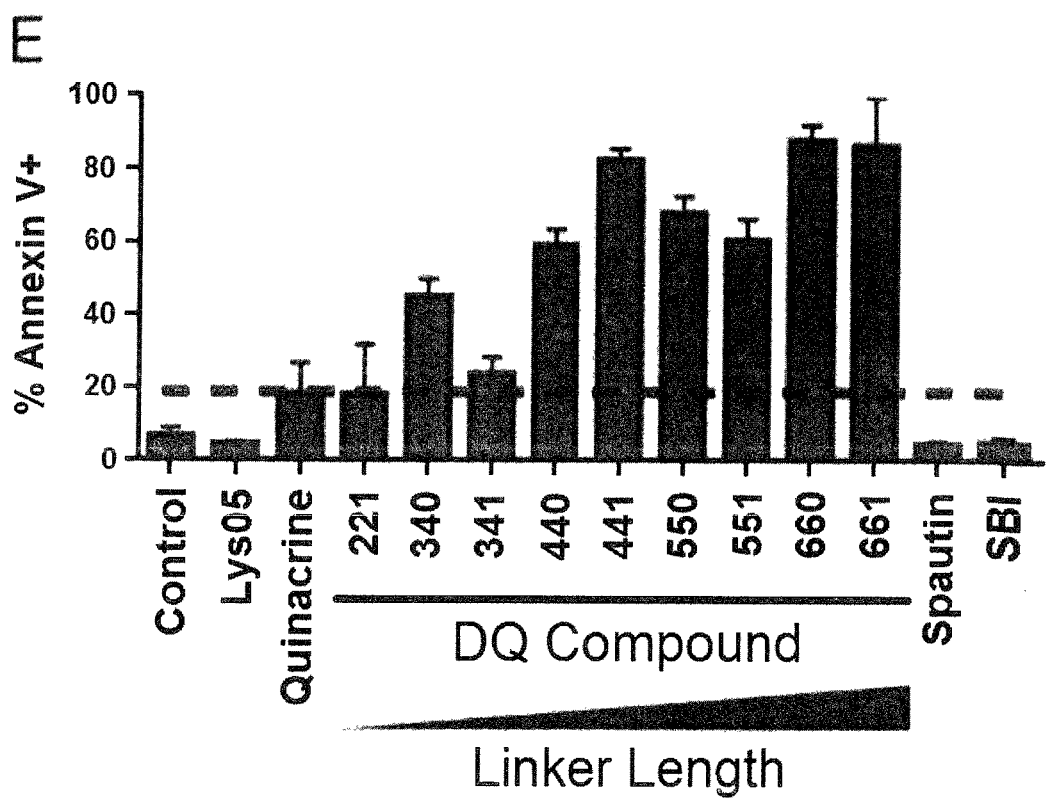

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges that may independently be included in the smaller ranges are also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used. Where a substituent is not disclosed it is presumed (unless contrary to the underlying chemistry) that the substituent is a hydrogen atom.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal and preferably a human, to whom treatment, including prophylactic treatment (prophylaxis), with the compounds or compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "compound" is used herein to describe any specific compound or bioactive agent disclosed herein, including any and all stereoisomers (including diasteromers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein. It is understood that the choice of substituents or bonds within a Markush or other group of substituents or bonds is provided to form a stable compound from those choices within that Markush or other group.

The term "bioactive agent" refers to any biologically active compound or drug which may be formulated for use in the present invention. Exemplary bioactive agents include the compounds according to the present invention which are used to inhibit autophagy and to treat cancer, other autophagy modulator compounds and/or additional anticancer agents as well as other compounds or agents which are otherwise described herein.

The terms "treat", "treating", and "treatment", are used synonymously to refer to any action providing a benefit to a patient at risk for or afflicted with a disease, including improvement in the condition through lessening or suppression of at least one symptom, delay in progression of the disease, prevention or delay in the onset of the disease, etc.

Treatment, as used herein, encompasses both prophylactic and therapeutic treatment, principally of cancer. Compounds according to the present invention can, for example, be administered prophylactically to a mammal in advance of the occurrence of disease to reduce the likelihood of that disease. Prophylactic administration is effective to reduce or decrease the likelihood of the subsequent occurrence of disease in the mammal, or decrease the severity of disease that subsequently occurs, especially including metastasis of cancer. Alternatively, compounds according to the present invention can, for example, be administered therapeutically to a mammal that is already afflicted by disease. In one embodiment of therapeutic administration, administration of the present compounds is effective to eliminate the disease and produce a remission or substantially eliminate the likelihood of metastasis of a cancer. Administration of the compounds according to the present invention is effective to decrease the severity of the disease or lengthen the lifespan of the mammal so afflicted, in the case of cancer.

The term "pharmaceutically acceptable" as used herein means that the compound or composition is suitable for administration to a subject to achieve the treatments described herein, without unduly deleterious side effects in light of the severity of the disease and necessity of the treatment.

The term "inhibit" as used herein refers to the partial or complete elimination of a potential effect, while inhibitors are compounds that have the ability to inhibit.

The term "prevention" when used in context shall mean "reducing the likelihood" or preventing a disease, condition or disease state from occurring as a consequence of administration or concurrent administration of one or more compounds or compositions according to the present invention, alone or in combination with another agent. It is noted that prophylaxis will rarely be 100% effective; consequently the terms prevention and reducing the likelihood are used to denote the fact that within a given population of patients or subjects, administration with compounds according to the present invention will reduce the likelihood or inhibit a particular condition or disease state (in particular, the worsening of a disease state such as the growth or metastasis of cancer) or other accepted indicators of disease progression from occurring.

The term "autophagy" or "autophagocytosis" is used to describe a catabolic process in cells which involves the degradation of a cell's own components through lysosomes. Autophagy is a highly regulated process of biological systems that plays a normal part in cell growth development and homeostasis helping to maintain a balance between the synthesis, degradation, and subsequent recycling of cellular products. It is a major mechanism by which a cell allocates nutrients from unnecessary processes to more-essential processes.

A number of autophagic processes occur in nature, all of which have the degradation of intracellular components via the lysosome as a common feature. A well-known mechanism of autophagy involves the formation of a membrane around a targeted region of a cell, separating the contents from the rest of the cytoplasm. The resultant vesicle then fuses with a lysosome which subsequently degrades the contents.

Autophagy consists of the sequestration of organelles and proteins in autophagic vesicles (AV) and degradation of this cargo through lysosomal fusion (1). Autophagy allows tumor cells to survive metabolic and therapeutic stresses (2-5). Multiple publications indicate therapy-induced autophagy is a key resistance mechanism to many anticancer agents.

An "autophagy-related disorder" includes diseases, disease states and/or conditions which benefit from the inhibition of autophagy, including, but not limited to, cancer (including the metastasis of cancer), rheumatoid arthritis, malaria, antiphospholipid antibody syndrome, lupus, chronic urticaria and Sjogren's disease.

The term "cancer" shall refer to a proliferation of tumor cells having the unique trait of loss of normal controls, resulting in unregulated growth, lack of differentiation, local tissue invasion, and/or metastasis. As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of dysplasia, or loss of differentiation and orientation of cells, and have the properties of invasion and metastasis. The term cancer also within context, includes drug resistant cancers, including multiple drug resistant cancers. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver, lung, nasopharyngeal, neck, thyroid, ovary, pancreas, prostate, and stomach; leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer (e.g., small cell lung cancer, mixed small cell and non-small cell cancer, pleural mesothelioma, including metastatic pleural mesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma; mixed types of neoplasias, particularly carcinosarcoma and Hodgkin's disease; and tumors of mixed origin, such as Wilms' tumor and teratocarcinomas, among others. It is noted that certain epithelial tumors including ovarian, breast, colon, head and neck, medulloblastoma and B-cell lymphoma, among others are shown to exhibit increased autophagy and are principal target cancers for compounds and therapies according to the present invention.

The term "additional anti-cancer agent" is used to describe an additional compound which may be coadministered with one or more compounds of the present invention in the treatment of cancer. Such agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, erythropoietin, epoetin alfa and darbepoetin alfa, ipilumumab, vemurafenib among others. Other anticancer agents which may be used in combination include immunotherapies such ipilumumab, pembrolizumab, nivolumab. with the compounds of the present invention include one or more of the bis-diaminoquinolinyl compounds which are described in WO 2012/149186 and WO 2016/022956, each of which applications is incorporated by reference in their entirety herein.

The term "alkyl" is used herein to refer to a fully saturated monovalent radical containing carbon and hydrogen (up to 10 carbon atoms or as otherwise indicated), and which may be a straight chain, branched or cyclic. Examples of alkyl groups are methyl, ethyl, n-butyl, n-heptyl, isopropyl, 2-methyl propyl, tert-butyl, neopentyl, hexyl, heptyl, octyl, nonyl, decyl, etc.

The term "substituted" as that term relates to alkyl groups which are described above include one or more functional groups such as lower alkyl groups containing 1-6 carbon atoms which are optionally substituted with 1 or 2 hydroxyl groups or between 1 and 5 (preferably 3-5) fluoro groups, acyl ($C_1$-$C_6$), halogen (F, Cl, Br, I, e.g., alkyl halos, e.g., $CF_3$), amido, hydroxyl, carboxy/carboxylic acid, thioamido, cyano, nitro, alkenyl ($C_2$-$C_6$) alkynyl ($C_2$-$C_6$), azido, alkoxy ($C_1$-$C_6$), (including alkoxy groups which are further substituted with a $C_1$-$C_6$ alkoxy group thus producing a diether group), amino, $C_1$-$C_6$ alkylamino and dialkyl-amino, where the alkyl groups may be optionally substituted with 1 or 2 hydroxyl groups or an amine, aminoalkyl or dialkyl group which itself is substituted one or two alkyl groups or a 7-substituted-4-quinolinyl group or a substituted acridinyl group, $C_2$-$C_6$ acylamino, $C_2$-$C_6$ oxyacylester or carboxyester, aryloxy, aryloxy($C_1$-$C_6$)alkyl, carboxamido, thio, $C_2$-$C_6$ ether or thioether, a 7-substituted-4-aminoquinolinyl group (or a substitution on an amine group which forms a 7-substituted-4-aminoqunolinyl group) and the like. Preferred substituents on alkyl groups or a linker which contains at least one amine group, include, for example, at least one hydroxyl group, an amine, monoalkyl amine or dialkyl amine (where one or both alkyl groups is itself further optionally substituted with a dialkyl amine or an amine substituted with one or two (preferably one) 7-substituted-4-quinolinyl group(s) where the amine group is bonded to the 4-position of the quinolinyl group) or an alkoxy group (e.g. methoxy or ethoxy) which may be further substituted with an alkoxy group, preferably a methoxy group, thus forming a diether substituent. Where not identified, a substituent is H.

The term "aryl" refers to a substituted or unsubstituted monovalent aromatic radical having a single ring (e.g., phenyl) or multiple condensed rings (e.g., naphthyl). Other examples include heterocyclic aromatic (heteroaromatic or heteroaryl) ring groups having one or more nitrogen, oxygen, or sulfur atoms in the ring, in particular, quinoline groups or quinacrine groups, in particular, 7-substituted-amino quinoline groups, as well as other groups, including optionally substituted acridine/quinacridinyl groups.

The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes up to 20-membered polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, as well as pyridine, pyridone, pyrimidine, indole, quinoline, isoquinoline, quinolizine, phthalazine, naphthyridine, quinazoline, cinnoline, acridine, benzothiophene, benzofuran, thiazole, benzothiazole, phenothiazine, quinoline (especially 4-aminoquinoline), acridine (especially 9-aminoacridine), isoquinoline, quinolizine, phthalazine, naphthyridine, quinazoline, cinnoline, acridine, benzothiophene, benzofuran, benzothiazole, pyrrolopyrimidine, pyrrolopyrazine, furopyrimidine and phenothiazine, among others.

The term "substituted" as used in the term "substituted aryl, substituted aromatic, substituted heteroaryl, or substituted heteroaromatic" herein signifies that a substitution on the acridinyl may be present, said substituents being selected from atoms and groups, which when present enhance the activity of the compound as an inhibitor of autophagy. Examples of substituents that may be present in a substituted aromatic or heteroaromatic group include, but are not limited to, groups such as H, halo (F, Cl, Br or I), CN, $NO_2$, optionally substituted $C_1$-$C_6$ alkyl (when substituted, preferably substituted with 1 or 2 hydroxyl groups or 3-5 fluoro groups), optionally substituted O—$C_1$-$C_6$ alkyl (preferably, $OCH_3$), optionally substituted $C_2$-$C_7$ acyl (preferably acetyl) or optionally substituted $C_2$-$C_7$ ester (oxycarbonyl ester or carboxyester, preferably carboxyester). It is noted that each of the substituents disclosed herein may themselves be substituted. Where not identified, a substituent is H.

The term "co-administration" or "adjunct therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, including sequential administration. Preferably, effective concentrations of all co-administered compounds or compositions are found in the subject at a given time. The term co-administration or adjunct therapy also contemplates other bioactive agents being coadministered with pharmaceutical compositions according to the present invention, especially where a cancer has metastasized or is at risk for metastasis.

The term "radiotherapy" or "radiation therapy" is used to describe therapy for cancer which may be used in conjunction with the present compounds. Radiation therapy uses high doses of radiation, such as X-rays, or other energy sources such as radioisotopes (gamma, beta or alpha emitters), to destroy cancer cells. The radiation damages the genetic material of the cells so that they can't grow. Although radiation damages normal cells as well as cancer cells, the normal cells can repair themselves and function, while the cancer cells cannot.

Radiation therapy may be used in combination with the presently claimed compounds, alone or in combination with additional anticancer compounds as otherwise disclosed herein, depending on the cancer to be treated. Radiotherapy therapy is most effective in treating cancers that have not spread outside the area of the original cancer, but it also may be used if the cancer has spread to nearby tissue. Radiotherapy is sometimes used after surgery to destroy any remaining cancer cells and to relieve pain from metastatic cancer.

Pharmaceutical Compositions

Compounds according to the present invention may be readily formulated into pharmaceutical compositions, useful in the inhibition of autophagy in a biological system and/or the inhibition, treatment or prevention of diseases states and/or conditions which benefit from the inhibition of autophagy including cancer (and its metastasis and recurrence), rheumatoid arthritis, malaria, antiphospholipid antibody syndrome, lupus (systemic lupus erythematosus), chronic urticaria and Sjogren's disease. Pharmaceutical compositions comprise an effective amount of one or more compounds according to the present invention in combination with a pharmaceutically acceptable carrier, additive or excipient, optionally in combination with at least one additional agent, in the case of cancer, preferably an anticancer agent as otherwise described herein. Additional anticancer agents include the dimeric As noted above, the compounds and method of the invention may be used to inhibit autophagy as otherwise described herein, and are useful for the inhibition (including prophylaxis) and/or treatment of cancer and its metastasis, rheumatoid arthritis, malaria, antiphospholipid antibody syndrome, lupus (systemic lupus erythematosus), chronic urticaria and Sjogren's disease. The treatment of cancer or malaria are important aspects of the present invention.

In methods according to the present invention, subjects or patients in need are treated with the present compounds, pharmaceutical compositions in order to inhibit, reduce the likelihood or treat a disease state, condition and/or infection as otherwise described herein. The disease states, conditions and infections treated by the present compounds and compositions are readily recognized and diagnosed by those of ordinary skill in the art and treated by administering to the patient an effective amount of one or more compounds according to the present invention.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection, among others, including buccal, rectal and transdermal administration. Subjects contemplated for treatment according to the method of the invention include humans, companion animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition is about 0.1% to about 85%, about 0.5% to about 75% by weight of a compound or compounds of the invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or is apparent to those skilled in the art; for example, see Remington's Pharmaceutical Sciences (17th Ed., Mack Pub. Co., 1985). The composition to be administered will contain a quantity of the selected compound in a pharmaceutically effective amount for inhibiting autophagy in a biological system, including a patient or subject according to the present invention.

Method of Treatment

According to one aspect of the invention, a method is provided for treating a mammalian patient or subject to inhibit autophagy in that patient or subject. Compounds according to the present invention described herein may be used to inhibit autophagy in a manner consistent with inhibiting, treating and/or preventing disease states and/or conditions including cancer (including metastasis of cancer), rheumatoid arthritis, malaria, antiphospholipid antibody syndrome, lupus, chronic urticaria and Sjogren's disease.

According to the present invention, in patients or subjects in need thereof, are treated by administering to the patient or subject an effective amount of one or more compounds according to the present invention, optionally in combination with at least one additional bioactive agent useful for treating the same disease state or condition. Compounds according to the present invention may be used to inhibit, reduce the likelihood or treat cancer, including the metastasis of cancer in a patient or subject in need of such treatment. The treatment is useful for any cancer for which inhibition of autophagy represents a favorable result or for which metastasis is a risk element. Therapy with at least one additional anticancer agent as otherwise described herein is also contemplated in the present methods. The numerous cancers which may be treated pursuant to the present method are described hereinabove.

In another aspect the present invention is directed to a method for treating a disease state and/or condition which benefits from the inhibition of autophagy, including rheumatoid arthritis, malaria, antiphospholipid antibody syndrome, lupus, chronic urticaria and Sjorgen's disease. In this method, a patient or subject in need of treatment is administered an effective amount of a compound as otherwise described herein optionally in combination with a pharmaceutically acceptable carrier, additive or excipient in order to inhibit, treat and/or prevent the above disease states of conditions.

In certain preferred embodiments of the compounds of Formulae IA, $R^1$, $R^2$, $R^3$, $R^4$, $R^{1'}$, $R^{2'}$, $R^{3'}$ and $R^{4'}$ are each independently H, a halo group, a nitro group or a trifluoromethyl group, preferably a chloro group. In compounds according to the present invention R and R' are often each independently H, a $C_1$-$C_3$ optionally substituted alkyl group itself preferably substituted with at least one hydroxyl group, an amine, monoalkyl amine or dialkyl amine group, wherein said amine group or said monoalkyl amine group is optionally substituted on the amine position with a 7-substituted-4-quinolinyl group wherein the amine binds to the 4-position of the quinolinyl group or an optionally substituted 9-aminoacridinyl group, or one or both alkyl groups of said monoalkyl amine or dialkyl amine is itself further optionally substituted with at least one hydroxyl group, an amine, a monoalkyl amine or a dialkyl amine wherein the amine or monoalkyl amine is optionally substituted on the amine position with one or two 7-substituted-quinolinyl group(s) (the 7-position of each quinolinyl group may be substituted with $R^1$ and/or $R^{1'}$) or one or two optionally substituted 9-aminoacridinyl groups, or an alkoxy group (e.g. methoxy or ethoxy) which alkoxy group may be further substituted with an alkoxy group, preferably a methoxy group (thus forming a diether substituent).

Further preferred methods relate to the use/administration of the compounds according to the present invention which are presented in the various schemes and figures as well as the examples section of the present application, which sets for the preparation of preferred compounds according to the present invention.

In the methods treating or inhibiting cancer or the metastasis of cancer, the compounds described above may be coadministered with at least one additional anticancer agent including, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamnidronate, pentostatin, plicamycin, porfimer, procarbazine, raltitrexed, rituxinab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others, and mixtures thereof. Other combinations of interest include coadministration of the above compounds with immunotherapies such as ipilimumab, pembrolizumab and nivolumab, among others.

In methods involving infections, disease states and/or conditions caused by rheumatoid arthritis, malaria, antiphospholipid antibody syndrome, lupus, chronic urticaria and Sjogren's disease, the compounds according to the present invention may be coadministered with additional agents which are traditionally used in therapy for these disease states and/or conditions.

Synthetic Chemistry—Overview of Synthetic Approaches to Compounds of the Invention As will be described herein below, compounds according to the present invention are readily synthesized using well-known chemical synthetic methods which utilize precursors/reactants which are generally available either from commercial sources or readily synthesized from methods which are well known in the art. Accordingly, the inventors provide several schemes for the synthesis of virtually any compound which is presently disclosed. These syntheses are all well within the capability of the skilled chemist, following well-known literature methods. In addition, the inventors have provided a number of chemical syntheses in the examples section which are detailed herein below. Additional approaches to synthesizing some of the compounds according to the present invention, including linkers described herein may be found in international applications WO 2012/149186 and WO 2016/022956, which are incorporated by reference herein.

The standard method for the synthesis of acridines is by cyclization of 1 to give the acridone 2, which on reaction of POCl₃ is known to give 3 (See Scheme 1, below; for a recent example, see Anderson, et. al., Bioorg. Med. Chem. Lett. 2006, 14, 334-343).

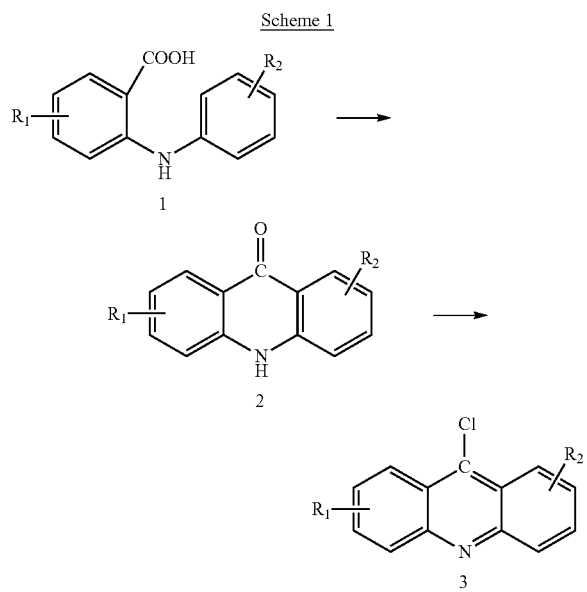

The key substrate 1 is obtained in turn by one of two complementary approaches that are outlined in Scheme 2 below. The key substrate 1 can be prepared by a Buchwald-Hartwig coupling either from 4 and 5, or alternatively, from 6 and 7.

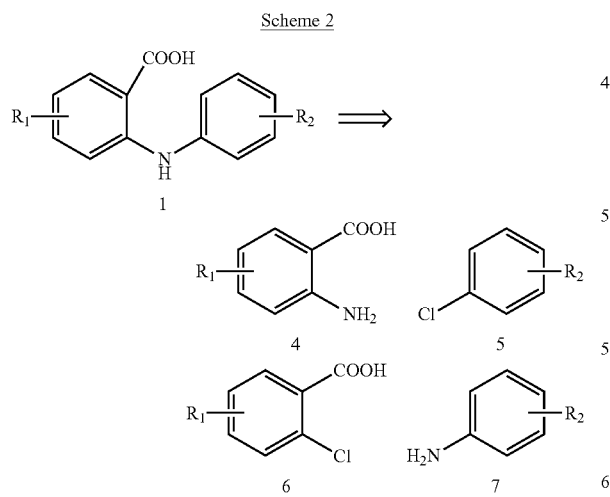

Retention of the methoxy and chlorine functionalities that are present in the parent acridine 10, then the desired product could be obtained by coupling the generic structures 8 and 9. Indicated in Scheme 3 are the substitutions in 8 and 9 that are commercially available, thereby enabling the preparation of this family of analogs that carry substitution at C-4, C-5 and C-8, respectively, of the structure of 10. See scheme 3, below.

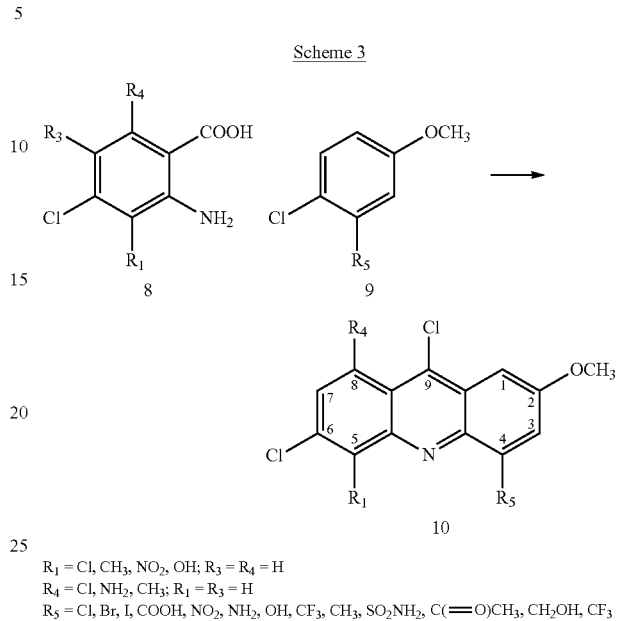

$R_1$ = Cl, CH₃, NO₂, OH; $R_3$ = $R_4$ = H
$R_4$ = Cl, NH₂, CH₃; $R_1$ = $R_3$ = H
$R_5$ = Cl, Br, I, COOH, NO₂, NH₂, OH, CF₃, CH₃, SO₂NH₂, C(=O)CH₃, CH₂OH, CF₃

Alternatively, the synthesis of compounds in which the chlorine at the C-6 position is moved to the C-7 position, as shown in 12 (Scheme 4) would result from the coupling of the generic structures 11 and 9. Again, a series of commercially available derived structures leads to the substituted analogs of 12.

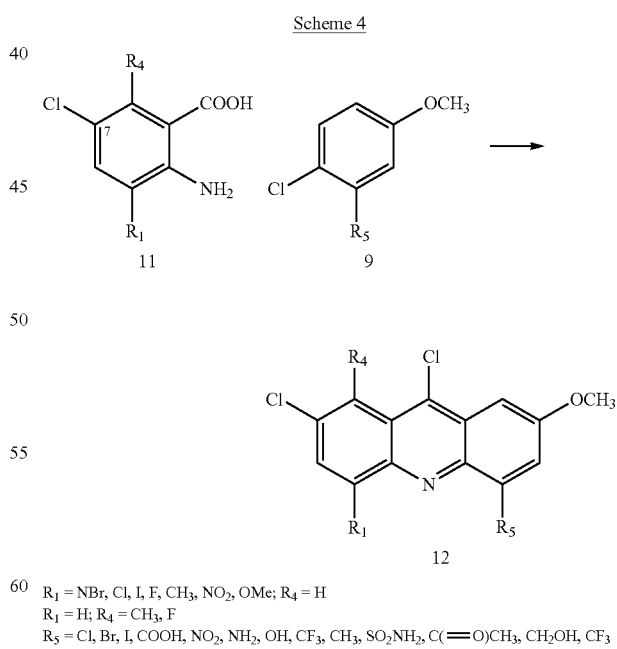

$R_1$ = NBr, Cl, I, F, CH₃, NO₂, OMe; $R_4$ = H
$R_1$ = H; $R_4$ = CH₃, F
$R_5$ = Cl, Br, I, COOH, NO₂, NH₂, OH, CF₃, CH₃, SO₂NH₂, C(=O)CH₃, CH₂OH, CF₃

The preparation of derivatives of the quinacrine heterocycle that do not contain a chlorine atom at each C-6 or C-7 (as indicated in 14) is outlined in Scheme 5, below.

Scheme 5

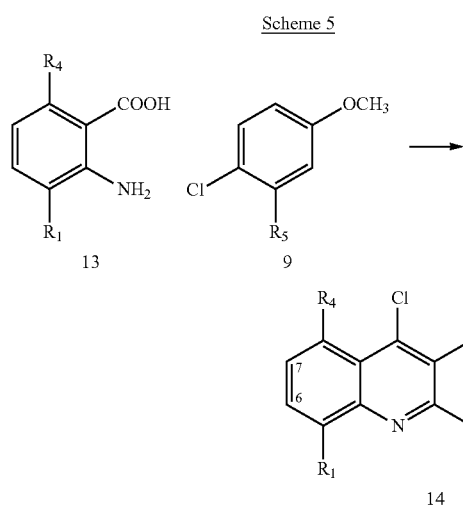

$R_1$ = $NO_2$, Cl, Br, I, F, $CH_3$, COOH, $NH_2$, OH, OMe; $R_4$ = H
$R_1$ = H; $R_4$ = $NO_2$, Cl, Br, I, F, $CH_3$, OMe
$R_5$ = Cl, Br, I, COOH, $NO_2$, $NH_2$, OH, $CF_3$, $CH_3$, $SO_2NH_2$, C(=O)$CH_3$, $CH_2OH$, $CF_3$

The alternative approach to the synthesis of the key substrate 1 (Scheme 1) involves the chlorine substituent on the left-hand ring 15 and the amino (—$NH_2$) group on the right-hand ring which would lead to the same product 10 (Scheme 6, below) that was previously described in Scheme 3, above, although with slightly different substitutions from commercially available compounds.

Scheme 6

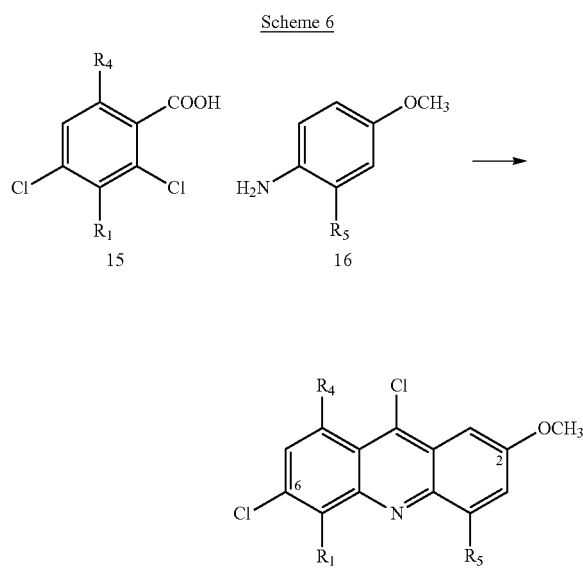

$R_1$ = Br, Cl, F, $NH_2$; $R_4$ = H
$R_1$ = H; $R_4$ = Br, Cl, F, OH, $CH_3$, $NH_2$
$R_5$ = Br, Cl, F, I, $OCH_3$, OH, $CH_3$, C(O)$CH_3$, $NO_2$, CN, $SO_3H$, COOH, $CH_2OH$

Removal of the chlorine substituent in 10 (Scheme 6) gives 14, the synthesis of which was shown in Scheme 5, but could also be achieved via the coupling of 17 and 16 (Scheme 7) that would make the indicated substitution patterns possible from commercially available precursors.

Scheme 7

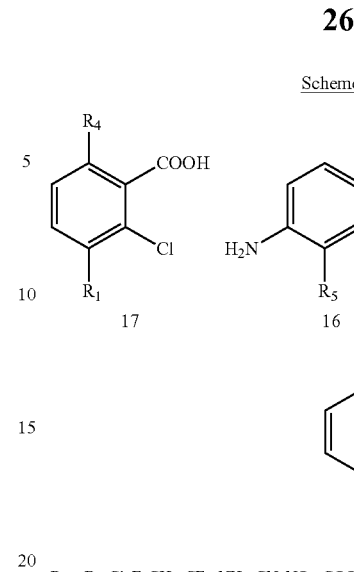

$R_1$ = Br, Cl, F, $CH_3$, $CF_3$, $NH_2$, CN, $NO_2$, COOH, OMe; $R_4$ = H
$R_1$ = H; $R_4$ = Br, Cl, F, OH, OMe, COOH, $CF_3$, $NO_2$
$R_5$ = Br, Cl, F, I, $OCH_3$, OH, $CH_3$, C(O)$CH_3$, $NO_2$, CN, $SO_3H$, COOH, $CH_2OH$

Once the acridine precursors are obtained, they are then dimerized with linkers as otherwise described herein pursuant to methods which are described herein below.

EXAMPLES

Synthetic Chemistry

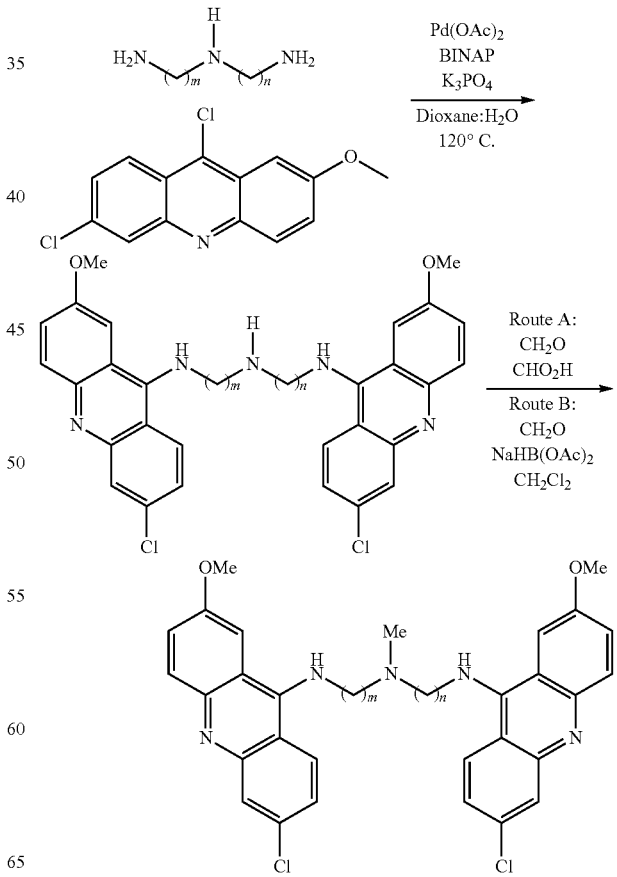

General Procedure for Buchwald-Hartwig Amination

To a sealable vial, triamine (1.0 Eq), Arylhalide (2.2 eq), Pd(OAc)$_2$ (0.05 eq), racemic BINAP (0.10 eq), and K$_3$PO$_4$ (3.0 eq) were added. The reaction vessel was sealed, evacuated and placed under an argon atmosphere. To the vial, a solution of 10:1 1,4-Dioxane:Water (degassed by freeze-pump-thaw method) was added, and the reaction was heated to 120 C. Upon completion the reaction was allowed to cool to room temperature and filtered through celite using either CHCl$_3$ or CH$_2$Cl$_2$, and concentrated. The compounds were then dissolved in a minimum amount of either ethyl acetate, or CH$_2$Cl$_2$. The HCl salt was formed by added 3.0 eq of HCl in diethyl ether. The precipitate was filtered and collected, and the organic layer is washed 3× with H$_2$O. The precipitate was dissolved in H$_2$O unless specified. The H$_2$O layer was then washed once with CH$_2$Cl$_2$. Following the organic wash, the pH of the aqueous layer was adjusted to 12 by the addition of aqueous ammonium hydroxide. The aqueous layer was then extracted with 25% 2-propanol in CHCl$_3$, and dried over sodium sulfate. The organic reaction was concentrated to a solid or film yielding the dimeric inhibitor. Further purification used when specified.

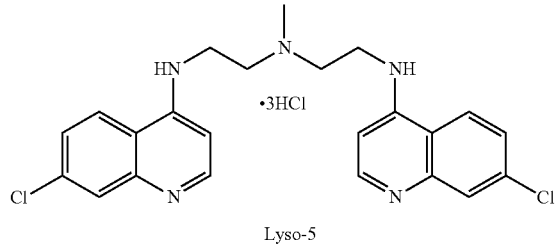

Lys 05

Lyso-5

Lys 05 was synthesized and isolated according to the general procedure above. The compound was isolated as a pure compound as an orange solid (2.74 g, 71%). R$_f$=0.70 (CHCl$_3$:MeOH:TEA; 85:10:5); Mp=199-200° C., EtOAc (Lit.,$^{PNAS}$ 199-200° C.); $v_{max}$ (neat/cm$^{-1}$) 3622, 3012, 2947, 2831, 1697, 1516, 1458, 1219, 1026, 760; m/z (ES) 440.35 (MH$^+$, 100%), 443.35 (MH$^+$, 65%) 438.32 (MH$^-$, 100%), 440.35 (MH$^-$, 50%); $\delta_H$ (500 MHz, CDCl$_3$) 2.46 (1H, s, CH$_3$), 2.89 (4H, t, J=6.0 Hz, CH$_2$), 3.40 (4H, quart., J=5.0 Hz, CH$_2$), 5.45 (2H, s (br), NH), 6.38 (2H, d, J=5.5 Hz, ArH), 6.99 (2H, dd, J=9.0, 2.0 Hz, ArH), 7.41 (2H, d, J=9.0 Hz, ArH), 7.94 (2H, d, J=2.0 Hz, ArH), 8.53 (2H, d, J=5.5 Hz, ArH) ppm.

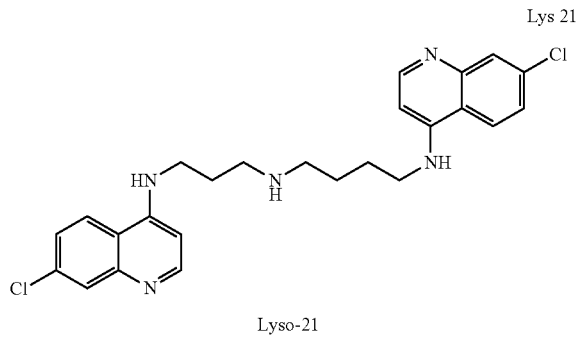 [SMILES: Clc1ccc2c(NCCCCNCCCNc3ccnc4cc(Cl)ccc34)ccnc2c1]

Lys 21

Lyso-21

Lys 21 was synthesized and isolated according to the general procedure above. The product as a white solid (785 mg, 91% yield). R$_z$=0.10 (EtOAc:MeOH:TEA; 80:15:5); $\delta_H$ (500 MHz, MeOD) 1.69-1.71 (2H, m, CH$_2$), 1.76-1.82 (2H, m, CH$_2$), 1.92-1.98 (2H, m, CH$_2$), 2.70 (2H, t, J=7.0 Hz, CH$_2$), 2.78 (2H, t, J=7.0 Hz, CH$_2$), 3.37-3.44 (4H, m, CH$_2$), 6.51-6.53 (2H, m, ArH), 7.36-7.39 (2H, m, ArH), 7.77 (2H, t, J=2.0 Hz, ArH), 8.04-8.09 (2H, m, ArH), 8.34 (2H, t, J=5.5 Hz, ArH) ppm

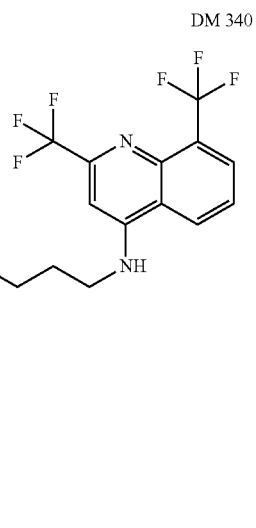

DM 340

DM340

To a vial was added 3-Chloro-2,8-bis(trifluoromethyl) quinoline (558.00 mg, 1.86 mmol, 2.40 equiv), BINAP (72.00 mg, 0.12 mmol, 0.15 equiv.), Pd(OAc)$_2$ (14.00 mg, 0.06 mmol, 0.075 equiv.), finely ground K$_3$PO$_4$ (659.00 mg, 3.10 mmol, 4.00 equiv.) and spermidine (120.0 µL, 0.78 mmol, 1.00 equiv.). The reagents were placed under a blanket of Argon; then a mixture of degassed dioxane and water (3 mL, 10:1) was added. The reaction vial was sealed and heated to 120° C. for 12 hours. The reaction was then cooled to room temperature and filtered on a pad of celite; washing with chloroform (3×10 mL). Combined organic layers were acidified to pH 1 using 1M aqueous HCl solution (4.7 mL, 4.66 mmol, 6.00 equiv) and diluted with water (20 mL). The resulting biphasic mixture was separated and the water layer was washed with chloroform (2×15 mL). The pH of the aqueous layer was adjusted to 11 using ammonium hydroxide. The now alkaline mixture was washed with chloroform (3×20 mL). These 3 chloroform extracts were combined, washed with brine, dried over Na$_2$SO$_4$ and concentrated which afforded the product as an off-white foam (243.00 mg, 50% yield). The purity of this material was calculated to be ≥95% which negated the need for further purification. R$_f$=0.25 (CCl$_3$:MeOH:TEA; 85:10:5); Mp=84-87° C.; $v_{max}$ (neat/cm$^{-1}$) 3406, 3020, 2976, 1523, 1215, 771; HRMS (ES) calcd for C$_{29}$H$_{26}$F$_{12}$N$_5$ 672.1997, found 672.2033; $\delta_H$ (500 MHz, DMSO) 1.55-1.60 (2H, m, CH$_2$), 1.70-1.75 (2H, m, CH$_2$), 1.79-1.85 (2H, m, CH$_2$), 2.58 (2H, t, J=7.0 Hz, CH$_2$), 2.65 (2H, t, J=6.0 Hz, CH$_2$), 3.39-3.43 (4H, m, CH$_2$), 6.86 (2H, d, J=7.5 Hz, ArH), 7.59-7.66 (2H, m, ArH), 8.03 (1H, s (br), NH), 8.08 (1H, d, J=7.0 Hz, ArH), 8.12 (1H, d, J=7.0 Hz, ArH), 8.26 (1H, s (br), NH), 8.53 (1H, d, J=8.5 Hz, ArH), 8.61 (1H, d, J=8.5 Hz, ArH) δ ppm; Sc (125 MHz, DMSO) 25.9, 27.3, 28.0, 41.6, 42.8, 47.5, 49.4, 94.4, 119.7, 119.7, 120.9, 123.1, 124.8 (d), 126.6, 126.8, 127.2, 127.3, 129.3 (br), 144.17, 144.23, 152.7, 152.8 ppm.

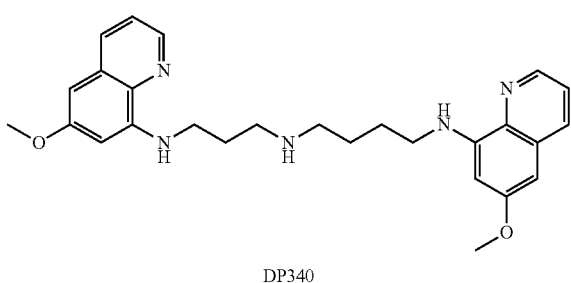

DP340

To a vial was added 8-Chloro-6-methoxyquinoline (193.0 mg, 1.0 mmol, 2.20 equiv), BINAP (45.00 mg, 0.072 mmol, 0.16 equiv.), $Pd_2(dba)_3$ (33.00 mg, 0.036 mmol, 0.08 equiv.), NaOtBu (130.0 mg, 1.37 mmol, 3.0 equiv) L, 0.455 mmol, 1.00 equiv.) and spermidine (71.0 μL, 0.455 mmol, 1.00 equiv.). The reagents were placed under a blanket of Argon; then 1 mL of dry dioxane was added. The reaction vial was sealed and heated to 110° C. for 48 hours. The reaction was then cooled to room temperature and filtered on a pad of celite; washing with chloroform (3×10 mL). The filtrate was concentrated and dissolved with methanol and dichloromethane, and adsorbed onto 400 mg of $SiO_2$. These materials were separated via flash column chromatography (EtOAc:MeOH:TEA; 90:9:1) to afford the product as a red brown solid (173 mg, 83%); HRMS (ES) calcd for $C_{27}H_{34}N_5O_2$ 460.2713, found 460.2707; $\delta_H$ (500 MHz, $CDCl_3$) 1.69-1.75 (2H, m, $CH_2$), 1.90-1.98 (2H, m, $CH_2$), 2.17-2.22 (2H, m, $CH_2$), 2.93 (2H, t, J=7.5 Hz, $CH_2$), 3.06 (2H, t, J=7.5 Hz, $CH_2$), 3.19 (2H, t, J=7.0 Hz, $CH_2$), 3.34-3.37 (2H, m, $CH_2$), 3.86 (3H, s, $CH_3$), 3.87 (3H, s, $CH_3$), 6.07 (2H, s (br), NH), 6.23 (1H, d, J=2.5 Hz, ArH), 6.27 (1H, d, J=2.5 Hz, ArH), 6.34 (2H, dd, J=2.5, 8.0 Hz, ArH), 7.24-7.26 (2H, m, ArH), 7.86-7.89 (2H, m, ArH), 8.51 (2H, dd, J=1.5, 4.0 Hz, ArH) ppm; $\delta_C$ (125 MHz, $CDCl_3$) 26.2 (2C's), 29.6, 40.8, 42.7, 46.3, 47.9, 55.1 (2C's), 92.2, 92.6, 96.8, 97.1, 121.75, 121.81, 129.60, 129.61, 134.6, 135.17, 135.19, 144.3, 144.5, 145.3, 145.5, 159.2, 159.3 ppm.

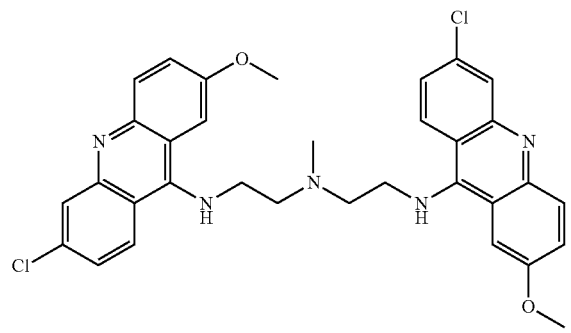

DQ221

DQ 221 was synthesized according to the general scheme above. Required flash column chromatography (EtOAc:MeOH:TEA; 90:9:1) to afford the product as a red solid (240.00 mg, 33%). $R_f$=0.15 (EtOAc:MeOH:TEA; 92:7:1); Mp=163-164° C.; $v_{max}$ (neat/cm$^{-1}$) 3688, 3619, 3019, 1219, 929; HRMS (ES) calcd for $C_{33}H_{32}Cl_2N_5O_2$ 600.1933, found 600.1935 (matches double Cl pattern); $\delta_H$ (500 MHz, $CDCl_3$) 2.45 (3H, s, $CH_3$), 2.88 (4H, t, J=6.0 Hz, $CH_2$), 3.73 (6H, s, $CH_3$), 3.85 (4H, t, J=6.0 Hz, $CH_2$), 5.65 (2H, s (br), NH), 7.16 (2H, d, J=9.0 Hz, ArH), 7.21 (2H, d, J=2.5 Hz, ArH), 7.32 (2H, d, J=8.5 Hz, ArH), 7.95 (2H, d, J=9.0 Hz, ArH), 8.01-8.07 (4H, m, ArH) ppm; $\delta_C$ (125 MHz, $CDCl_3$) 42.0, 47.4, 55.4, 57.9, 99.5, 115.5, 117.8, 124.3, 124.4, 127.5, 130.8, 135.1, 145.9, 147.8, 149.9, 156.1 ppm.

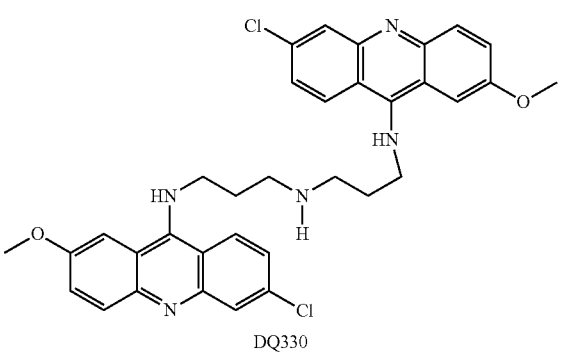

DQ330

DQ 330 was prepared by the above general procedure. The workup was altered from the general procedure as follows. After formation of the HCl salt, and following the standard workup showed little product moved into the aqueous layer, therefore the collected precipitate (380 mg) was recrystallized from methanol yielding (229 mg). The HCl salt solubilized in a solution of a 1:1 mixture of dichloromethane to basic methanol. The residue was dissolved in dichloromethane, washed with water (2×20 mL) then washed with brine and dried over $Na_2SO_4$. Concentration of the organic phase yielded an orange solid (172 mg, 56%). $v_{max}$ (neat/cm$^{-1}$) 2925, 2853, 1631, 1562, 1466, 1238. $^1$H NMR (500 MHz, Chloroform-d) δ 8.01-7.96 (m, 2H), 7.92 (d, J=9.3 Hz, 4H), 7.33 (dd, J=9.4, 2.7 Hz, 2H), 7.21 (d, J=2.7 Hz, 2H), 7.10 (dd, J=9.2, 2.2 Hz, 2H), 6.01 (s, 2H), 3.83-3.75 (m, 10H), 3.49 (s, 1H), 2.82 (t, J=6.3 Hz, 4H), 1.89 (p, J=6.4 Hz, 4H). $^{13}$C NMR (126 MHz, $CDCl_3$) δ 155.56, 149.93, 134.72, 124.37, 123.86, 123.72, 117.50, 115.26, 100.41, 77.30, 77.05, 76.79, 55.52, 49.90, 48.65, 30.87, 25.41.

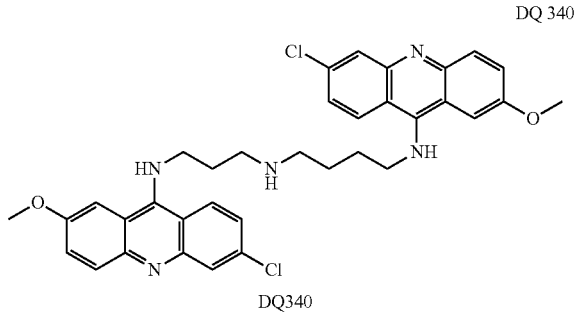

DQ340

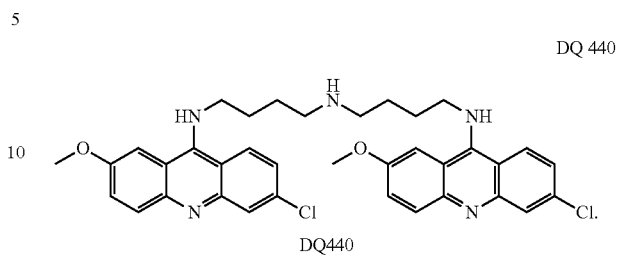

DQ440

DQ 340 was synthesized according to the above general procedure. The isolated product yielded a mixture of the dimeric product and the monomer (3:7, 369.00 mg). These materials were separated via flash column chromatography (EtOAc:MeOH:TEA; 84:16:1) to afford the product as a red solid (119.00 mg, 15%). $R_f$=0.10 (EtOAc:MeOH:TEA; 84:15:1); Mp=115-118° C.; $v_{max}$ (neat/cm$^{-1}$) 3435, 3019, 1635, 1216, 929; HRMS (ES) calcd for $C_{35}H_{36}Cl_2N_5O_2$ 628.2246, found 628.2247 (matches double Cl pattern); $\delta_H$ (500 MHz, CDCl$_3$) 1.68-1.74 (2H, m, CH$_2$), 1.80-1.86 (2H, m, CH$_2$), 1.88-1.92 (2H, m, CH$_2$), 2.73 (2H, t, J=7.0 Hz, CH$_2$), 2.89 (2H, t, J=7.0 Hz, CH$_2$), 3.74 (2H, t, J=7.0 Hz, ArH), 3.87 (3H, s, CH$_3$), 3.89-3.92 (5H, m, CH$_3$, and CH$_2$), 7.11-7.24 (3H, m, ArH), 7.31-7.39 (3H, m, ArH), 7.95-8.04 (6H, m, ArH) ppm; $\delta_C$ (125 MHz, CDCl$_3$) 27.2, 29.5, 30.1, 49.0, 49.7, 50.5, 50.8, 55.6 (2C), 99.5, 101.3, 117.9, 118.4, 118.5, 120.6, 123.5, 123.6, 124.1, 124.4, 124.5, 124.8, 134.9, 135.2, 148.2, 149.7, 150.8, 155.4, 156.0 ppm.

DQ 440 was synthesized according to the above general procedure yielding the product as an orange foam (0.35 g, 39% yield). $R_f$=0.25 (EtOAc:MeOH:TEA; 80:15:5); Mp=58-62° C.; $v_{max}$ (neat/cm$^{-1}$) 3943, 3688, 3054, 2987, 2685, 1631, 1559, 1528, 14211264, 1032, 896; HRMS (ES) calcd for $C_{36}H_{38}N_5O_2Cl_2$ 642.2403, found 642.2402; $\delta_H$ (500 MHz, CDCl$_3$) 1.55-1.61 (4H, m, CH$_2$), 1.72-1.78 (4H, m, CH$_2$), 2.60 (4H, t, J=7.0 Hz, CH$_2$), 3.68-3.71 (4H, m, CH$_2$), 3.92 (6H, s, CH$_3$), 7.23 (2H, d, J=2.5 Hz, ArH), 7.26 (2H, dd, J=2.0, 9.0 Hz, ArH), 7.40 (2H, dd, J=2.5, 9.5 Hz, ArH), 7.98-8.00 (4H, m, ArH), 8.05 (2H, d, J=1.5 Hz, ArH) ppm; $\delta_C$ (125 MHz, CDCl$_3$) 27.5, 29.5, 49.3, 50.6, 55.6, 67.1, 99.6, 115.9, 117.9, 124.1, 124.2, 124.4, 128.3, 131.6, 134.7, 146.9, 148.4, 149.8, 155.9 ppm.

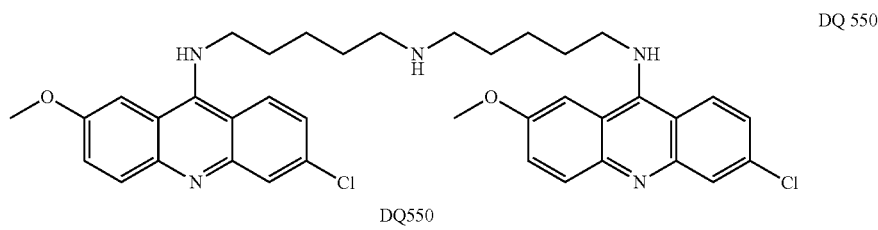

DQ550

DQ 550 was synthesized according to the above general procedure yielding the product as an orange solid (0.73 g, 83% yield). $R_f$=0.15 (EtOAc:MeOH:TEA; 84:15:1); Mp=52-54° C.; $v_{max}$ (neat/cm$^{-1}$) 3943, 3692, 3054, 2987, 2934, 2858, 2685, 1631, 1560, 1519, 1421, 1265, 896; HRMS (ES) calcd for $C_{38}H_{42}N_5O_2Cl_2$ 670.2716, found 670.2715 (matches double Cl pattern); $\delta_H$ (500 MHz, CDCl$_3$) 1.47 (8H, s (br), CH$_2$), 1.73-1.75 (4H, m, CH$_2$), 2.51-2.53 (4H, m, CH$_2$), 3.65-3.66 (4H, m, CH$_2$), 3.93 (6H, s, CH$_3$), 7.19 (2H, s (br), ArH), 7.25 (2H, s (br), ArH), 7.38-7.40 (2H, m, ArH), 7.96-7.98 (4H, m, ArH), 8.04 (2H, s (br), ArH) ppm; $\delta_C$ (125 MHz, CDCl$_3$) 24.7, 29.7, 31.6, 49.7, 50.5, 55.5, 99.3, 115.8, 117.9, 124.0, 124.4 (2C), 128.1, 131.4, 134.8, 146.6, 148.3, 149.7, 156.0 ppm.

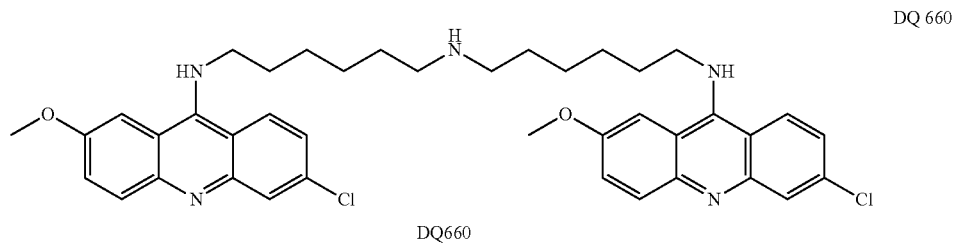

DQ660

DQ 660 was synthesized according to the general procedure above. This compound, the precipitated HCl salt was recrystallized in methanol, and then solubilized in a solution of a 1:1 mixture of dichloromethane to basic methanol. The residue was dissolved in dichloromethane, washed with water (2×20 mL) then washed with brine and dried over $Na_2SO_4$. Evaporation yielded an orange solid (4.28 g, 68%). $R_f$=0.30 (EtOAc:MeOH:TEA; 80:15:5); Mp=52-54° C.; $v_{max}$ (neat/cm$^{-1}$) 3943, 3692, 3054, 2987, 1560, 1421, 1265, 896; HRMS (ES) calcd. for $C_{40}H_{46}N_5O_2Cl_2$ 698.3029, found 698.3029 (matches double Cl pattern); $\delta_H$ (500 MHz, CDCl$_3$) 1.31-1.36 (4H, m, CH$_2$), 1.40-1.47 (8H, m, CH$_2$), 1.71-1.77 (4H, m, CH$_2$), 2.51 (4H, t, J=7.0 Hz, CH$_2$), 3.69 (4H, t, J=7.0 Hz, CH$_2$), 3.95 (6H, s, CH$_3$), 7.20 (2H, d, J=2.5 Hz, ArH), 7.30 (2H, dd, J=2.0, 9.5 Hz, ArH), 7.42 (2H, dd, J=2.5, 9.5 Hz, ArH), 8.00 (2H, dd, J=3.0. 9.5 Hz, ArH), 8.06 (2H, d, J=2.0 Hz, ArH) ppm; $\delta_C$ (125 MHz, CDCl$_3$) 26.8, 27.1, 31.8, 49.9, 50.7, 55.6, 99.1, 115.9, 118.0, 124.0, 124.5, 124.6, 128.4, 131.6, 134.8, 146.3, 149.0, 149.7, 156.0 ppm.

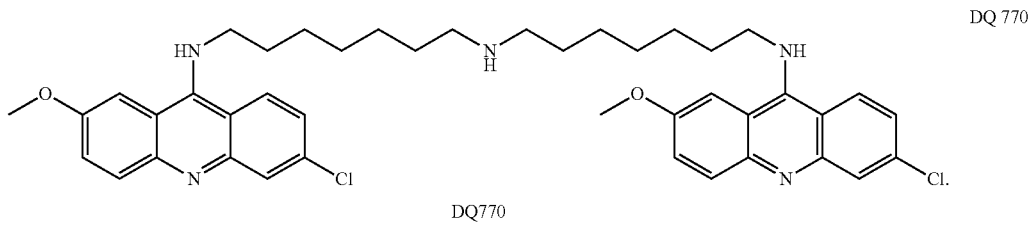

DQ770

DQ 770 was prepared by the above general procedure. Solid HCl salt was recrystallized from ethanol yielding 331 mg. This solid was converted to its free base form by dissolution in a one to one mixture of aqueous ammonium hydroxide and 25% 2-propanol/75% CHCl$_3$ yielding an orange foam (145 mg, 38%). $v_{max}$ (neat/cm$^{-1}$) 2927, 2853, 2358,23301558,1507. HRMS (ES) $C_{42}H_{49}Cl_2N_5O_2$ (calc) 725.3263, found 725.3339 matches double Cl pattern. $^1$H NMR (500 MHz, Chloroform-d) δ 8.07 (d, J=2.1 Hz, 2H, ArH), 8.00 (dd, 4H, ArH), 7.42 (dd, J=9.4, 2.7 Hz, 2H, ArH), 7.30 (dd, J=9.2, 2.1 Hz, 2H, ArH), 7.20 (d, J=2.7 Hz, 2H, ArH), 4.67 (t, J=5.9 Hz, 2H, NH), 3.96 (s, 6H), 3.68 (q, 4H, CH$_2$), 2.54 (t, J=8.1, 7.4 Hz, 4H, CH$_2$), 1.74 (p, J=7.3 Hz, 4H, CH$_2$), 1.48-1.37 (m, 9H, CH$_2$), 1.36-1.25 (m, 12H, CH$_2$). $^{13}$C NMR (126 MHz, CDCl$_3$) δ 156.04, 149.87, 148.43, 146.80, 134.85, 131.53, 128.27, 124.56, 124.53, 124.18, 117.96, 115.87, 99.30, 77.39, 55.64, 50.78, 50.14, 31.84, 30.11, 29.36, 27.37, 26.95.

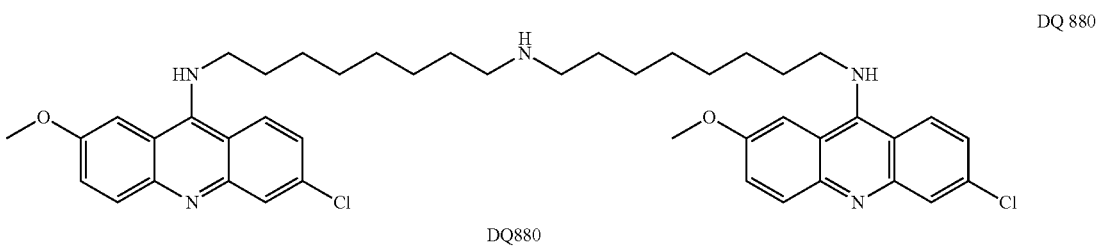

DQ880

DQ 880 was prepared by the above general procedure. The product required recrystallization from methanol, and flash column chromatography (Ethyl Acetate with 5% Triethylamine). Yielded an orange paste (125 mg, 33%). $v_{max}$ (neat/cm$^{-1}$) 3292, 2927, 2854, 2359, 2341, 1632, 1559, 1434, 1336, 924. LRMS (ES) (calc) $C_{44}H_{53}Cl_2N_5O_2$ 753.3576, found 753.50. $^1$H NMR (500 MHz, Chloroform-d) δ 8.07 (d, J=2.1 Hz, 2H, ArH), 8.04-7.97 (m, 4H, ArH), 7.42 (dd, J=9.4, 2.7 Hz, 2H, ArH), 7.34-7.24 (m, 7H, ArH), 7.21 (d, J=2.7 Hz, 2H, ArH), 4.68 (bs, 2H, N—H), 3.97 (d, J=2.7 Hz, 6H, CH$_3$), 3.69 (t, 4H, CH$_2$), 2.55 (t, J=7.2 Hz, 4H, CH$_2$), 1.78-1.71 (m, 4H, CH$_2$), 1.44 (t, J=7.0 Hz, 10H, CH$_2$), 1.36-1.23 (m, 16H, CH$_2$). $^{13}$C NMR (126 MHz, CDCl$_3$) δ 155.98, 149.72, 148.44, 146.88, 134.70, 131.64, 128.38, 124.51, 124.41, 123.98, 117.96, 115.91, 99.16, 77.29, 77.03, 76.78, 55.52, 50.77, 50.21, 50.15, 31.81, 30.19, 29.54, 29.44, 29.26, 27.40, 27.28, 27.11, 26.86.

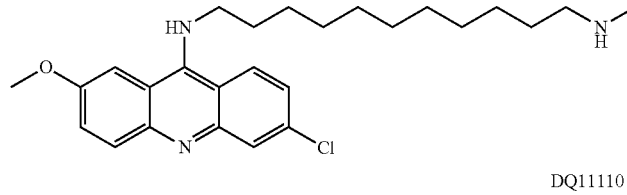
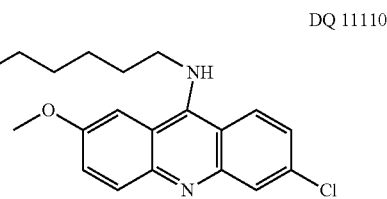

DQ 11110

DQ11110

DQ 11110 is prepared by the above general procedure except for purification. The reaction, post celite filtration is adsorbed onto silica, and purified by flash chromatography (20 mm×150 mm, 4% MeOH, 26% ethyl acetate, 1% Triethylamine, and 69% CH2Cl2) to yield an orange paste (95 mg, 30%). $C_{50}H_{65}Cl_2N_5O_2$ (calc) 837.4515, found 837.8800. $v_{max}$ (neat/cm$^{-1}$) 3302, 2925, 2852, 2360, 2341, 1631, 1561, 1518, 1465, 1434, 1235. $^1$H NMR (500 MHz, Chloroform-d and drops of Methanol-d$_3$) δ 8.08 (s, 2H), 8.06-7.98 (m, 3H), 7.43 (dd, J=9.4, 2.8 Hz, 2H), 7.31 (dd, J=9.4, 2.3 Hz, 2H), 7.25 (s, 2H), 4.92 (s, 2H), 3.99 (s, 6H), 3.73 (t, 4H), 2.66 (t, 4H), 1.78 (p, 4H, CH$_2$), 1.56 (p, 4H, CH$_2$), 1.44 (q, J=7.8 Hz, 4H), 1.39-1.22 (m, 24H, CH$_2$). $^{13}$C NMR (126 MHz, CDCl$_3$) δ 155.98, 150.01, 148.02, 146.28, 144.57, 141.08, 134.96, 128.02, 124.52, 124.46, 124.15, 117.75, 99.34, 77.27, 77.02, 76.77, 55.57, 50.80, 50.70, 49.84, 31.73, 29.43, 29.42, 29.37, 29.25, 27.29, 26.88.

General Reductive Alkylation Procedure

Method 1: Reductive Alkylation with Sodium Triacetoxyborohydride

Dimeric inhibitor is added to a flask and dissolved in CH$_2$Cl$_2$. Aqueous formaldehyde (2 equiv.) was added to the reaction and allowed to stir for 15 minutes. Once the reaction becomes homogenous, sodium triacetoxyborohydride was added (4 equiv.). Upon completion, approximately 16 hours, the reaction was diluted by half and excess sodium triacetoxyborohydride was quenched by reaction with an equal volume of 2N aqueous sodium hydroxide for 1 hour. To the chloroform solution was added 1 $M_{aq}$ HCl solution. The mixture was stirred vigorously at room temperature for 1 hour, resulting in the formation of a water soluble salt of the desired product. The mixture was allowed to settle and both layers were separated. The aqueous layer was further washed with CHCl$_3$ (2×15 mL) and combined chloroform washings were discarded at this point.

Using NH$_4$.OH, the pH of the aqueous layer was adjusted to 11, resulting in the liberation of the free base of the product. The product was extracted into a solvent mixture of CHCl$_3$ and i-propanol (4:1). These combined extracts were washed with brine and dried over Na$_2$SO$_4$.

Method 2: Eschweiler-Clarke Methylation

The dimeric inhibitor was added to a flask and dissolved in formic acid (0.5M). Aqueous formaldehyde was added to the reaction (3 equiv.), and then heated to reflux at 105C till consumption of the starting material. Upon completion, between one and three hours, the reaction was poured over water, resulting in a two fold dilution. The pH of the aqueous layer was adjusted to pH 12 by addition of aqueous ammonium hydroxide. When a precipitate formed, it was dissolved in a solution of 50:50 Methanol:CH$_2$Cl$_2$. To this solution aqueous ammonium hydroxide was added. The solution was then concentrated to near dryness, and dissolved in both CH$_2$Cl$_2$ and basic water. The organic layer was separated, and the aqueous layer was then extracted with CH$_2$Cl$_2$. The combined organic layer was then dried over sodium sulfate, and concentrated to yield the methylated inhibitor.

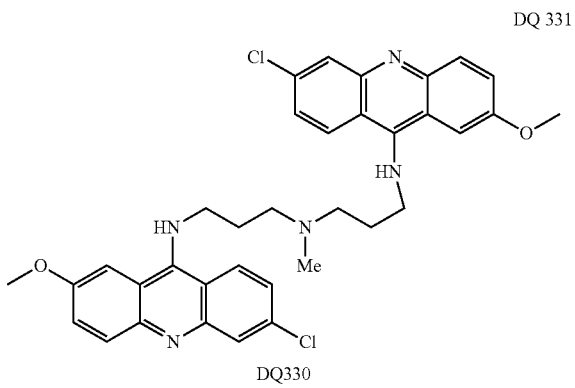

DQ 331

DQ330

DQ 331 was synthesized by general method 2. The product was isolated as an orange (21 mg, 86%). Mp=62-65° C. $v_{max}$ (neat/cm$^{-1}$) 3254, 295, 2926, 2359, 2341, 1633, 1236. $^1$H NMR (500 MHz, Chloroform-d) δ 7.99 (d, J=2.1 Hz, 2H, ArH), 7.89 (dd, J=19.6, 9.3 Hz, 4H, ArH), 7.32 (dd, J=9.4, 2.7 Hz, 2H, ArH), 7.15-7.09 (m, 4H, ArH), 3.78 (s, 6H, CH$_3$), 3.76 (t, J=6.4 Hz, 4H, CH$_2$), 2.56 (t, J=6.3 Hz, 4H, CH$_2$), 2.35 (s, 3H, CH$_3$), 1.88 (p, J=6.4 Hz, 4H, CH$_2$). $^{13}$C NMR (126 MHz, CDCl$_3$) δ 155.71, 149.84, 148.64, 146.92, 134.78, 131.59, 128.38, 124.21, 124.13, 123.93, 117.51, 115.37, 100.20, 77.44, 77.39, 77.19, 76.94, 57.06, 55.61, 50.74, 50.10, 42.91, 28.34.

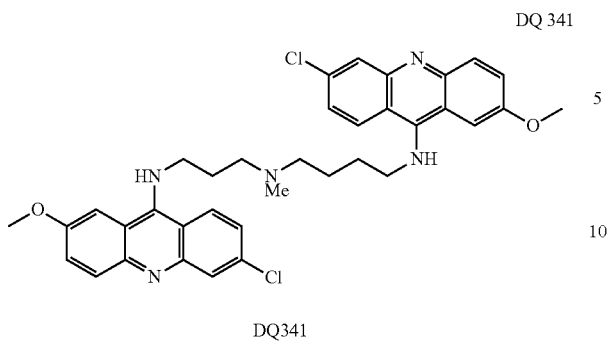

DQ341

DQ 341 was synthesized according to general method 2. The product as a dark-red solid (34.0 mg, 94% yield). Mp=61-66° C.; $v_{max}$ (neat/cm$^{-1}$) 3434, 1653, 1213, 929; HRMS (ES) calcd for $C_{36}H_{38}Cl_2N_5O_2$ 642.2403, found 642.2398 (matches double Cl pattern); $\delta_H$ (500 MHz, CD$_2$Cl$_2$) 1.61-1.67 (4H, m, CH$_2$), 1.84 (2H, pent, J=5.5 Hz, CH$_2$), 2.32 (3H, s, CH$_3$), 2.44 (2H, t, J=7.0 Hz, CH$_2$), 2.57 (2H, t, J=7.0 Hz, CH$_2$), 3.67 (2H, t, J=6.5 Hz, CH$_2$), 3.83 (3H, s, CH$_3$), 3.86 (3H, s, CH$_3$), 3.89 (2H, t, J=4.5 Hz, CH$_2$), 7.07-7.14 (4H, m, ArH, NH), 7.24 (1H, d, J=2.5 Hz, ArH), 7.30-7.34 (3H, m, ArH), 7.86 (2H, dd, J=3.5, 9.5 Hz, ArH), 7.92 (3H, d, J=9.5 Hz, ArH), 8.02 (1H, d, J=9.5 Hz, ArH) ppm; $\delta_C$ (125 MHz, CD$_2$Cl$_2$) 25.1, 27.7, 30.4, 43.0, 51.0, 51.7, 56.0, 56.1, 57.8, 58.7, 99.7, 101.3, 115.0, 116.4, 117.2, 118.4, 123.5, 124.0, 124.7 (2C), 124.8, 125.6, 128.4, 128.7, 131.7, 132.0, 134.9 (2C), 148.8, 149.2 (2C), 150.0, 150.9, 155.8, 156.5

DQ441

DQ 441 was synthesized by general method 1. Filtration followed by solvent evaporation afforded the product as a red solid (0.13 g, 83% yield). R$_f$=0.55 (EtOAc:MeOH:TEA; 80:15:5); Mp=60-62° C.; $v_{max}$ (neat/cm$^{-1}$) 3054, 2987, 1559, 1422, 1265, 896; HRMS (ES) calcd for $C_{37}H_{40}N_5O_2Cl_2$ 656.2559, found 656.2565; $\delta_H$ (500 MHz, CDCl$_3$) 1.52-1.58 (4H, m, CH$_2$), 1.67-1.83 (4H, m, CH$_2$), 2.15 (3H, s, CH$_3$), 2.30 (4H, t, J=7.0 Hz, CH$_2$), 3.68 (4H, t, J=6.5 Hz, CH$_2$), 3.91 (6H, s, CH$_3$), 5.06 (2H, s (br), NH), 7.22 (2H, d, J=2.5 Hz, ArH), 7.24 (1H, d, J=2.0 Hz, ArH), 7.26 (1H, s (br), ArH), 7.39 (2H, dd, J=2.5, 9.5 Hz, ArH), 7.97-7.99 (4H, m, ArH), 8.04 (2H, d, J=2.0 Hz, ArH) ppm; $\delta_C$ (125 MHz, CDCl$_3$) 24.6, 29.6, 42.2, 50.5, 55.6, 57.0, 99.6, 115.8, 117.9, 124.1, 124.2, 124.4, 128.3, 131.6, 134.7, 146.8, 148.4, 149.9, 155.9 ppm.

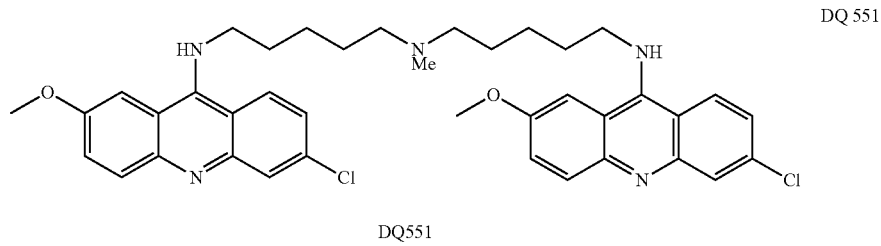

DQ551

DQ 551 was synthesized by general method 1. The product was isolated as a red foam (0.30 g, 50% yield). Mp=48-52° C.; $v_{max}$ (neat/cm$^{-1}$) 3944, 3692, 3054, 2987, 1631, 1560, 1422, 1262, 896; HRMS (ES) calcd for $C_{39}H_{44}N_5O_2Cl_2$ 684.2872, found 684.2897 (matches double Cl pattern); $\delta_H$ (500 MHz, CD$_2$Cl$_3$) 1.45 (8H, s (br), CH$_2$), 1.78 (4H, s (br), CH$_2$), 2.12 (3H, s, CH$_3$), 2.26 (4H, s (br), CH$_2$), 3.73 (4H, t, J=6.5 Hz, CH$_2$), 3.98 (6H, s, CH$_3$), 7.31-7.34 (4H, m, ArH), 7.41-7.45 (2H, m, ArH), 7.96-7.98 (2H, m, ArH), 8.03 (2H, s, ArH), 8.10 (2H, d, J=8.0 Hz, ArH) ppm; $\delta_C$ (125 MHz, CD$_2$Cl$_3$) 24.7, 26.9, 31.5, 41.8, 50.6, 55.5, 57.4, 99.3, 115.7, 117.8, 124.0, 124.3, 124.5, 128.0, 131.4, 134.4, 146.7, 148.4, 149.8, 155.9 ppm.

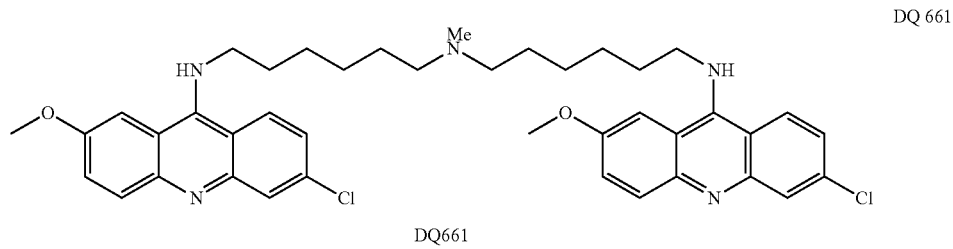

DQ661

DQ 661 was synthesized according to general method 2. The product was isolated as a brown orange solid/foam (2.98 g, 91%). HRMS (ES) calcd for $C_{41}H_{48}N_5O_2Cl_2$ 712.3185, found 712.3164. $v_{max}$ (neat/cm$^{-1}$) 3293, 2934, 2854, 1687, 1657, 1235, 925, 829 $^1$H NMR (500 MHz, Chloroform-d) δ 8.08 (d, J=2.1 Hz, 2H, ArH), 8.02 (t, J=8.9 Hz, 4H, ArH), 7.43 (dd, J=9.4, 2.7 Hz, 2H, ArH), 7.32 (dd, J=9.3, 2.1 Hz, 1H, ArH), 7.23 (d, J=2.7 Hz, 2H, ArH), 4.75 (s, 2H, NH), 3.97 (d, J=2.9 Hz, 8H, CH$_3$), 3.70 (s, 4H, CH$_2$), 2.25 (t, J=7.6 Hz, 4H, CH$_2$), 2.17 (s, 3H, CH$_3$), 1.75 (p, J=7.5 Hz, 4H, CH$_2$), 1.43 (d, J=7.6 Hz, 14H, CH$_2$), 1.32 (s, 6H, CH$_2$). $^{13}$C NMR (126 MHz, CDCl$_3$) δ 155.66, 149.78, 147.98, 146.18, 134.67, 130.80, 127.55, 124.36, 124.28, 123.95, 117.44, 115.25, 99.29, 77.44, 77.19, 76.94, 74.66, 57.59, 55.43, 50.31, 50.27, 49.72, 42.15, 31.57, 31.50, 29.72, 27.20, 27.07, 26.97, 26.79, 26.72.

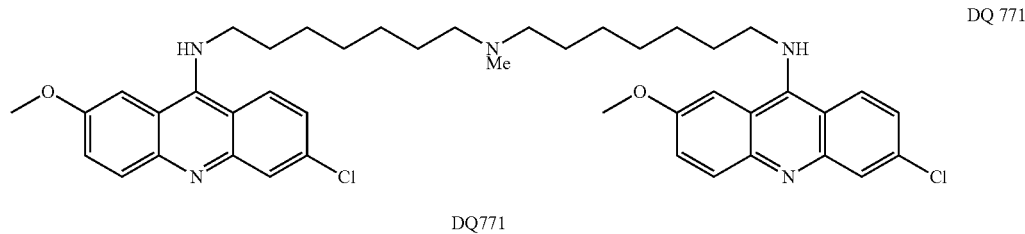

DQ771

DQ 771 was synthesized according to general method 2. The product was isolated as a black/orange solid film. (31 mg, 74%). $v_{max}$ (neat/cm$^{-1}$) 3302, 2930, 2854, 2793, 2359, 2341, 1632, 1559, 1236. HRMS (ES) $C_{43}H_{51}Cl_2N_5O_2$ (calc) 739.3420, found 739.3522. $^1$H NMR (500 MHz, Chloroform-d) δ 8.05 (s, 2H, ArH), 8.02-7.95 (m, 4H, ArH), 7.40 (dd, J=9.4, 2.7 Hz, 2H, ArH), 7.28 (dd, 2H, ArH), 7.22-7.18 (m, 2H, ArH), 4.76 (d, J=20.5 Hz, 2H, NH), 3.95 (s, 6H, CH$_3$), 3.67 (t, J=7.3 Hz, 4H, CH$_2$), 2.28-2.23 (m, 3H, CH$_2$), 2.16 (s, 1H, CH$_3$), 1.73 (p, J=7.2 Hz, 5H, CH$_2$), 1.41 (p, J=6.9 Hz, 9H, CH$_2$), 1.36-1.20 (m, 16H, CH$_2$). $^{13}$C NMR (126 MHz, CDCl$_3$) δ 155.99, 149.77, 136.79, 134.77, 131.49, 128.23, 124.50, 124.43, 124.01, 117.91, 99.22, 77.28, 77.23, 77.03, 76.77, 57.79, 55.53, 53.42, 50.72, 42.27, 31.75, 29.29, 27.44, 27.21, 26.90.

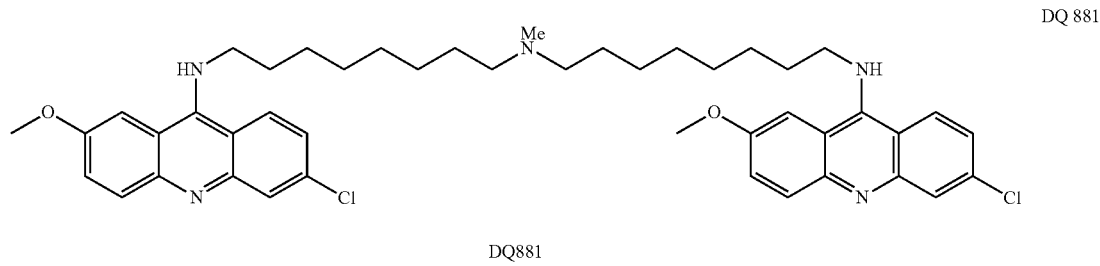

DQ881

DQ 881 was synthesized according to general method 2. The product was isolated as a red orange film (15 mg, 72%). $v_{max}$ (neat/cm$^{-1}$) 2930, 2854, 2359, 1632, 1559, 1236. HRMS (ES) $C_{45}H_{55}Cl_2N_5O_2$ (calc) 767.3733, found 767.3819. 1H NMR (500 MHz, Chloroform-d) δ 8.06 (s, 2H, ArH), 8.03-7.97 (m, 4H, ArH), 7.42 (dd, J=9.4, 2.9 Hz, 2H, ArH), 7.30 (dd, J=9.2, 3.4, 2.1 Hz, 2H, ArH), 7.21 (d, J=2.8 Hz, 2H, ArH), 4.72 (s, 2H, NH), 3.96 (d, J=4.6 Hz, 6H, CH$_3$), 3.68 (t, J=7.1 Hz, 4H, CH$_2$), 2.27 (dd, J=8.9, 6.2 Hz, 4H, CH$_2$), 2.18 (d, J=3.5 Hz, 3H, CH$_3$), 1.73 (p, J=7.5 Hz, 4H, CH$_2$), 1.49-1.19 (m, 24H, CH$_2$). $^{13}$C NMR (126 MHz, CDCl$_3$) δ 156.17, 149.93, 148.57, 146.99, 134.91, 131.77, 128.51, 124.71, 124.59, 124.15, 118.13, 116.08, 99.36, 77.76, 77.44, 77.39, 77.19, 76.94, 58.06, 57.96, 55.71, 50.95, 42.49, 31.98, 29.66, 29.64, 29.50, 29.47, 28.91, 28.80, 27.63, 27.47, 27.44, 27.08, 27.05, 25.49, 17.30.

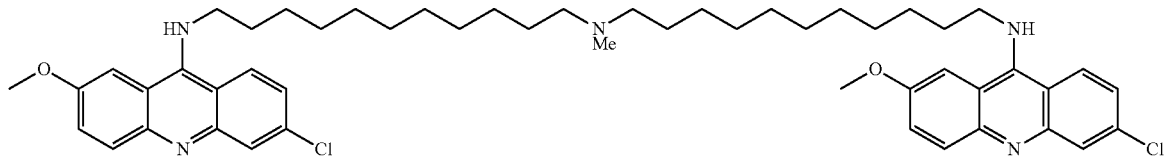

DQ11111

DQ 11111 was synthesized according to general method 2. The product was isolated as a red orange paste (53 mg, 75%). $v_{max}$ (neat/cm$^{-1}$) 2925, 2852, 2793, 1631, 1465, 1236. MS (ES) $C_{51}H_{67}Cl_2N_5O_2$ (Calc) 851.4672, found 851.6714. $^1$H NMR (500 MHz, Chloroform-d) δ 8.04 (d, J=2.1 Hz, 2H, ArH), 7.98 (dd, J=9.4, 2.3 Hz, 4H, ArH), 7.40 (dd, J=9.4, 2.7 Hz, 2H, ArH), 7.30-7.26 (m, 4H, ArH), 7.18 (d, J=2.7 Hz, 2H, ArH), 3.94 (s, 6H, CH$_3$), 3.66 (t, J=7.2 Hz, 4H, CH$_2$), 2.31-2.24 (m, 4H, CH$_2$), 2.19 (s, 3H, CH$_3$), 1.72 (p, J=7.3 Hz, 4H, CH$_2$), 1.46-1.36 (m, 8H, CH$_2$), 1.34-1.15 (m, 30H, CH$_2$). $^{13}$C NMR (126 MHz, CDCl$_3$) δ 156.09, 149.90, 148.54, 146.95, 134.85, 131.67, 128.41, 124.59, 124.56, 124.16, 118.03, 115.97, 99.31, 77.38, 58.13, 55.65, 53.57, 50.90, 45.69, 42.52, 31.95, 29.76, 29.70, 29.64, 29.61, 29.47, 27.77, 27.52, 27.06

Biology

Summary

Aberrant autophagic-lysosomal activity and constitutive PI3K/AKT pathway signaling are critical features of advanced cancers converging on mTORC1, which requires lysosomal localization for full functionality. Clinical trials demonstrate that inhibition of the lysosome with the 4-aminoquinoline antimalarial hydroxychloroquine (HCQ) holds promise in specific cancers, but limited potency of existing chloroquines (CQs) and an unclear mechanism of action represent significant hurdles to the development of effective chemotherapeutic agents. We report a medicinal chemistry-driven screening effort that identifies a potent small molecule lysosomal inhibitor, DQ661, which concurrently blocks autophagy and mTORC1 signaling in vivo through lysosome membrane permeabilization (LMP). DQ661 promotes displacement of mTORC1 from the lysosomal surface by disrupting RaGTPase/Ragulator/lysosome interactions. Interestingly, DQ661-induced LMP does not displace mTORC1 in TSC2-deficient MEFs, suggesting Rheb function is less sensitive to LMP relative to RaGTPase/Ragulator function. DQ661 possesses significant single-agent activity in melanoma xenograft models and potentiates the effects of chemotherapy in a radiation/CTLA4-resistant pancreatic cancer syngeneic model. Our study provides a novel strategy to pharmacologically inhibit mTORC1 activity via disrupting RaGTPase/Ragulator/lysosome interactions, which outcompetes anti-cancer potency of both allosteric and selective ATP-competitive mTOR inhibitors.

Materials and Methods:

Cell Culture and Reagents.

Melanoma cell lines A375P, SKMEL5, 1205Lu, WM983B, A375P mCherry-GFP-LC3 and pancreatic cancer cell lines PANC1 and CAPAN1 were cultured in RPMI-1640 (Invitrogen) supplemented with 10% fetal bovine serum (Hyclone) in the presence of 5% CO$_2$ at 37° C. The PDA.4662 cell line was established from single-cell suspensions of PDA tissue from Kras$^{LSL-G12D/+}$, p53$^{LSL-R172H/+}$, Pdx1-Cre mice as previously described (Ref from Vonderheides paper). The resistant-G43 cell line was established from single cell suspension of PDA.4662 cells that developed resistance to combination radiation/CTLA-4 therapy in mice (Ref Vonderheides paper). PDA.4662 and G43 cells were cultured in DMEM+ GlutaMAX (Gibco, Life Technologies) supplemented with 10% FBS, 1% L-glutamine and 1% gentamycin. TSC2 MEFs were a kind gift from Celeste Simon Lab. Rapamycin and Bafilomycin-A1 was purchased from Sigma-Aldrich. HCQ, CQ and QN were purchased from Spectrum Chemicals. Torin, PLX4720 and GSK1120212 were purchased from Selleck Chemicals.

Electron Microscopy.

Electron microscopy was performed as previously described (Ref).

Immunoblotting.

Immunoblotting was performed on whole-cell lysates (ref), lysosomal extracts (ref) and nuclear extracts as previously described (ref). Cell Signaling Technology antibodies used were as follows: β-actin, 4E-BP1, phospho-4E-BP1 S65, S6K, phospho-S6K T389, S6, phospho-S6 S240_S244, LAMTOR (p18), RagA, RagC, Cathepsin D, and phospho-H2AX. LAMP2 was purchased from Santa Cruz. LC3B antibody was generated as described previously (ref JCI paper).

MTT Assay and Clonogenic Assay.

For MTT assays, cells were plated in 96-well plates (2,000 cells/well), allowed to adhere overnight, and subsequently treated in triplicate for 72 hours. MTT reagent (Roche) was applied, cells were solubilized and absorbance was read at 570 nm, with background subtraction at 690 nm. The clonogenic assay was performed as previously described. Briefly, cells were suspended in appropriate culture media, and plated in 6-well plates (2×10$^3$ cells/well). Medium was changed and drug treatment refreshed every 3-4 days for 2 weeks. Cells were subsequently stained with crystal violet and quantified.

In Vivo Mouse Studies.

Five to seven-week old NOD-scid gamma (NSG) mice (Jackson Laboratory) were used for xenograft studies with the 1205Lu melanoma cell line. Tumor generation, tumor measurement and tumor harvesting performed as previously described (ref). For the pancreatic cancer model, five to seven-week old C57BL/6 mice (Jackson Laboratory) and maintained under pathogen-free conditions. 2×106 G43 cells were subcutaneously injected with an equal volume of matrigel (BD) over the right flank (how do I say on the square of their backs?) and tumors became palpable after 5-6 days. Mice were enrolled on day 6 and given Gemcitabine (120 mg/kg, i.p.). DQ661 (4 mg/kg, i.p.) was given on days 7, 8, 12, 13, 17 and 18. Perpendicular tumor diameters were measured sing electronic calipers and volume was calculated leveraging the formula L×W$^2$×0.5, where L is the longest dimension and W is the perpendicular dimension. All animal experiments were performed in accordance to the protocols approved by the Institute of Animal Care and Use Committee of the University of Pennsylvania.

Results

Dimeric Quinacrine has Superior Anticancer Efficacy Amongst Dimeric Anti-Malarials.

Lys05 is 10-fold more potent than HCQ in in vitro autophagy assays, however it is cytotoxic only at micromolar concentrations in most cancer cells (McAfee et al., 2012). In an attempt to improve in vivo activity, we designed a series of second-generation analogs of Lys05 to test the effect of changing each of the separate parts of the Lys05 structure on lysosomal inhibition and cytotoxicity. Replacement of the linker of Lys05 with the commercially available linker spermidine and exchanging the aromatic rings of Lys05 from CQ to the antimalarial-based heterocyclic systems primaquine (PQ), mefloquine (MQ) and quinacrine (QC) was interrogated (FIG. 1A). The dimeric antimalarial compounds were named DC (dimeric chloroquine), DM (dimeric mefloquine), DP (dimeric primaquine) and DQ (dimeric quinacrine). The dimeric compounds were named followed by three digits (m, n, r) where m signifies the number of carbons to the left of the central nitrogen, the n signifies the number of carbons on the right of the central nitrogen and the r signifies if the central nitrogen is methylated (1) or not (0). A375P (melanoma) cells treated with CQ, DC340, MQ, DM340, PQ, DP340, QC and DQ340 in MTT assays revealed DQ has superior anti-proliferative activity with low nanomolar IC50 relative to its monomeric counterpart (QC) amongst the other tested dimeric antimalarials (FIG. 1B). We generated a focused library of DQs with triamine linkers of increasing length ranging from lengths of two to eleven carbons between the QC heterocycle and the central nitrogen of the triamine linker. Both secondary and tertiary amine derivatives of each analog were generated to determine the role of central nitrogen alkylation on biological activity. A375P and PANC1 (pancreatic cancer) cells were treated with CQ, Lys05, QC and the DQ library, establishing the increase in anti-proliferative potency of DQs relative to monomeric QC. Interestingly, monomeric quinacrine had similar activity to our original lead dimeric-chloroquine compound Lys05. We observed a clear relationship between linker length and potency amongst the DQs. The dimeric quinacrine DQ221, with the same N-methyl-bisethylenetriamine linker as Lys05, possessed the same activity as monomeric QC. We postulate that this surprising result (the bisaminoquinoline Lys05 with the same linker showed considerably greater potency than monomeric CQ) is due to steric hindrance between the two quinacrine heterocycles, as acridines are 50% larger than quinoline rings. Increasing the distance between the two quinacrine heterocycles by two methylenes (DQ330) led to a significant increase in anti-proliferative potency (FIGS. 1C and 1D). DQs with propyl (three-carbon) and hexyl (six-carbon)-based triamine linkers possess significant activity, which decreases when triamines based on heptyl (seven-carbon) and larger alkyl chains were used (FIGS. 1C and 1D). The potency of these longer linked compounds began to return to that of monomeric quinacrine, establishing that the optimal geometry between the two quinacrine moieties requires a triamine linker with greater than two-carbon and less than seven-carbon atoms between the nitrogen atoms in these triamine systems. Spautin-1, which promotes degradation of Vps34 PI3 kinase complexes, and SBI-0206965, an ULK1 inhibitor, are two recently described proximal autophagy inhibitors (Egan et al., 2015; Liu et al., 2011). When tested in parallel to the DQs. Spautin-1 and SBI-0206965 have $IC_{50}$ values greater than 15 uM in both A375P and PANC1 cells (FIGS. 1C and 1D). Interestingly, Spautin-1 and SBI-0206965 did not have significantly increased anti-cancer activity relative to monomeric chloroquine or monomeric quinacrine, suggesting that strategies for distal inhibition of autophagy may be superior to proximal autophagy inhibition approaches. DQs with linker lengths greater than 4 carbons were also observed to have significantly greater durability at doses as low as 30 nM relative to monomeric quinacrine and DQ221, as seen in long-term colony formation assays of PANC1 cells. DQs also possessed cytotoxic effects as seen by annexin V binding flow cytometry assays. PANC1 cells were treated with the panel of DQs (3 uM) as well as Spautin-1 (3 μM) and SBI-0206965 (3 μM) for 24 hours. Spautin-1 and SBI-0206965 did not induce significant levels of apoptosis, whereas the majority of DQs induced significantly greater levels of apoptosis relative to monomeric quinacrine, and the amount of apoptosis induced appeared to directly correlate with increasing linker length (FIG. 1E).

Central Nitrogen Alkylation State (2 vs 3) Serves as a Homing Signal, Determining Subcellular Localization of DQs.

Figure 2:
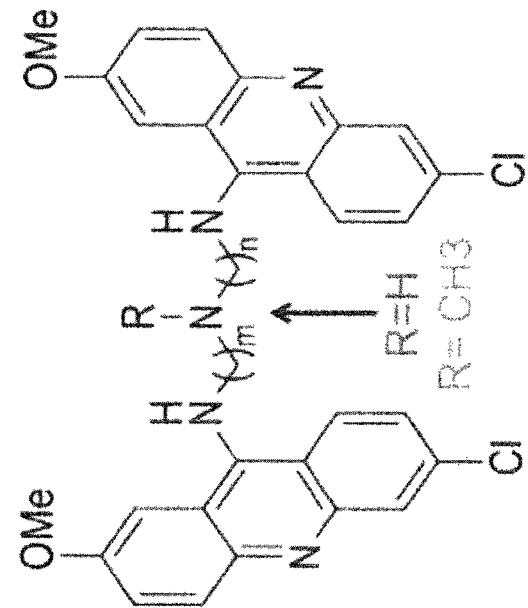
FIG. 2: Central nitrogen methylation status dictates effect upon autophagy, induction versus inhibition. (A) C8161 melanoma cells were treated with the DQ compound library (4 hr, 3 µM) and lysate was subsequently immunoblotted for LC3B and Actin. Quantification of LC3II/I ratios standardized to control are shown below corresponding blot. DQ's with central nitrogen methylation are colored orange, whereas unmethylated compounds are colored purple. (B) A bafilomycin clamp was performed for the DQ compound library to determine effects on autophagic flux. A375P cells were treated with the DQ compound library (4 hr, 3 µM) in the presence or absence of bafilomycin (100 nM). Lysate was subsequently immunoblotted for LC3B and Actin. Quantification of LC3II/I ratios standardized to control are shown below corresponding blots. (C) Fluorimetry was performed on the DQs DQ550, DQ551, DQ660 and DQ661. (D) PANC1 cells were treated with DQ550, DQ551, DQ660 or DQ661 (6 hr, 3 µM) and inherent fluorescence of the DQs was imaged with fluorescent microscopy in the GFP, RFP and Brightfield channels. Arrows indicate red perinuclear fluorescence. (E) PANC1 cells were treated with DQ550, DQ551, DQ660 or DQ661 (6 hr, 3 µM) and co-stained with LysoTracker far-red (shown green). Cells were imaged with fluorescent microscopy and arrows indicate co-localization of DQ compound (red) with lysotracker (green). (F) A375P cells were treated with DQ661 (6 hr, 3 µM) in the presence or absence of bafilomycin (100 nM). Cells were subsequently stained with LysoTracker far-red (shown red), DAPI (blue) and imaged using fluorescence microscopy. The arrows point out either nuclear or lysosomal localization of DQ661 (shown green), as depicted in the image accordingly. (G) Long-term colony formation assays were performed with ATG5+/+ and ATG5−/− MEFs treated with DQ661 (2 weeks, 10-300 nM). Cells were subsequently stained with crystal violet and imaged.
Figure 2:
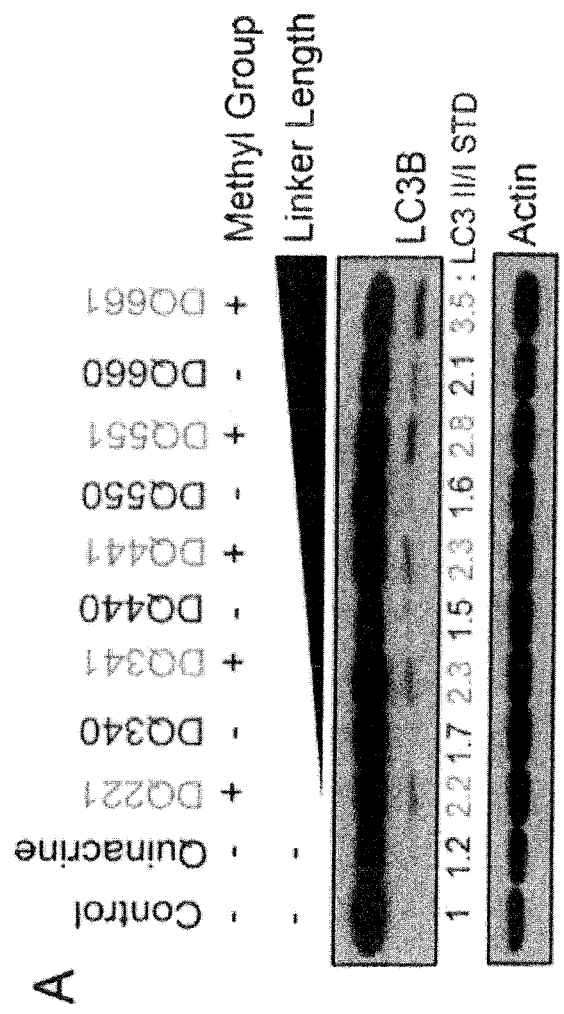
Figure 2:
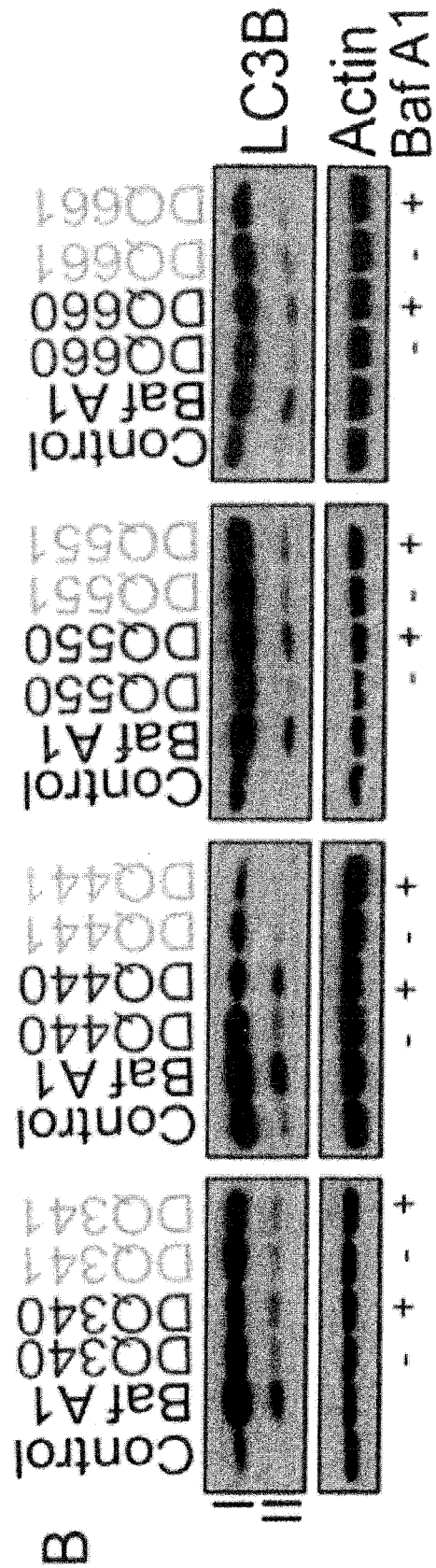
Figure 2:
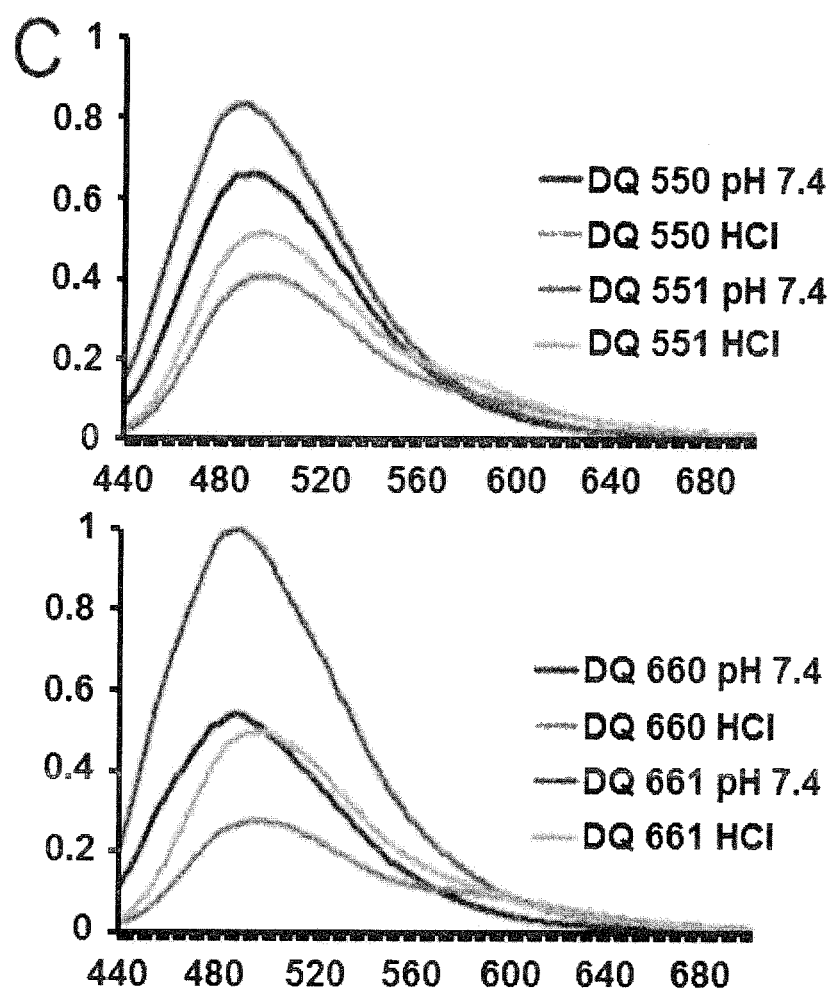
Figure 2:
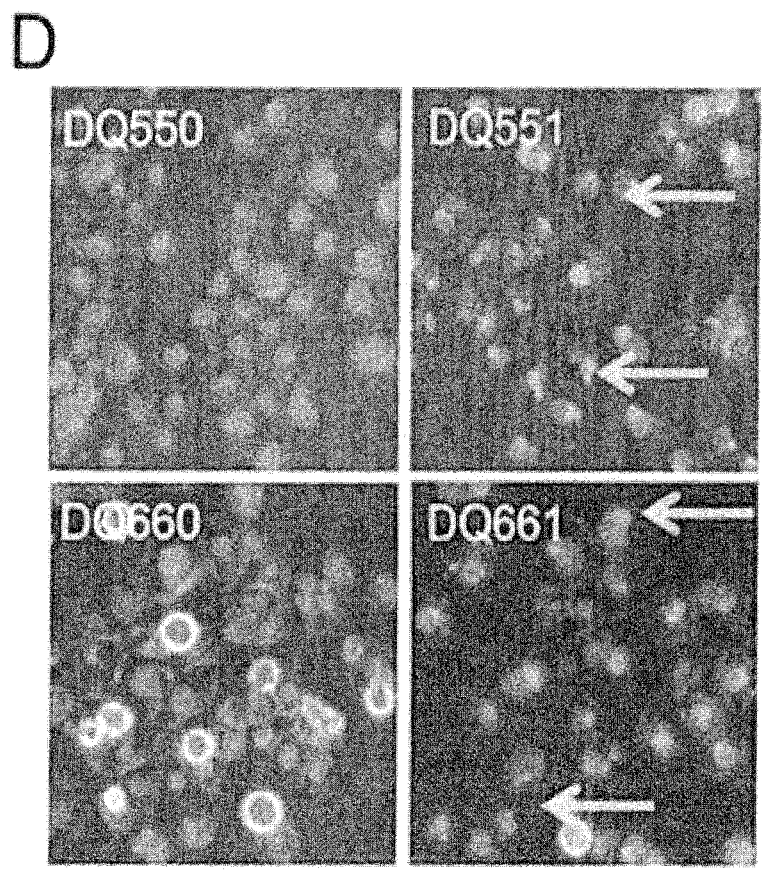
Figure 2:
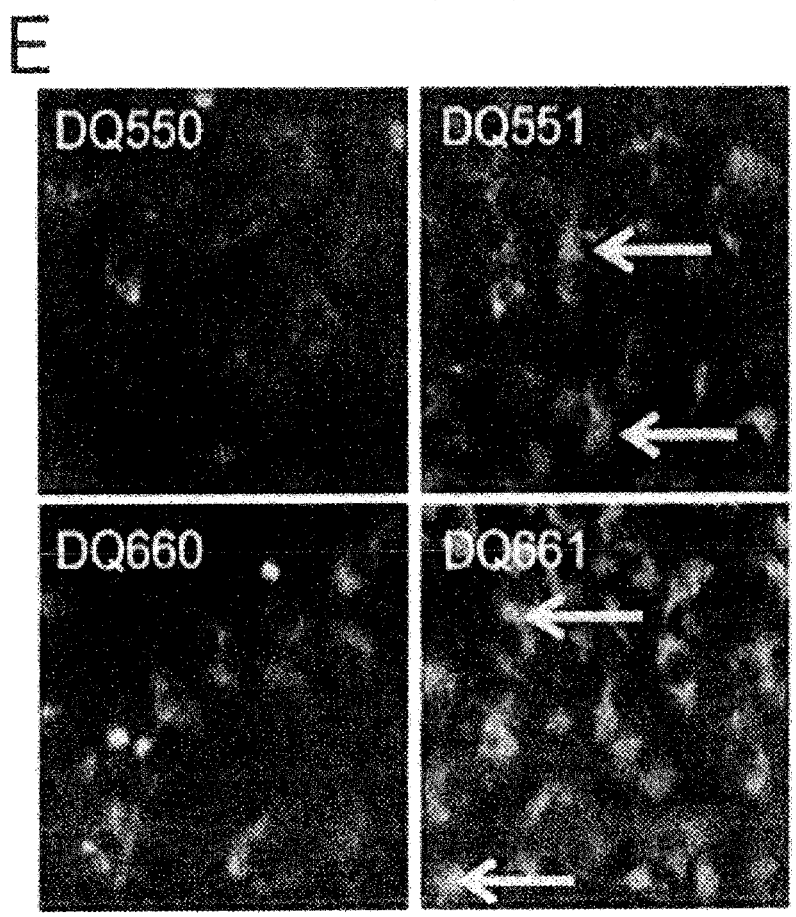
Figure 2:
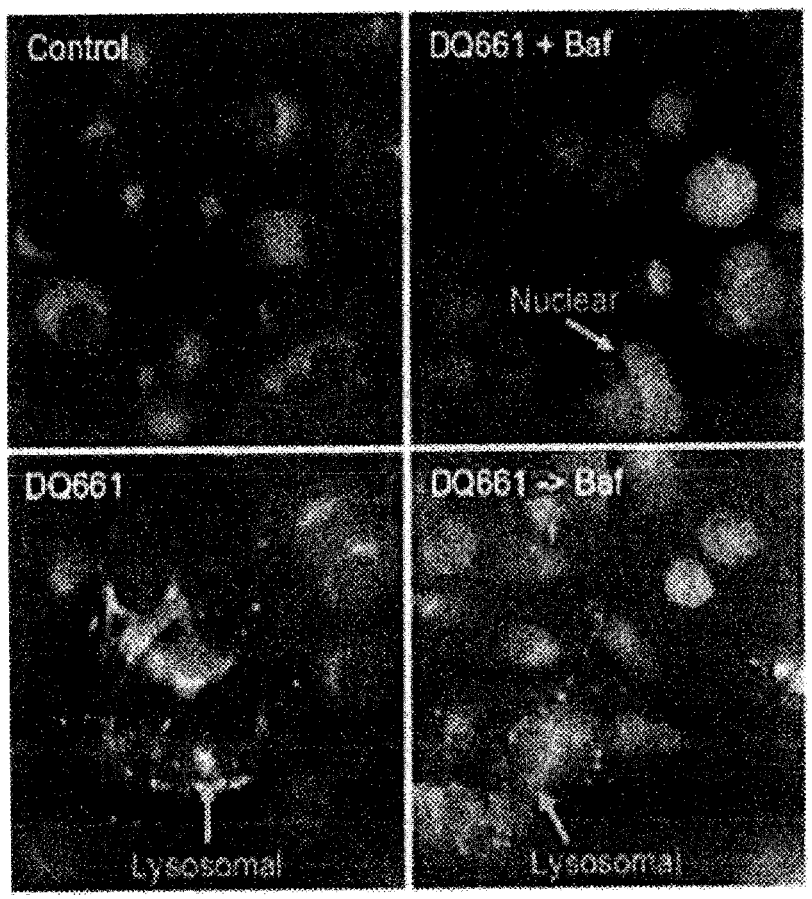
Figure 2:
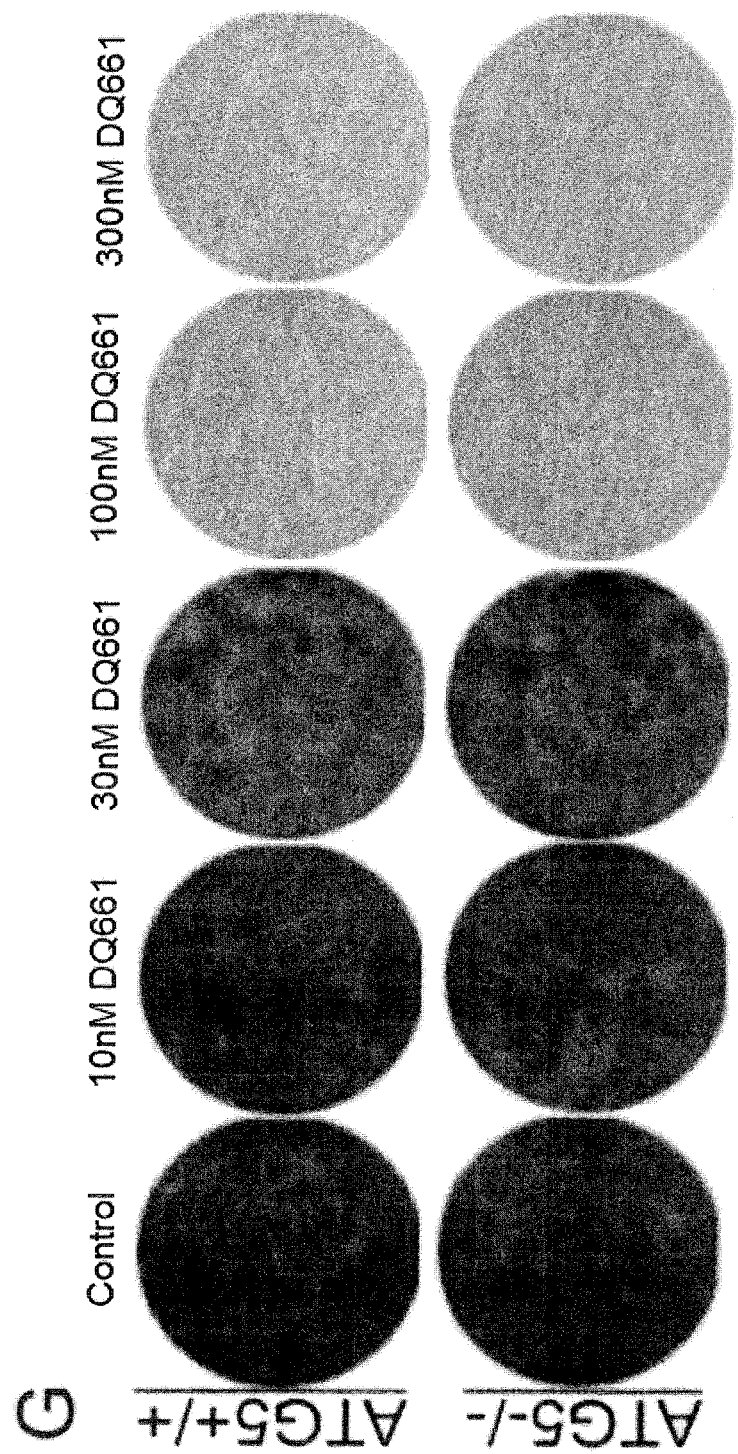

Quinacrine is known to bind to DNA in the nucleus and accumulate in the lysosome (Jennings and Ridler, 1983). Therefore it was important to establish the specificity of these dimeric quinacrines as lysosomal autophagy inhibitors. Changes in autophagosome levels were first interrogated by measuring LC3 protein levels by Western blotting. There was a correlation with increasing linker length and increasing LC3II/LC3I levels. (FIG. 2A). Interestingly, there was also a relationship between central nitrogen methylation status and the degree of LC3II accumulation, in which compounds with central nitrogen methylation (DQXX1) had significantly greater LC3II/LC3I accumulation relative to their unmethylated (DQXX0) counterparts. Due to the inherent fluorescence of quinacrine, spectral overlap was observed with mCherry-eGFP-LC3 expressing cells, limiting the use of this approach to characterize autophagic flux. The effects of these compounds on autophagic flux were therefore determined by a classical bafilomycin clamp experiment (Klionsky and Zuckerbraun, 2012). 451Lu (melanoma) cells were treated with monomeric quinacrine (3 μM) and the panel of DQ compounds (DQ221-661) in the presence or absence of bafilomycin-A1 for 24 hours. Quinacrine treatment resulted in a further increase in the LC3II/LC3I ratio in bafilomycin-treated cells compared with control cells, confirming that quinacrine induces autophagic flux, as previously reported. All DQs without a central nitrogen methylation (DQXX0) also resulted in an induction of autophagic activity, as seen by an increase in the LC3II/LC3I ratio of bafilomycin-treated cells compared with control cells. Surprisingly, every DQ with a central nitrogen methylation (DQXX1) did not demonstrate an increase in LC3II/LC3I ratio in bafilomycin-treated cells compared to control, confirming that each of the tertiary amines (DQ221, DQ341, DQ441, DQ551 and DQ661) are autophagy inhibitors (FIG. 2B).

The inherent fluorescence of DQ's was utilized to study their subcellular localization. We observed the most potent longer linked DQs fluoresced in both the red and green channels, at both neutral (pH=7) and acidic (pH=4) conditions (FIG. 2C). Acidic conditions decreased the 495 nm peak (green) but had minimal effects on fluorescence at 600 nm. These changes with acidic pH were consistent between DQs with central nitrogen methylation (DQ551 and DQ661) and DQ's without central nitrogen methylation (DQ550, DQ660). This characterization of fluorescent properties in acidic and neutral conditions indicated that red fluorescence could be used to assess subcellular localization into acidic compartments such as the lysosome better than green fluorescence. PANC1 and A375P cells were treated with the most active longer linked DQs (DQ550, DQ551, DQ660, DQ661) and images were taken using fluorescent microscopy in Brightfield, green and red channels. Each unmethylated DQ (DQ550, DQ660) possessed strong green fluorescence in the nuclear compartment with little to no detectable red fluorescence, whereas each methylated DQ (DQ551, DQ661) possessed strong red fluorescence in the perinuclear compartment where lysosomes reside as well as green fluorescence in the nuclear compartment (FIG. 2D). The red fluorescence of methylated DQs (DQ551, DQ661) localized to the lysosome, as further demonstrated in PANC1 and A375P cells treated with DQ550, DQ551, DQ660 or DQ661 and co-stained with lysotracker far red (FIG. 2E). Similar experiments using Mitotracker determined that these longer linkered centrally methylated DQs did not significantly co-localize with mitochondria, except in the perinuclear, lysosomal compartment in cases where engulfed mitochondria are being degraded through mitophagy. Chloroquine and quinacrine have been suggested to localize to the acidic lysosomal compartment due to the compounds being weak bases. The chemical-physical properties of the DQs are provided in table 1. The pKA of the compounds do not vary significantly with linker length or central nitrogen methylation, suggesting that factors other than the inherent basicity of the compounds dictate subcellular localization.

To determine whether lysosomal acidity is required for DQ661 to localize to the lysosome, A375P cells were treated with DQ661 in the presence or absence of bafilomycin-A1, a putative vacuolar ATPase inhibitor. Cells were co-stained with Lysotracker and Dapi. Cells treated with only DQ661 displayed lysosomal localization of DQ661 (FIG. 2F). Concurrent treatment with DQ661 and bafilomycin-A1 displaced DQ661 from the lysosomal compartment and into the nucleus. Bafilomycin-A1 treatment following pre-treatment with DQ661 did not displace DQ661 from the lysosomal compartment to the same degree, suggesting once DQ661 is localized to the lysosomal compartment, deacidification of the lysosome does not effect displacement of the drug (FIG. 2F). DQ661 induced equal cytotoxicity in ATG5 WT and ATG5-null MEFs, indicating that its cytotoxicity is not dependent on functional upstream canonical autophagy (FIG. 2G).

DQs Cause Either Significant DNA Damage or Lysosomal Membrane Permeabilization Depending on the Central Nitrogen Alkylation State (2 vs 3).

Figure 3:
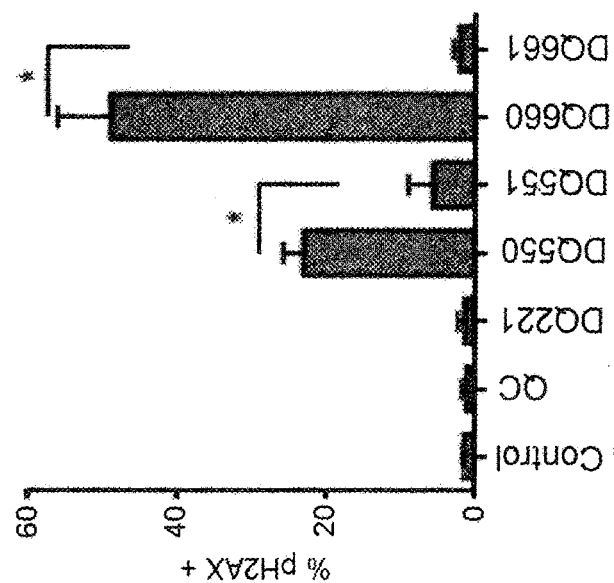
FIG. 3: Central nitrogen methylation status dictates DNA damage versus lysosomal membrane permeability. (A) A375P cells were treated with QC, DQ221, DQ550, DQ551, DQ660 or DQ661 (6 hr, 3 µM) and subsequently stained for phospho-H2AX (red) and DAPI (blue). Cells were imaged with fluorescent microscopy, phospho-H2AX+ cells were scored using ImageJ software analysis and quantified to the right. (B) A375P cells were treated identical to the conditions in (A), with the addition of the positive control LLoMe (3 hr, 2 mM). Cells were subsequently stained with galectin-3 and imaged with fluorescent microscopy. The formation of galectin-3 punctae, which signify lysosomal membrane permeabilization, are pointed out with yellow arrows.
Figure 3:
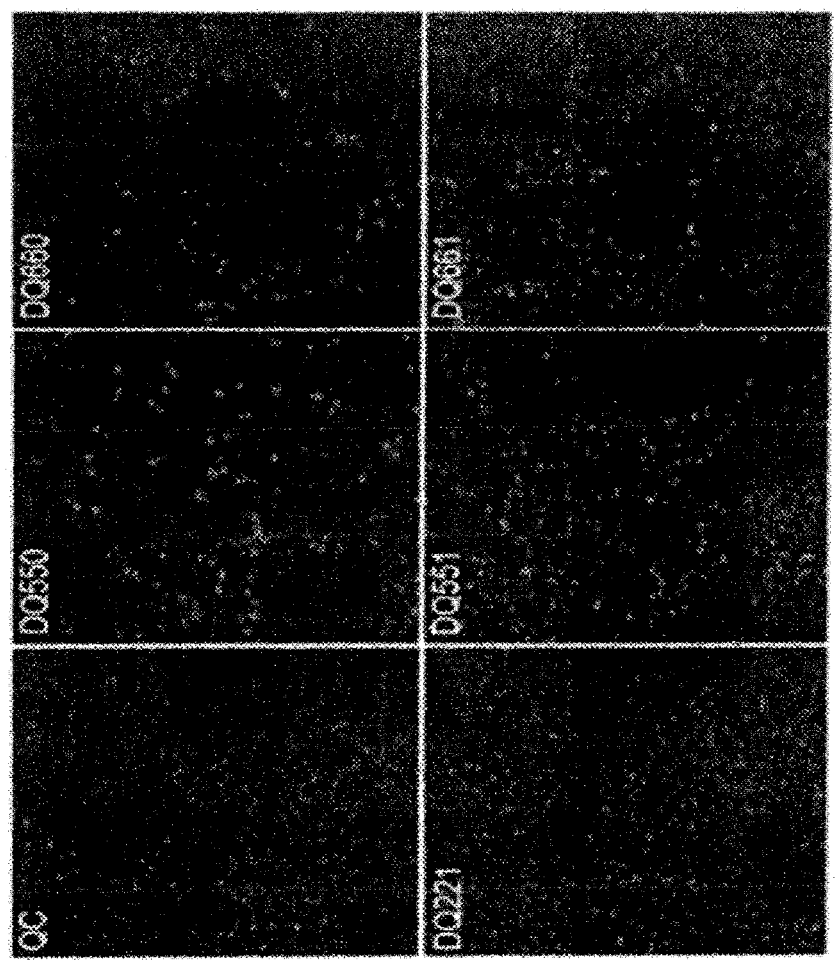
Figure 3:
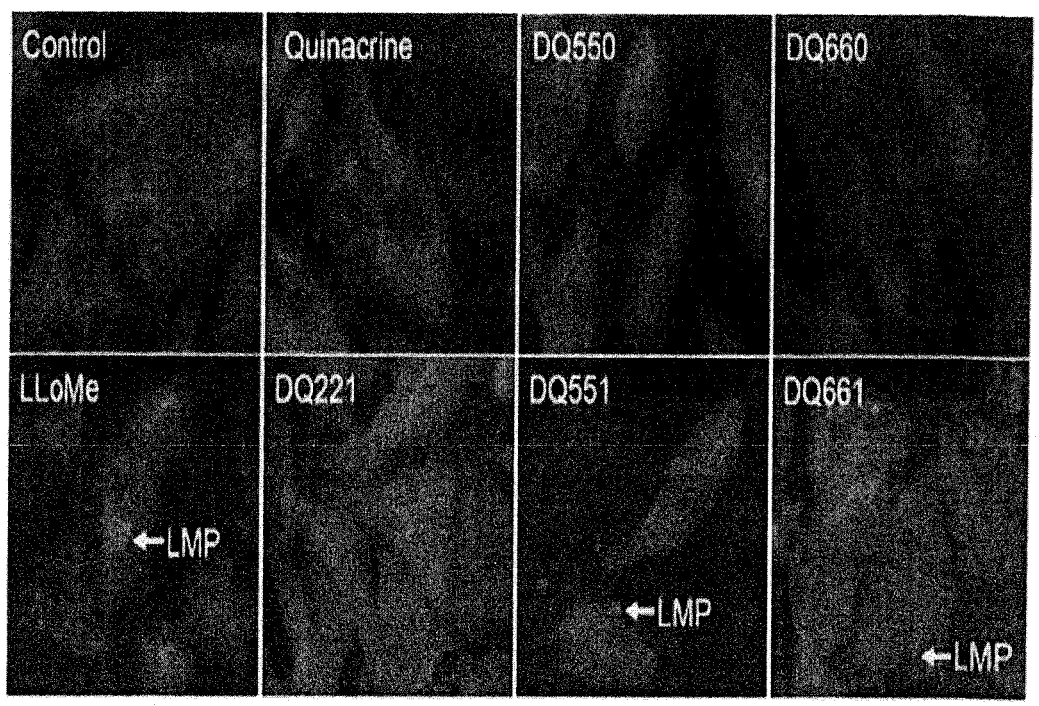

The longer linked DQs can be separated into two classes based on central nitrogen substitution (secondary or tertiary amine)—those that localize to the nucleus and those that localize to the lysosome. We next sought to determine whether both classes of DQs cause DNA damage since quinacrine is known to intercalate DNA. A375P cells treated with quinacrine or DQs (DQ221, DQ550, DQ551, DQ660, DQ661) for 6 hours and imaged by immunofluorescence microscopy revealed a striking pattern between nitrogen alkylation and the phosphorylation of histone H2A variant H2AX at Ser 139 (γ-H2AX) (FIG. 3A). The unmethylated DQs, DQ550 and DQ660, induced significantly greater levels of DNA damage relative to their methylated counterparts DQ551 and DQ661 (FIG. 3A). Furthermore, the difference in DNA damage induced by unmethylated DQs versus the corresponding methylated DQs for each pair of compounds increase with increasing linker length.

The integrity of the lysosomal membrane was next interrogated by detection of lectin galactosidase-binding soluble 3 (LGALS3)/galectin-3 localization, which was recently demonstrated to rapidly translocate to leaky lysosomes that have been damaged (Aits et al., 2015). When lysosomes are healthy, galectin-3 is uniformly dispersed throughout the cell. However, when the lysosome is damaged, galectin-3 rapidly localizes to the site of damaged lysosomes, appearing as punctae and marking individual leaky lysosomes. A375P cells treated with quinacrine, positive control L-leucyl-L-leucine methyl ester (LLOMe), and DQs (DQ550, DQ551, DQ660, DQ661) for 6 hours and imaged by immunofluorescence microscopy revealed another striking pattern in which only methylated DQs caused lysosomal membrane permeabilization (LMP), as seen by the formation of galectin-3$^+$ punctae (FIG. 3B). A diffuse staining for galectin-3 was observed in control, quinacrine, DQ221, DQ550 and DQ660 treated cells. In contrast, a punctate distribution of galectin-3 was seen in cells treated with the positive control LLOMe, as well as with the longer linked methylated DQs, DQ551 and DQ661 (FIG. 3B). Altogether, these results demonstrate that unmethylated DQs localize to the nucleus and cause dsDNA H2AX+ breaks, whereas methylated DQs localize to the lysosome and cause LMP, with DQ661 eliciting the greatest level of LMP across all compounds tested.

Figure 4:
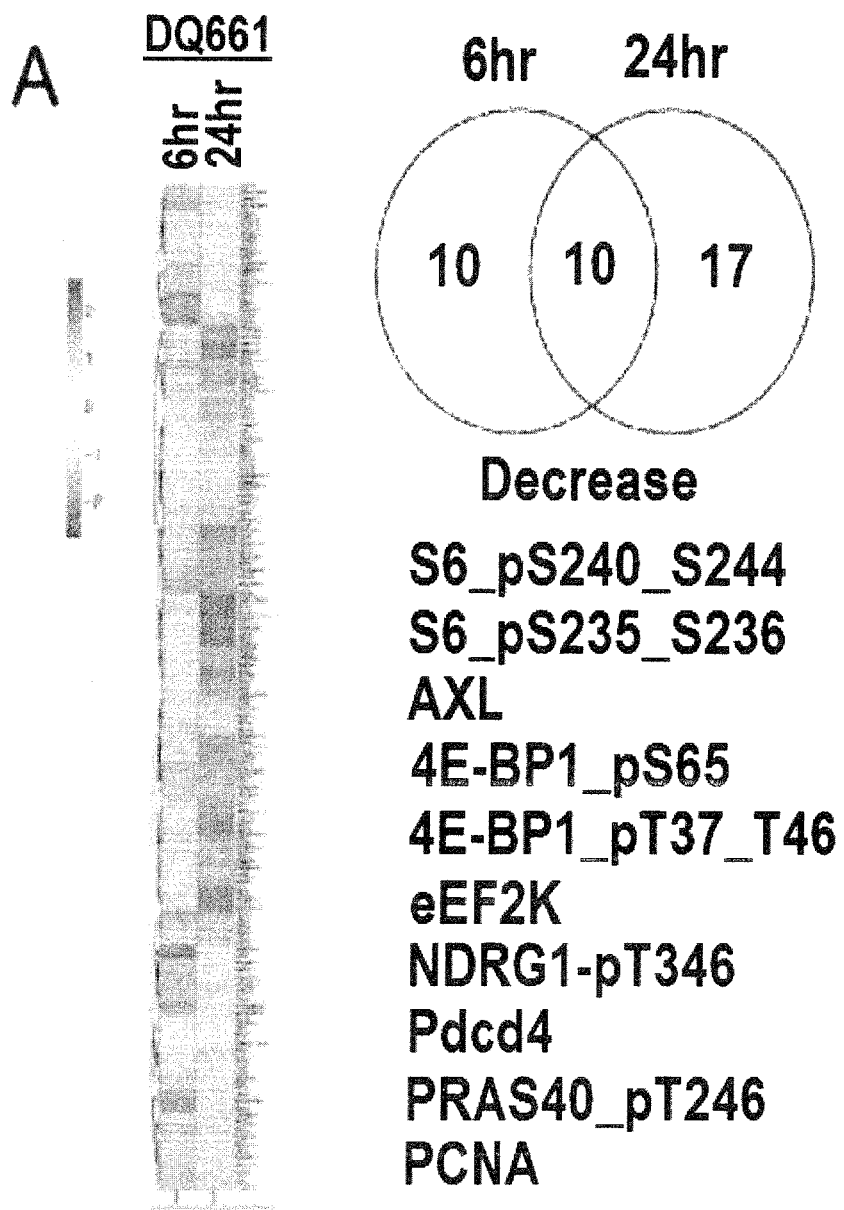
FIG. 4: DQ661 inhibits mTORC1 via disruption of mTORC1/lysosomal interaction. (A) A375P cells were treated with lead compound DQ661 (6-24 hr, 3 µM) and lysate was run on RPPA. Depicted on the left is a heat map showing the average of 3 biological replicates for the 6 hr and 24 hr timepoints. The most significantly inhibited proteins common across both timepoints (10) are shown below the Venn diagrams (fold change ≥1.4, p≤0.05). (B) Demonstrates signaling nodes in the PI3K/AKT/mTOR pathway that are inhibited by DQ661, suggesting mTORC1 is inactivated. (C) DQ661 inhibits mTORC1 in a lysosomal pH-dependent manner, distinct from other lysosomal targeting/disrupting agents. A375P cells were treated for 6 hr with DQ661 (3 µM), PBS, Pepstatin A (10 µG/mL), E64 (10 µG/mL), Pepstatin A+E64, Siramesine (8 µM), PES (10 µM), PET (10 µM), Bafilomycin A1 (100 nM), Bafilomycin A1+DQ661 or Pepstatin A+DQ661. Lysate was subsequently immunoblotted for phospho-S6K T389, total S6K, phospho-4E-BP1 S65, total 4E-BP1, LC3B and Actin. (D) A375P cells were treated with vehicle control or DQ661 (6 hr, 3 µM) and cells were subsequently stained for mTOR (red), LAMP2 (green) and DAPI (blue). Cells were imaged with fluorescent microscopy. (E) DQ661 removes RaGTPase/Ragulator machinery off of the lysosomal surface. A375P cells were treated with vehicle control, DQ660 or DQ661 (4 hr, 1 µM). Lysosomes were subsequently purified and whole-cell/lysosomal protein lysate was immunoblotted for LAMP2, LAMTOR1 (p18), RagA, RagC, Cathepsin D and Actin. Quantification of lysosome to whole-cell ratios for LAMTOR1 (p18) RagA and RagC are shown to the right.
Figure 4:
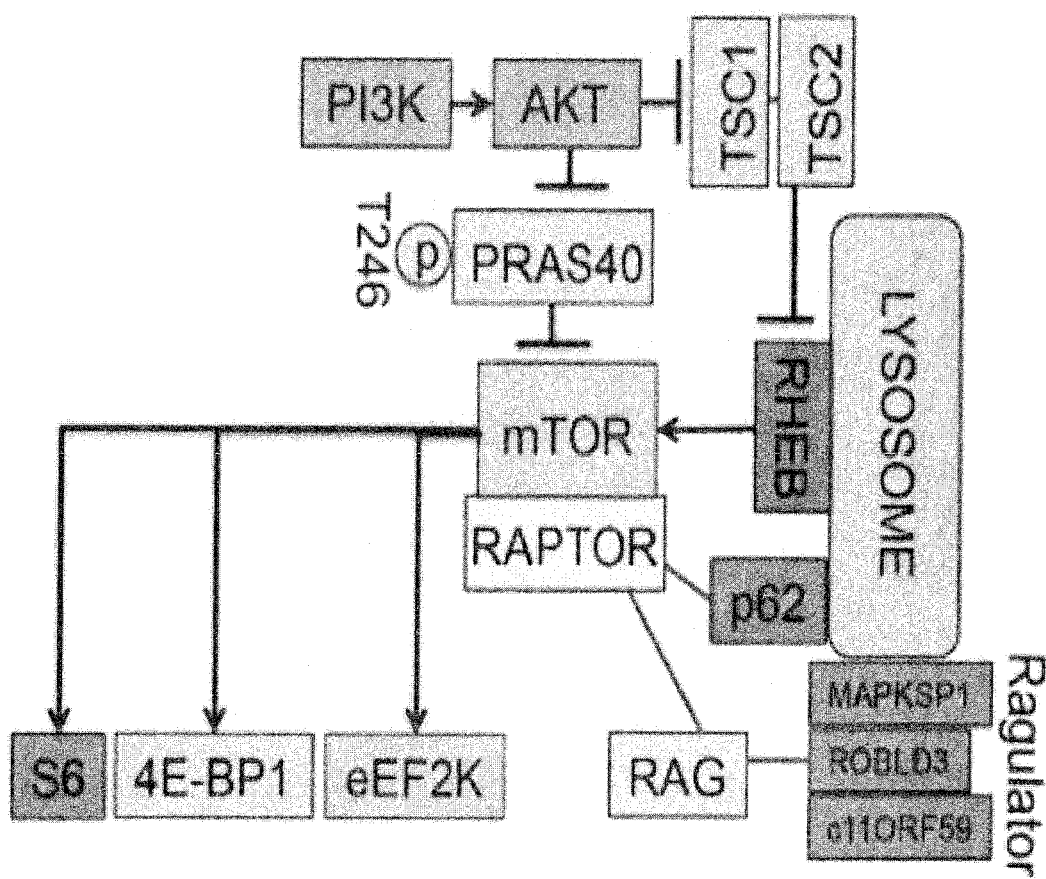
Figure 4:
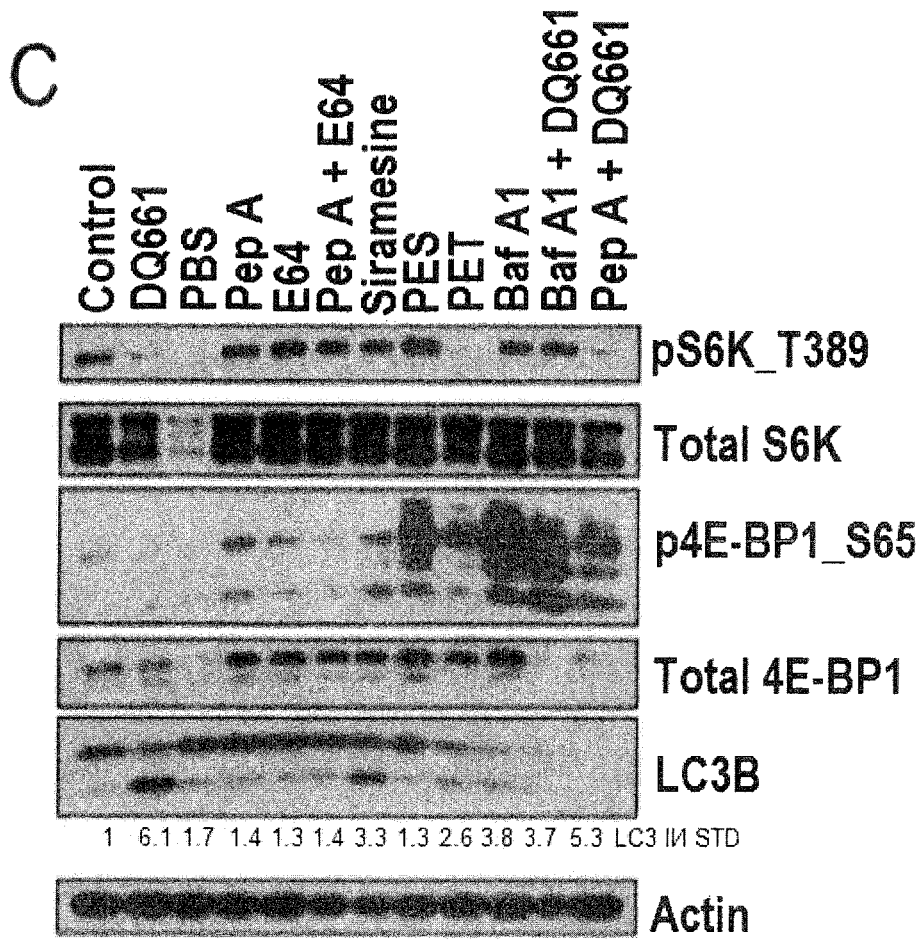
Figure 4:
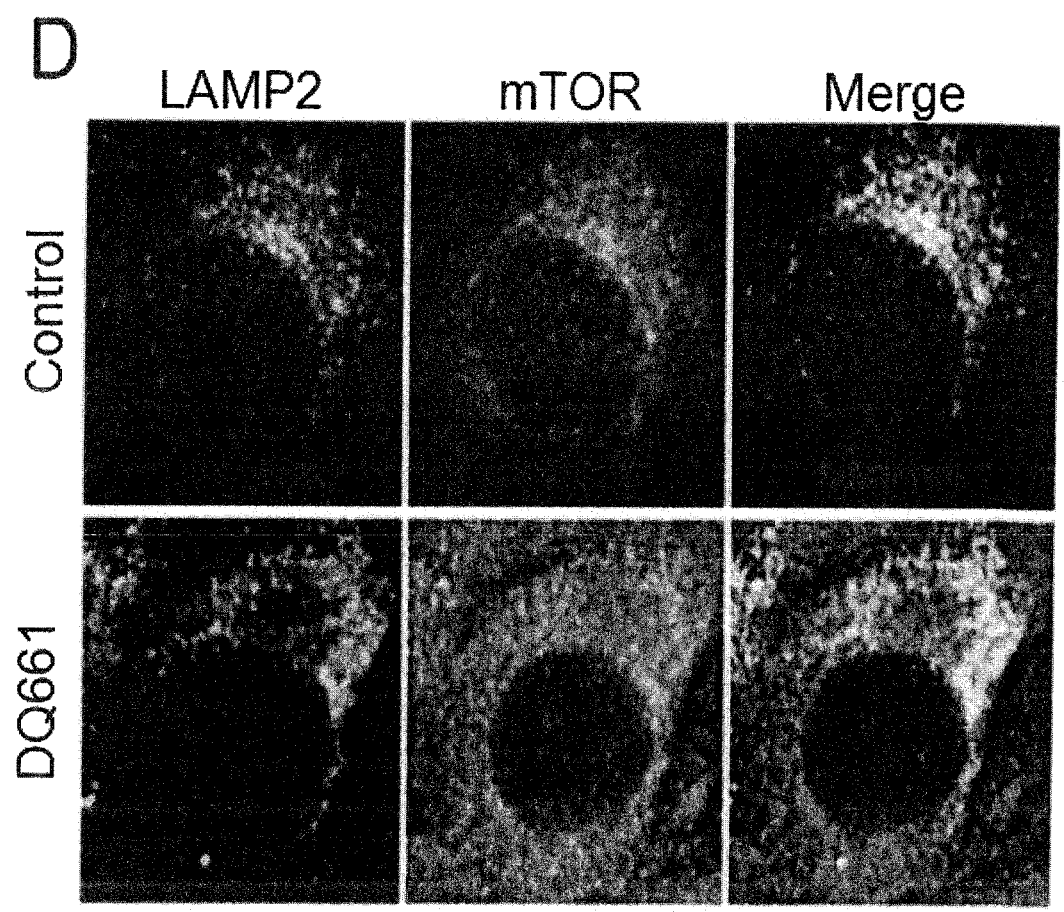
Figure 4:
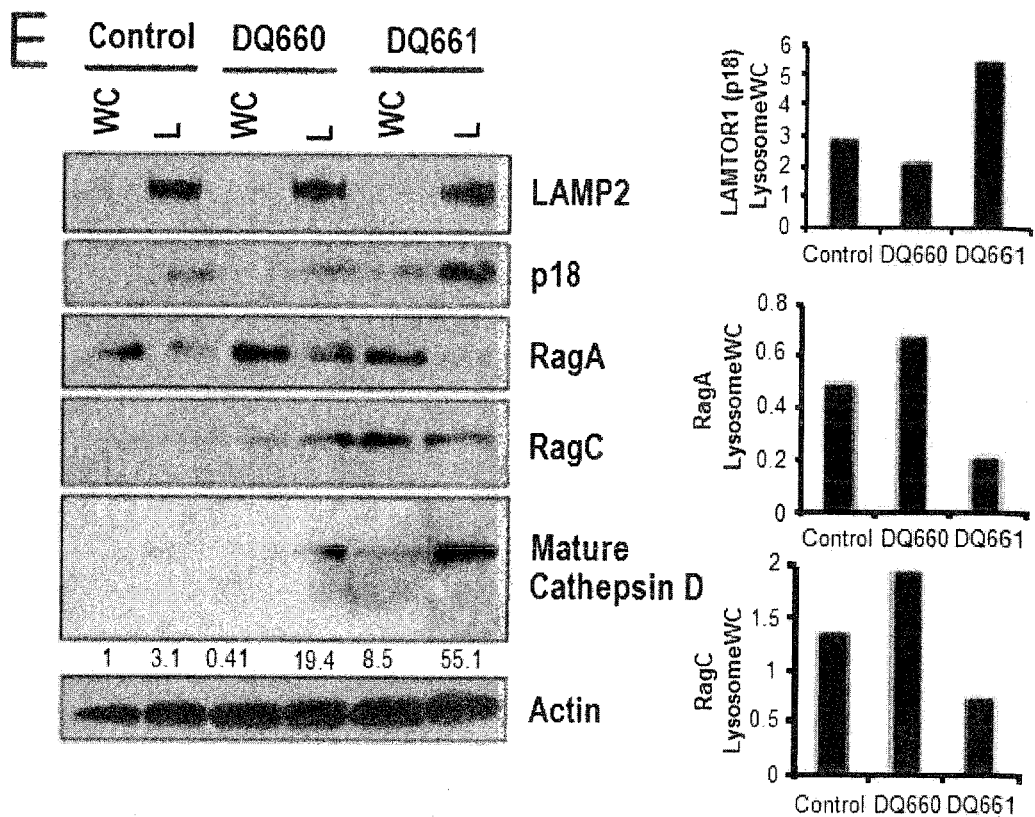
Figure 4:
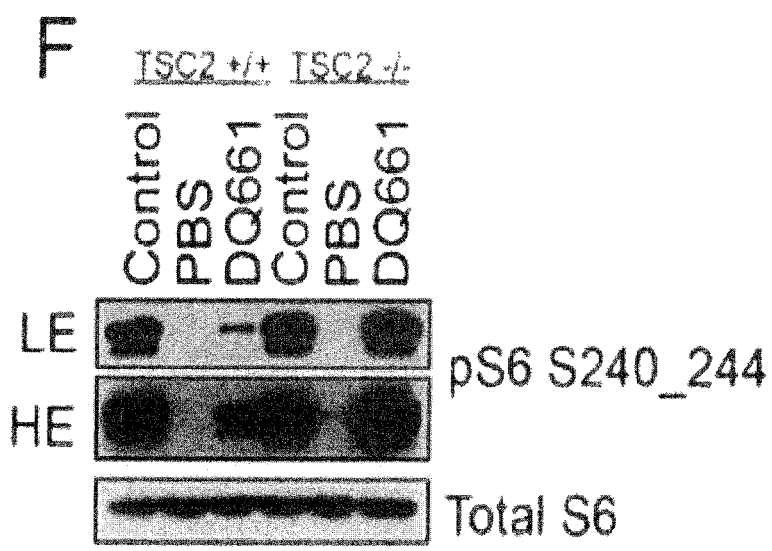
Figure 4:
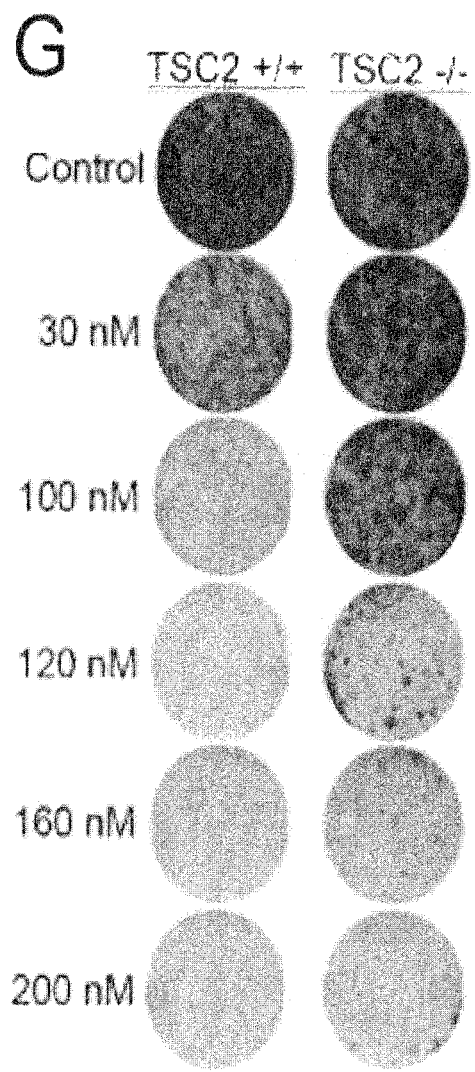

DQ661 Inhibits mTOR Activity Via Uncoupling of mTORC1/RaGTPase/Ragulator Machinery from the Lysosomal Surface To understand the mechanism of action of the anti-cancer activity of DQ661, A375P cells were treated for either 6 or 24 hours with DQ661 and lysate was used to perform reverse phase protein array (RPPA) studies. A total of 10 proteins were significantly inhibited at both the 6-hour and 24-hour time points (FIG. 4A). Six of these ten proteins are involved in the mechanistic target of rapamycin (mTORC1) signaling in either a regulatory manner (proline-rich AKT substrate of 40 kDa, PRAS40) or as effectors (S6 ribosomal protein (S6), eukaryotic translation initiation factor 4E-binding protein 1 (4E-BP1), and eukaryotic elongation factor-2 kinase (eEF2K)) (FIG. 4B). Western blotting for phospho-S6 (S240/244), phospho-S6K (T389) and phospho-4E-BP1 (S65) confirmed the RPPA results showing DQ661 potently inhibits mTORC1 activity (FIG. 4C). We next sought to compare the anti-mTOR activity of DQ661 with effective doses of other known lysosomal inhibitors. A375P cells were treated with either amino acid starvation, pepstatin A, E64, Pepstatin A+E64, siramesine, PES or PET, bafilomycin A1, bafilomycin+DQ661, or pepstatin A+DQ661 for 4 hours. Lysate was immunoblotted for phospho-S6K (T389), phospho-4E-BP1 and LC3B. DQ661 was observed to inhibit S6K and 4E-BP1 to a similar degree as the classical control of amino acid starvation (FIG. 4C). Further Pepstatin A, an inhibitor of aspartyl proteases, in the presence or absence of E64, an inhibitor of cysteine proteases, did not significantly affect mTORC1 activity. Siramesine, a sigma-2 receptor ligand that has been previously reported to destabilize lysosomes, also did not inhibit mTORC1 activity. PES and PET are small molecule inhibitors of heat shock protein 70 (HSP70), a chaperone for many lysosomal proteins that also inhibits autophagy. PET inhibited S6K phosphorylation, but both PES and PET treatment led to the hyperphosphorylation of 4E-BP1 (FIG. 4C). Bafilomycin, a potent inhibitor of the vacuolar H+ ATPase, also resulted in hyperphosphorylation of 4E-BP1. Interestingly, concurrent bafilomycin and DQ661 treatment blunted the ability of DQ661 to inhibit S6K and 4E-BP1 phosphorylation (FIG. 4C). Since it was previously shown that bafilomycin could displace the lysosomal localization of DQ661, these results suggest the ability of DQ661 to inhibit mTORC1 depends on its proper intracellular localization to the lysosome. The addition of pepstatin A to DQ661 did not blunt ability of DQ661 to inhibit S6K phosphorylation, suggesting DQ661's activity against S6K to be independent of aspartyl proteases (FIG. 4D). LC3B levels were also monitored and demonstrated DQ661 had the greatest ability to inhibit autophagy among the entire panel of lysosomal inhibitors, as seen by the greatest accumulation of LC3II/LC3I levels (FIG. 4C).

mTORC1 localizes to the lysosome in an amino acid-dependent fashion, allowing full activation by Rheb, which is also located on the lysosomal surface (Efeyan et al., 2012). Since mTORC1 requires lysosomal localization for its full activation, we next sought out to determine whether DQ661 interferes with mTORC1 localization to the lysosome. A375P cells were treated with either vehicle control or DQ661 for 6 hours. Cells were subsequently stained and imaged for Dapi, mTOR and the lysosomal marker lysosome-associated membrane protein 2 (LAMP2). In vehicle control cells, mTOR was localized to the lysosome. DQ661 treatment resulted in the loss of mTOR and lysosomal co-localization as seen by the diffusion of mTOR throughout the cytoplasm (FIG. 4D). To further understand how DQ661 could be removing mTORC1 from the lysosomal compartment, lysosomes were purified from cells treated with either vehicle control or DQ661 and components of the machinery required to recruit mTORC1 to the lysosomal surface were investigated by Western blotting. DQ661 was shown to increase the cytoplasmic/lysosomal ratios of RagC and LAMTOR1 (p18), suggesting DQ661 was stripping the RaGTPase/Ragulator machinery off the surface of lysosomes (FIG. 4E). Cathepsin D was also observed to increase in the cytoplasmic fraction upon DQ661 treatment, providing additional evidence of DQ661-induced LMP (FIG. 4E). TSC2 is a negative regulator of Rheb and studies have demonstrated constitutive mTORC1 activity and localization to the lysosomal surface in cells deficient for TSC2. DQ661 failed to produce dephosphorylation of the mTOR substrate phospho-S6 (FIG. 4F). TSC2−/− MEFs which have constitutively activated mTOR were partially resistant to DQ661− associated colony formation impairment compared to TSC2+/+ MEFs (FIG. 4G).

In Vivo Lysosomal Inhibition and Anti-Tumor Activity of DQ661 in a Melanoma Xenograft Model.

Figure 5:
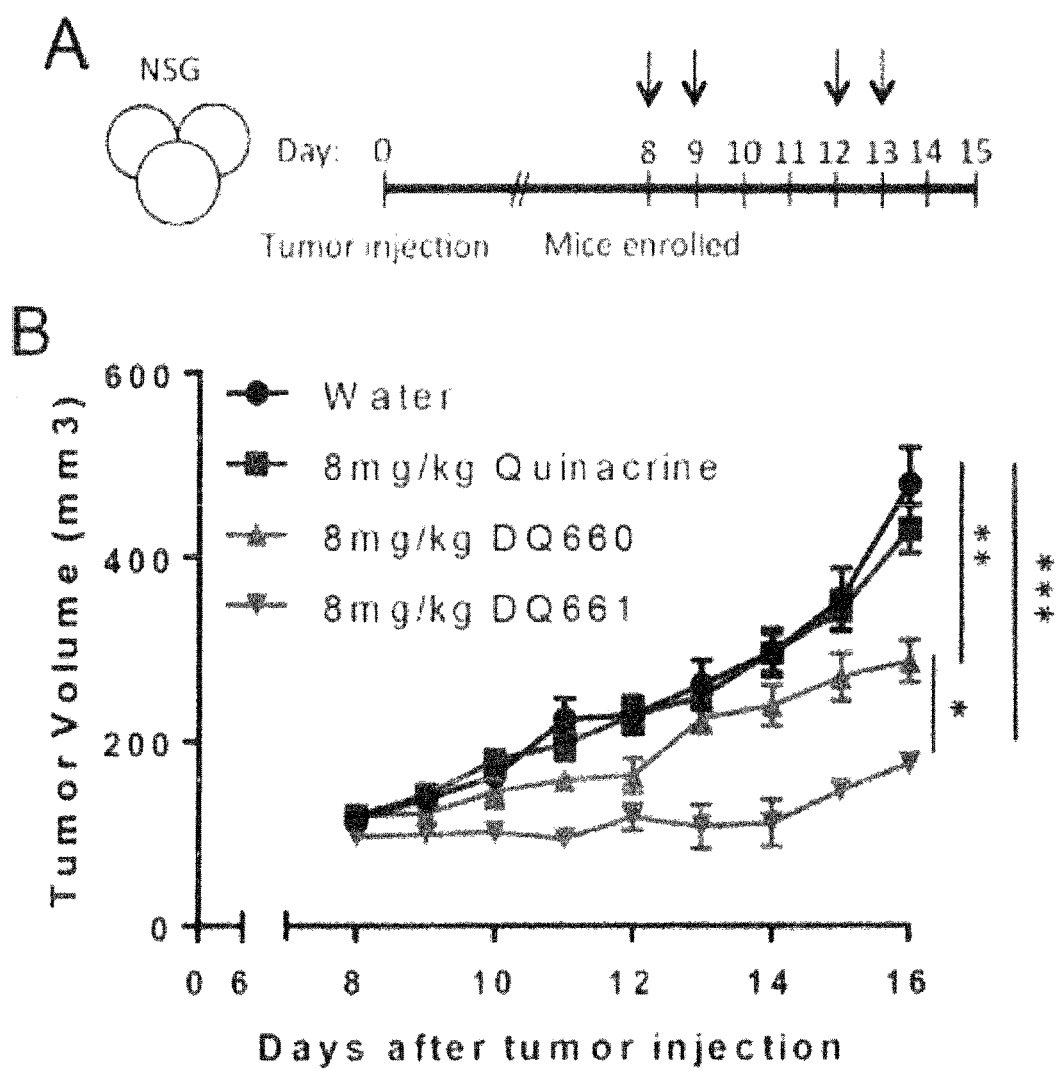
FIG. 5: DQ661 has significant single-agent in vivo activity in melanoma xenograft model. (A) A schematic for how mice were treated in (B). 1205Lu cells were injected subcutaneously in the flanks of NSG-mice ($2\times10^6$/mouse) and grown until tumors were palpable (1-2 weeks). Mice were randomly split into 4 arms and treated with vehicle control (water, i.p.), quinacrine (8 mg/kg, i.p.), DQ660 (8 mg/kg, i.p.) or DQ661 (8 mg/kg, i.p.). Treatments were given as shown by the black arrows, following a regimen of 2 days on treatment followed by 2 days off treatment. (C) Representative electron micrographs from melanoma xenograft tumors harvested after 2 days of treatment according to (B). (D) Average tumor volumes for each treatment arm are shown. Each point represents the mean of N=8 mice per treatment arm and the error bars represent standard error (s.e.) (C) Representative EM for tumors treated in each arm. (E) A schematic for how mice were treated in (F). (F) 1205Lu cells were injected subcutaneous in NSG-mice ($2\times10^6$/mouse) and grown until tumors were palpable (1-2 weeks). Mice were randomly split into 3 arms and treated with water (i.p.), DQ661 (2 mg/kg, i.p.) or DQ661 (4 mg/kg, i.p.). Treatments were give as shown by the black arrows, following a regimen of 2 days on treatment followed by 2 days on treatment. Tumor volume is shown. Each point represents the mean of N=8 mice per treatment arm and the error bars represent s.e. (G) Average tumor growth rate for each treatment arm are shown. (H) Protein lysate was harvested from mouse tumors at the end of the experiment and immunoblotted for LC3B, phospho-4E-BP1 T37_T65, phospho-4E-BP1 S240_S244 and Actin. Quantification of proteins standardized to control mice levels are shown to the right.
Figure 5:
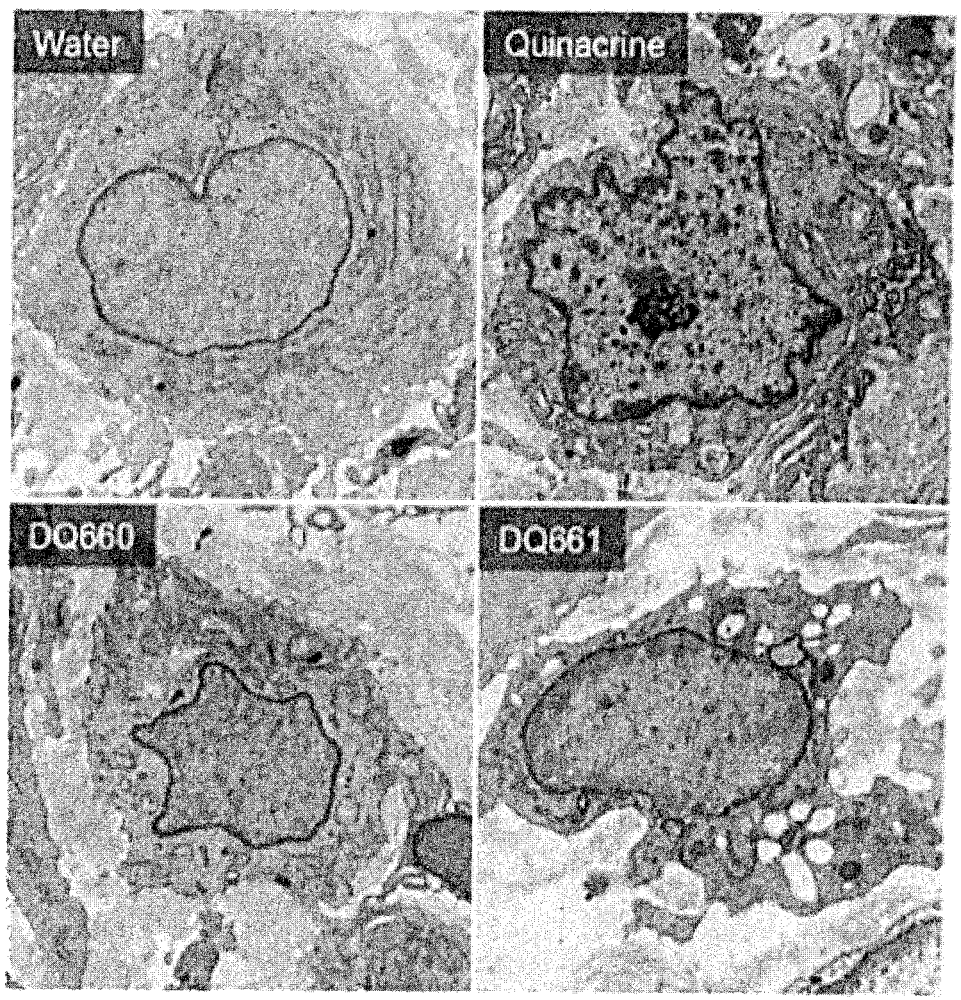
Figure 5:
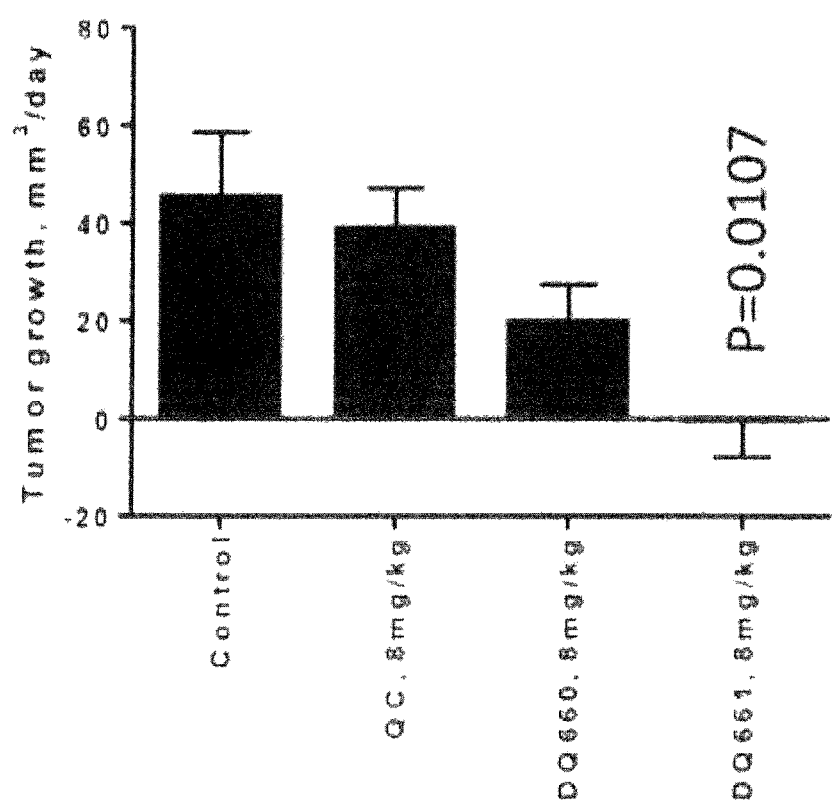
Figure 5:
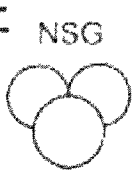
Figure 5:
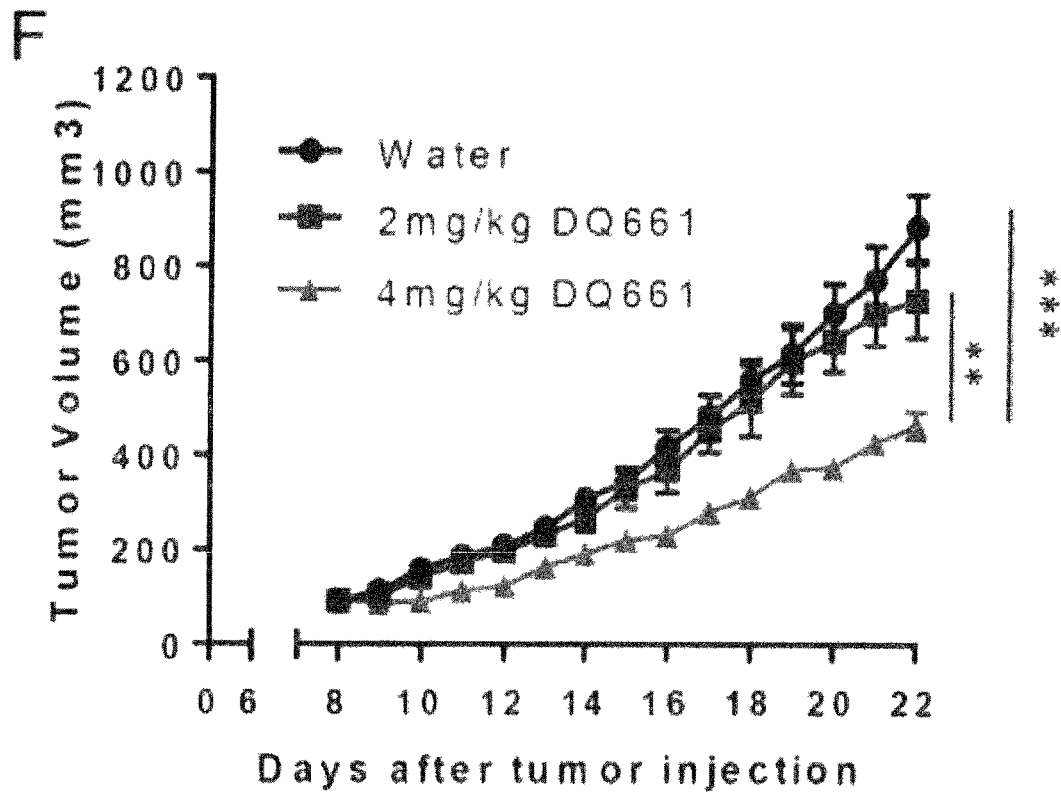
Figure 5:
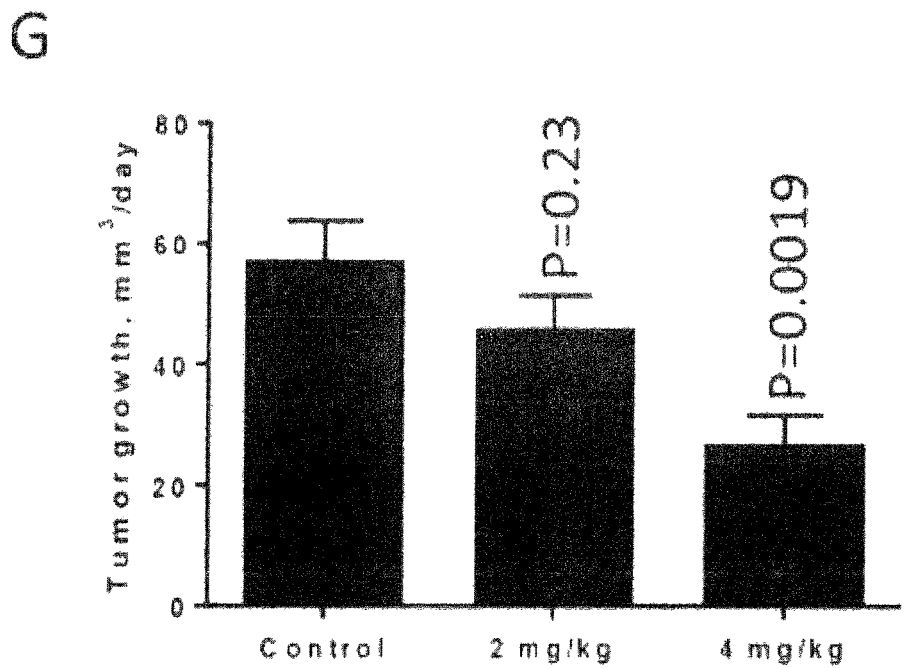
Figure 5:
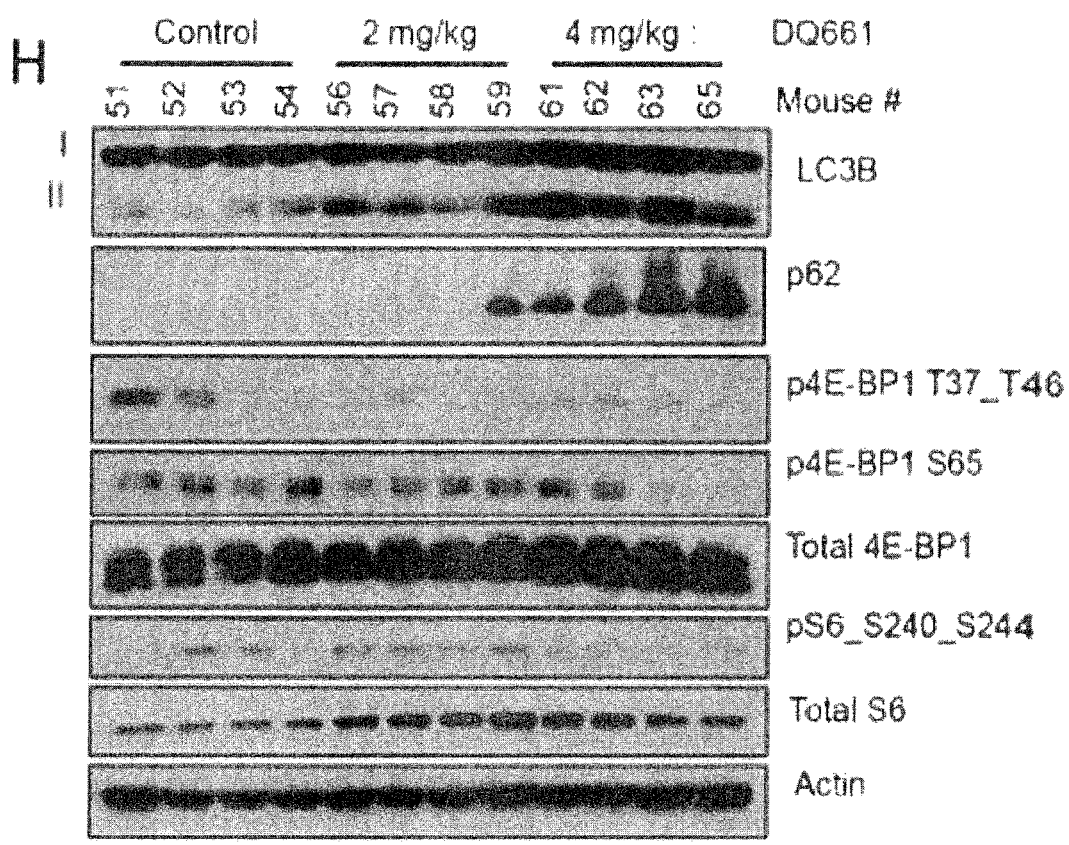

To determine whether DQ661 possessed in vivo activity, 1205Lu melanoma xenografts were established on the flanks of NSG mice. After 1-2 weeks, tumors were palpable and mice were treated with vehicle control (water), quinacrine (8 mg/kg), DQ660 (8 mg/kg) or DQ661 (8 mg/kg) i.p (FIG. 5A). Quinacrine had no significant effect on tumor growth compared to vehicle control (FIG. 5B). DQ660 treatment resulted in a modest but significant growth impairment of tumors compared to control or QC treated tumors. However treatment with DQ661 inhibited tumor growth to the greatest extent. Despite differing in structure by only one methyl group on the central nitrogen, DQ661 possessed significantly greater in vivo activity and inhibited autophagy as seen by electron microscopy of mouse tumors (FIG. 5C) At the 8 mg/kg dose, however, DQ661 caused weight loss of mice greater than 10% and by day 7 all mice were euthanized due to lethargy and bowel distension. Histological analysis of the intestines and liver demonstrated Paneth cell dysfunction in DQ661-treated mice similar to that observed in mice treated with the highest doses of Lys05. Therefore another 1205Lu xenograft experiment was performed with mice treated with either vehicle control (water, n=6) or DQ661 (2 or 4 mg/kg, n=6) for a period of 14 days (FIG. 5e, 5F). DQ661 resulted in a significant reduction in tumor volume and tumor weight compared to control mice without significantly effect mice weight. DQ661 treated tumors had significantly slower rates of growth (FIG. 5G). Evidence of concurrent in vivo autophagy inhibition and mTORC1 inhibition was obtained by Western blotting for LC3, p62, and mTORC1 signaling targets phospho-4EBP1 and phospho-S6 in lysate from DQ661 treated tumors compared to control tumors (FIG. 5F).

DQ661 has Antitumor Activity as a Single Agent and in Combination with Chemotherapy in a KPC Immunotherapy/Radiation-Resistant Pancreatic Xenograft Model.

Figure 6:
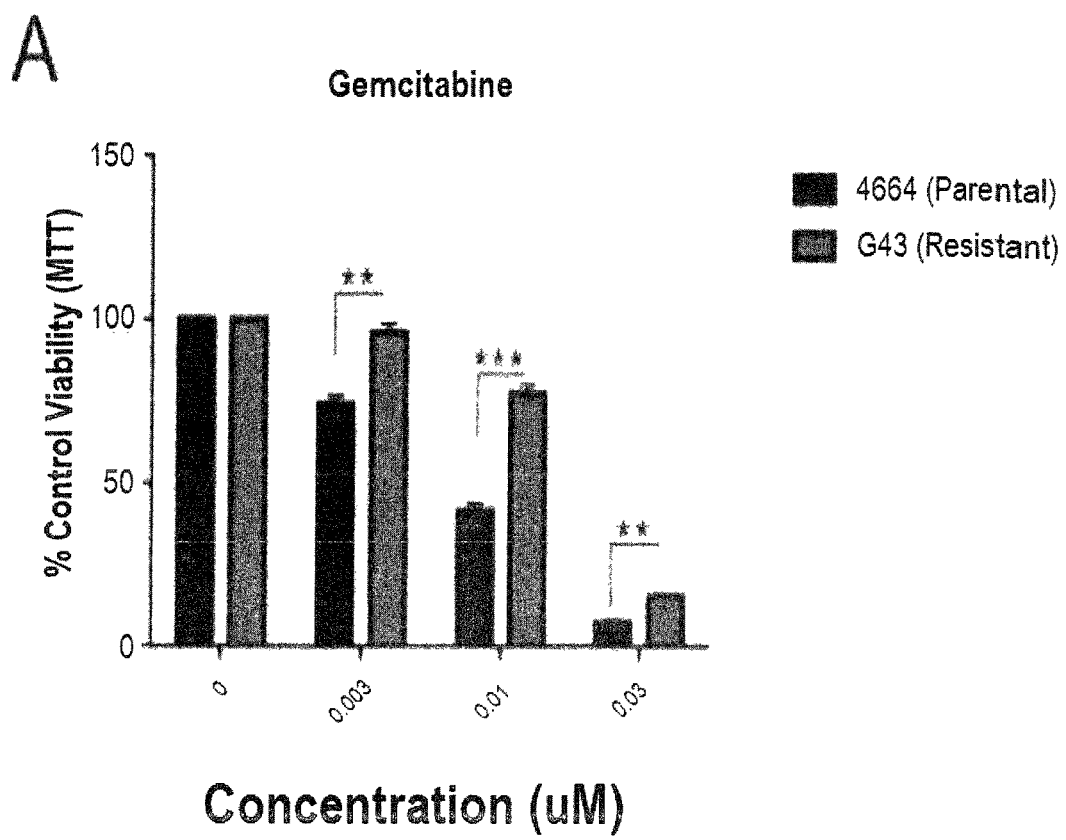
FIG. 6: DQ661 potentiates in vivo activity of gemcitabine in KPC pancreatic cancer syngeneic model. (A) 4664 and G43 cells were treated with gemcitabine (72 hr, 3-30 nM). MTT was subsequently added and cell viability was determined by standardizing absorbance to control wells. (B) G43 cells were treated chronically for 2 weeks with gemcitabine (3-30 nM) in the presence or absence of DQ661 (30-300 nM) in colony formation assays. Cells were subsequently stained with crystal violet and imaged. (C) A schematic for how mice were treated in (D). G43 cells were injected into C57BL/6 mice ($2\times10^6$ cells/mouse. Once palpable, mice were treated with vehicle (water, PBS), gemcitabine (120 mg/kg, i.p., once at day 6), DQ661 (4 mg/kg, i.p., starting on day 7 according to the regimen of 2 days on treatment followed by 3 days off treatment) or a combination of gemcitabine and DQ661. (D) Average tumor volumes for each treatment arm are shown. Each point represents the mean of N=8 mice per treatment arm and the error bars represent s.e. (E) Tumor growth rate from (D).
Figure 6:
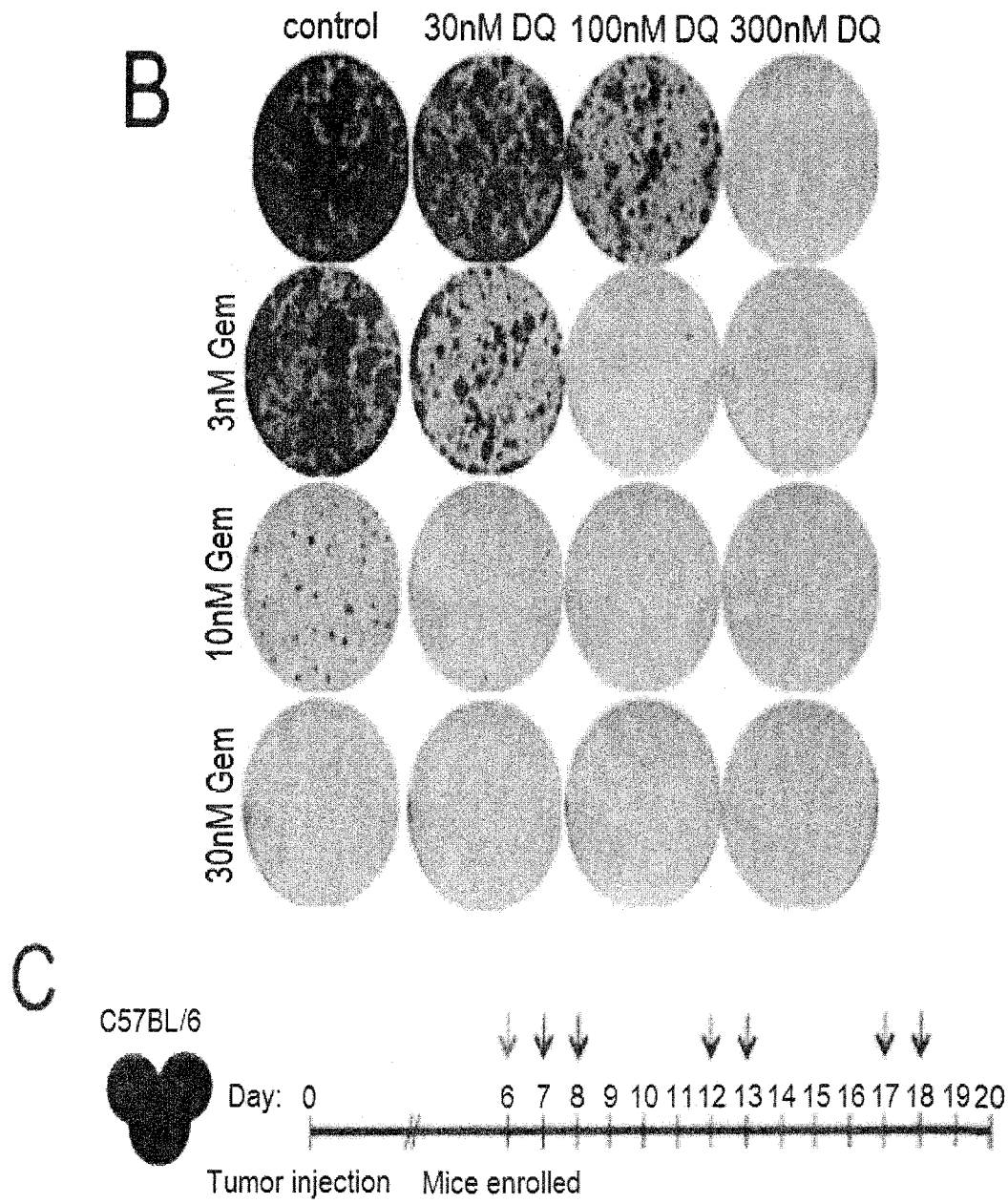
Figure 6:
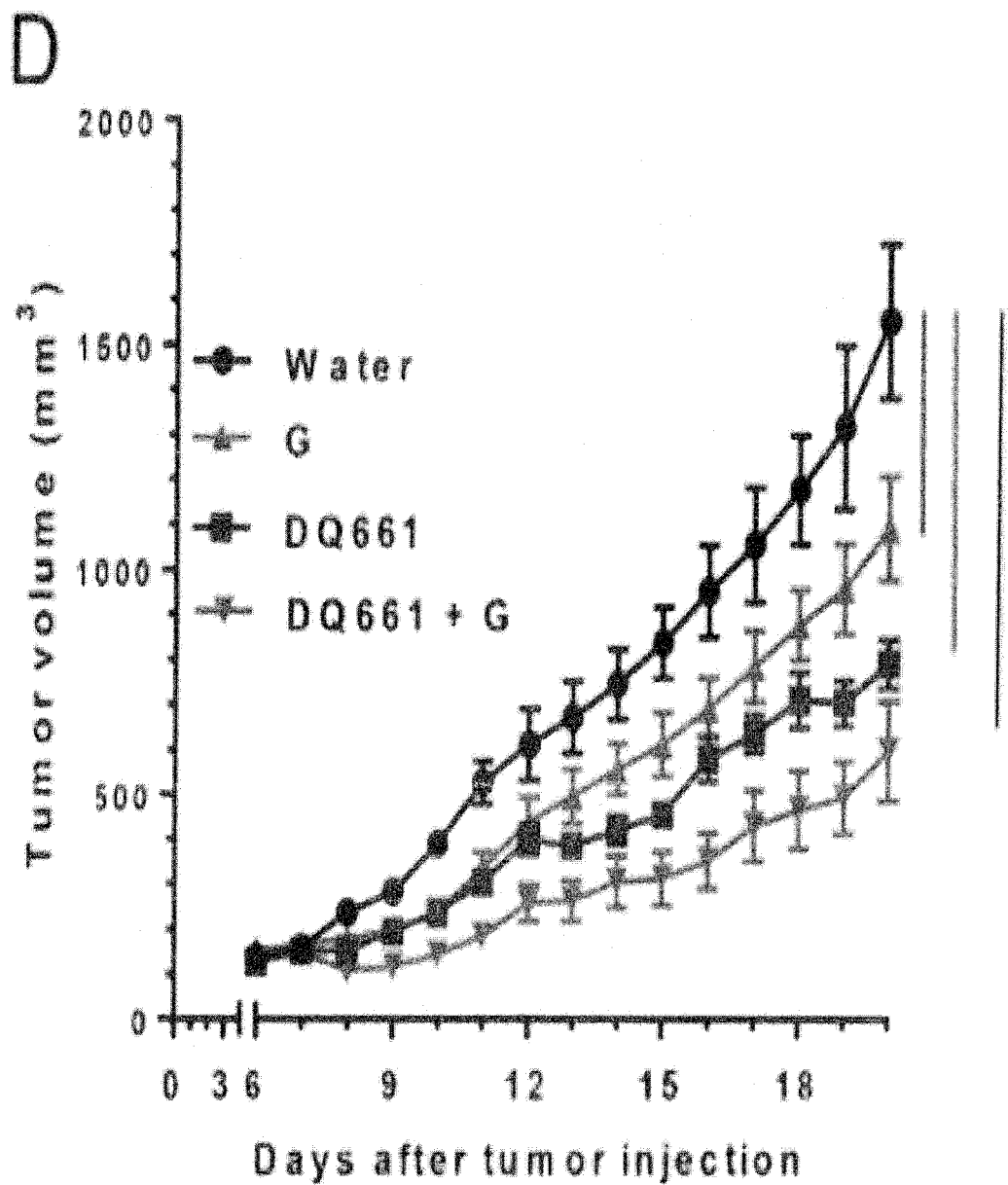
Figure 6:
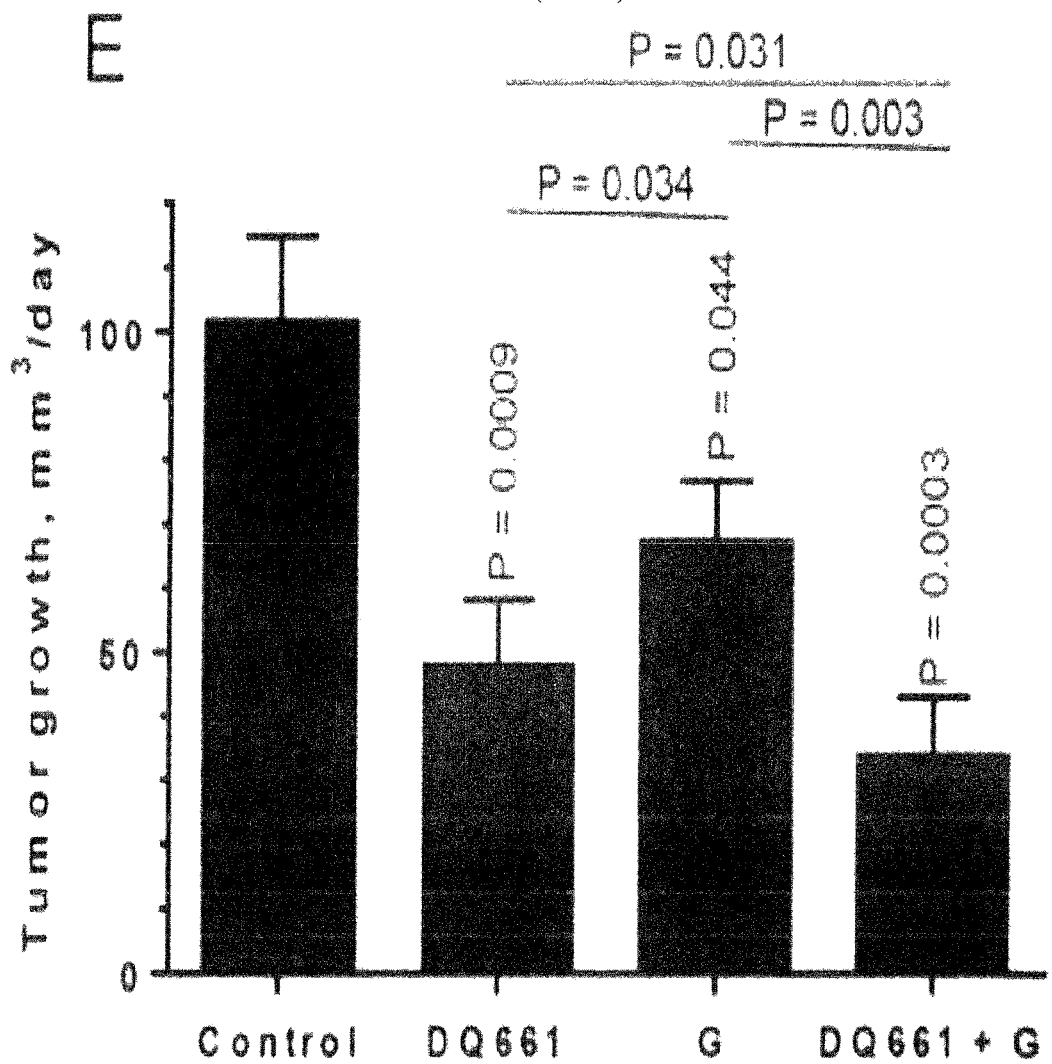
Figure 7:
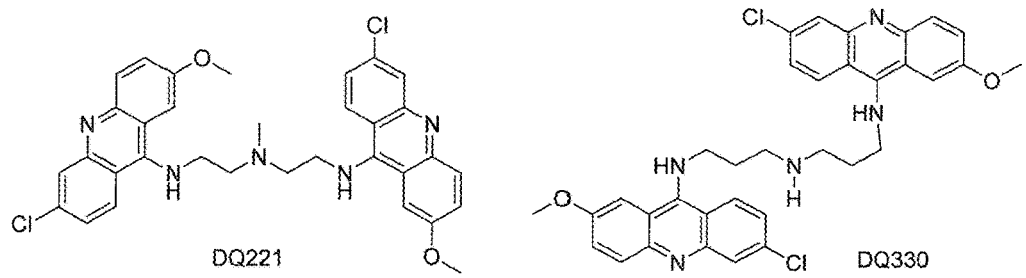
FIG. 7 shows certain preferred compounds according to the present invention.
Figure 7:
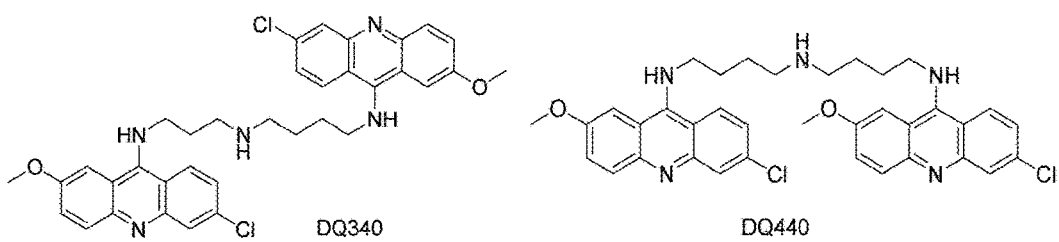
Figure 7:
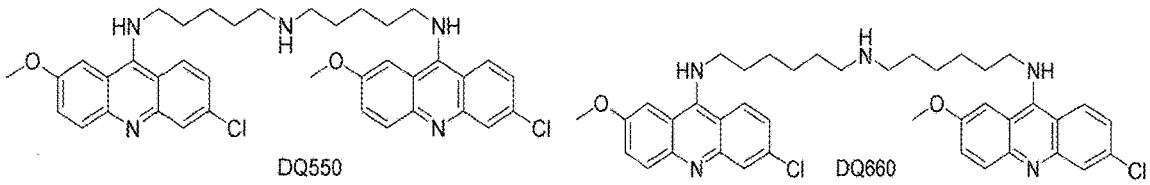
Figure 7:
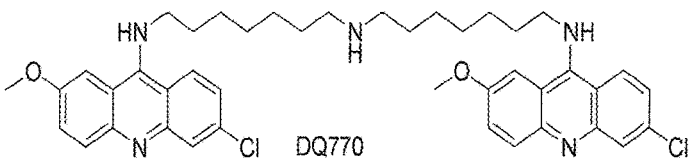
Figure 7:
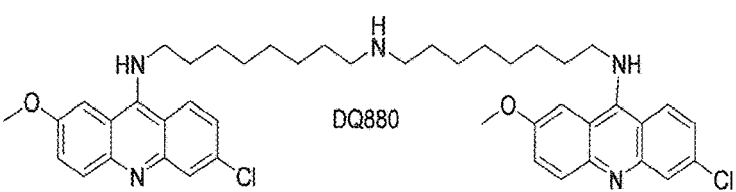
Figure 7:
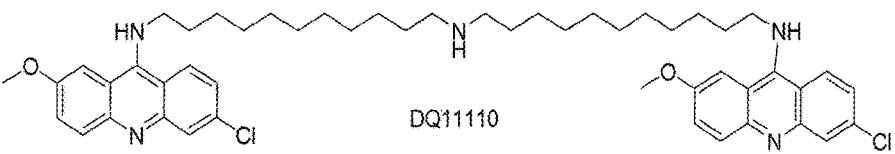
Figure 7:
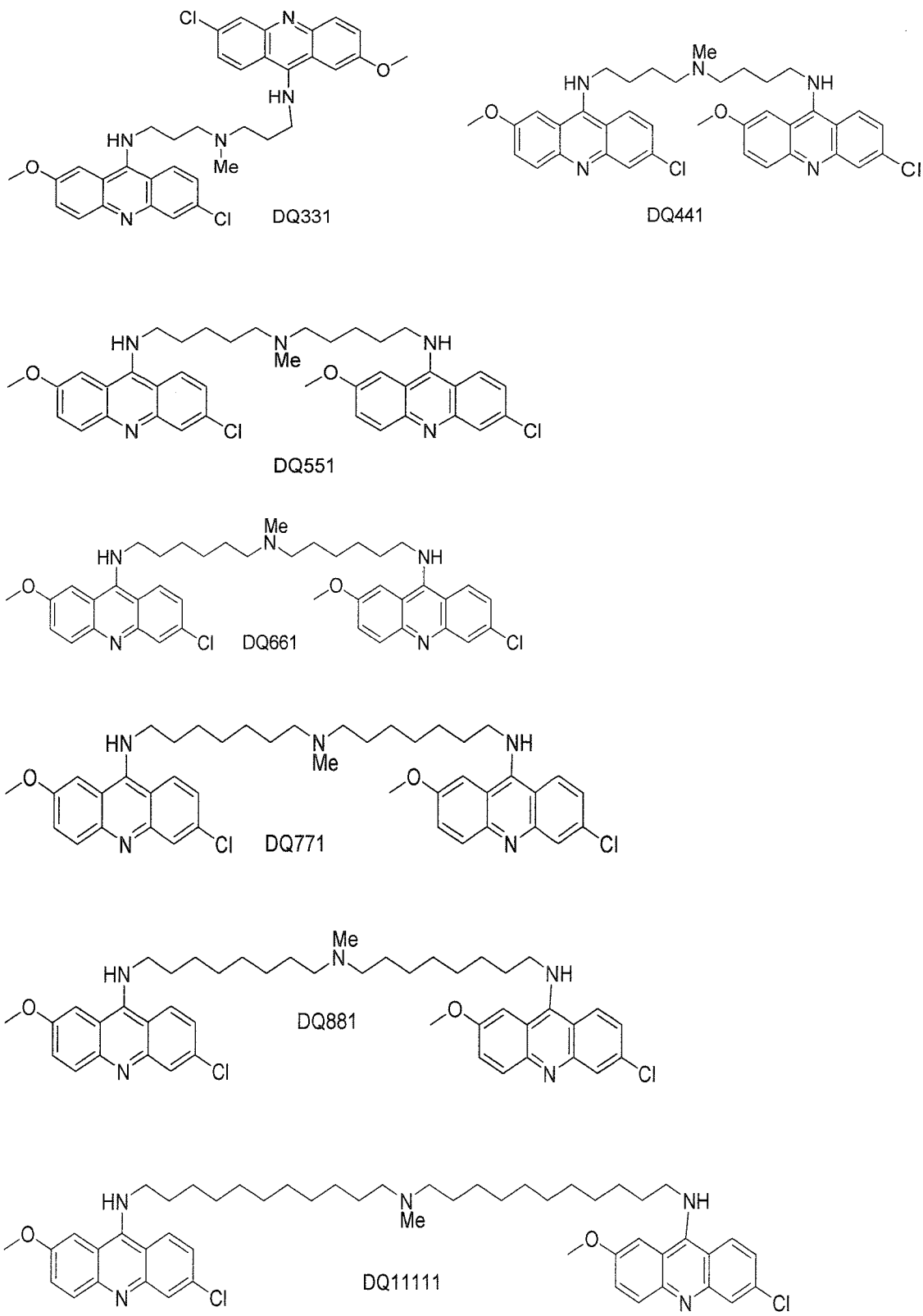

Pancreatic ductal adenocarcinoma (PDA) requires high levels of autophagy-lysosome function, which plays a critical role in the survival and escape of pancreatic cancer cells from a variety of therapeutics, including gemcitabine (Yang et al., 2014). Lysosomal function in particular was reported to be critical for pancreatic cancer cell metabolism (Perera et al., 2015). We next wanted to determine whether DQ661 has activity against treatment naïve as well as immunotherapy/radiation resistant pancreatic cancer cells. Two mouse cancer cell lines were derived from the genetically engineered mouse model (GEMM) KRASmutant/p53 mutant (KPC): the 4664 cell line (parental) and the G43 cell line, which were generated from a resistant 4664 tumor that grew in the face of anti CTLA4 blockade combined with radiation therapy (Twyman-Saint Victor et al., 2015). These cell lines were treated with increasing doses of gemcitabine, or DQ661. The immunotherapy/radiation-resistant G43 cells were found to also be resistant to gemcitabine, relative to the parental treatment naïve 4664 cells (FIG. 6A). Interestingly, G43 cells were also significantly more resistant to the anti-proliferative effects of DQ661 relative to the parental line. To determine whether inhibition of autophagy with DQ661 would potentiate the effects of gemcitabine, G43 cells were treated with gemcitabine in the presence or absence of DQ661 in long-term colony formation assays. DQ661 synergistically enhances the anti-tumor activity of gemcitabine against G43 cells (FIG. 6B). To determine whether DQ661 would significantly enhance the in vivo activity of gemcitabine, G43 cells were implanted in the flanks of syngeneic mice treated with vehicle control, gemcitabine (120 mg/kg X1), DQ661 (4 mg/kg) or the combination of gemcitabine (120 mg/kg X1) and DQ661 (4 mg/kg). The DQ661 was administered for 2 days after the gemcitabine dose on a 2 days on 3 days off schedule (FIG. 6C). Tumor growth was significantly impaired by gemcitabine alone, DQ661 alone, or the combination of DQ661 and gemcitabine. Compared to DQ661 alone, or gemcitabine alone, the combination of DQ661 produced a significantly lower tumor growth rate (FIG. 6D). Discussion:

Targeting autophagy has manifested as an encouraging new strategy for cancer therapeutics, however emerging evidence differentiates the importance of lysosomal activity from autophagic activity, a previously unappreciated nuance with important implications. Oncogenic Kras-driven tumors have been reported to be addicted to autophagy, however, recent work leveraging genetic loss-of-functions tools that silence key autophagy machinery including ATG4 and ATG7 could not demonstrate Kras-driven cancer lines require autophagy for growth in vitro or in vivo (Eng et al., 2016). Interestingly, pharmacological inhibition of lysosomal function with CQ possessed equivalent activity amongst autophagy-proficient and autophagy-deficient cells, drawing into question the precise mechanism of action of CQ and similar-acting agents. We observed equivalent activity of the lysosomal inhibitors Lys05 and DQ661 across ATG5$^{-/-}$ and ATG5$^{+/+}$ mefs, corroborating this conclusion that the underlying mechanism of action for lysosomal agents may be independent autophagy. A variety of novel compounds have been reported in recent years possessing the ability to proximally inhibit autophagy, including compound 19 (VPS34 inhibitor), Spautin-1 (promotes degradation of Vps34 PI3 kinase complexes) and SBI-0206965 (ULK1 kinase inhibitor), however, significant anti-tumor activity in vivo with proximal autophagy inhibitors has not be shown to date (Honda et al., 2016). These observations, or the lack thereof, along with our findings demonstrating lysosomal inhibition with DQ661 possesses significant in vivo activity suggests distal autophagy inhibition by way of targeting the lysosome may be the most successful anti-cancer strategy, independent of autophagy all together.

Hyperactivation of mTORC1 signaling has been correlated with worse overall survival of patients with a variety of advanced cancers including melanoma and pancreatic cancer (O'Reilly et al., 2009). Given the dependence of mTORC1 on the lysosomal surface for its full activation and the importance of lysosomal function in pro-tumorigenic processes such as catabolism and exosomes, targeting the lysosome appears to be an ideal strategy. We previously reported an improved lysosomal inhibitor, Lys05, with 10-fold greater potency than CQ at inhibiting autophagy, however Lys05 activity appeared to elicit cytostatic rather than cytotoxic effects in cancer cells. To improve on Lys05, we here executed a large-scale medicinal chemistry-driven effort to systematically study the structure activity relationships (SAR). Extending the triamine linker between the CQ heterocycles leveraging spermidine significantly enhanced autophagy-lysosome inhibition and anticancer potency of Lys05. Further enhancement in potency was obtained when the CQ heterocycle was replaced with quinacrine (QN). Four anti-malarial heterocycles (quinacrine, mefloquine, primaquine and quinaldine) were investigated, with QN performing best when dimerized. DQs that contain a central secondary amine in their triamine linker localized to the nucleus, produced DNA damage, and induced autophagy. Strikingly, conversion to a central tertiary methylated amine in DQs with extended linkers served as a homing signal, localizing these compounds to the lysosome, which was associated with loss of DNA damage, pronounced LMP and autophagy inhibition. DQ-induced LMP displaced mTORC1 from the lysosome via disruption of mTORC1/RaGTPase/Ragulator/lysosomal interactions, in a manner unique amongst other lysosomal disrupting agents. Specifically, the lysosomal/cytosolic fraction of RagA and RagC was decreased in cells treated with DQ661 relative to control. Interesting, the lysosomal/cytosolic fraction of p18 (LAMTOR1) was increased following DQ661, perhaps in a compensatory manner to recover from LMP. DQ661 could not inhibit mTORC1 in TSC2-/- mefs, suggesting that Rheb activity on the lysosomal surface is less sensitive to LMP relative to Rag/Ragulator function. The lead lysosomal inhibitor, DQ661, possessed significantly greater anti-cancer potency in a melanoma xenograft model compared to QN and the closely related DNA damaging DQ660. DQ661 also potentiated the effects of gemcitabine in a radiation/immunotherapy-resistant KPC immuno-competent syngeneic tumor model.

Dimeric quinacrines have increased potency in comparison to their chloroquine analogs, except in the case of DQ221, where potency was equal to monomeric quinacrine. The increased steric demands of the trinuclear acridine heterocycle compared to dinuclear quinoline moiety could be responsible for the limited potency of DQ221, the acridine dimer with the same linking tether as our previous reported bisaminoquinoline Lys05. In addition, the red shifted secondary fluorescence peak unique to quinacrine dimers, which we attribute to a non-radiative effect of dimeric acridines, is not found in DQ221. This lack of fluorescence in DQ221 could be due to the conformational restrictions of the bisacridine relative to the less sterically demanding Lys05. Triamines containing three to six carbon linkers were the most potent, while triamines with seven (or greater) carbon linkers resulted in dimeric quinacrines with reduced potency. The effect of alkylation of the central nitrogen of these linkers was also examined [secondary (NH) vs. tertiary (N-methyl) amines]. While cytotoxicity was similar in these pairs, off-target effects and their effects on autophagy were distinctly different. While the difference in observed activities of the secondary vs. tertiary amines cannot be due to pKa differences, that show minimal variations, the difference could be due to the possibility of secondary amine oxidation in vivo. Cell metabolism could result in the oxidation of the central secondary nitrogen, yielding a hydrolysable Schiff base. The tertiary amines would presumably require a demethylation reaction prior to the Schiff base formation, and thus the analogous reaction of the tertiary amines should be slower and less likely to occur.

Concurrent inhibition of mTOR and autophagy with a single compound is a new approach in cancer therapy. Since autophagy is one of the key resistance mechanisms to mTOR Inhibition this new class of compounds presented here has a distinct advantage over currently available rapamycin derivatives or mTOR kinase inhibitors.

TABLE 1

Lipinski Parameters

| Compd | MW | Log P | pKa | cLogP | tPSA | nROTB | Linker # |
|---|---|---|---|---|---|---|---|
| DQ 221 | 600.54 | 6.69 | 7.996 | 10.3455 | 70.48 | 10 | 7 |
| DQ 330 | 614.571 | 6.52 | 9.02 | 10.3715 | 79.27 | 12 | 9 |
| DQ 331 | 628.598 | 6.9 | 9.07 | 10.9955 | 70.48 | 12 | 9 |
| DQ 340 | 628.598 | 6.98 | 9.43 | 10.265 | 79.27 | 13 | 10 |
| DQ 341 | 642.625 | 7.35 | 9.383 | 10.8445 | 70.48 | 13 | 10 |
| DQ 440 | 642.625 | 7.43 | 9.74 | 10.1575 | 79.27 | 14 | 11 |
| DQ 441 | 656.652 | 7.81 | 9.693 | 10.6935 | 70.48 | 14 | 11 |
| DQ 550 | 670.679 | 8.27 | 10.009 | 11.2155 | 79.27 | 16 | 13 |
| DQ 551 | 684.706 | 8.64 | 9.963 | 11.7515 | 70.48 | 16 | 13 |
| DQ 660 | 698.733 | 9.1 | 10.229 | 12.2735 | 79.27 | 18 | 15 |
| DQ 661 | 712.76 | 9.48 | 10.182 | 12.8095 | 70.48 | 18 | 15 |
| DQ 770 | 726.787 | N/A | 10.241 | 13.3315 | 79.27 | 20 | 17 |
| DQ 771 | 740.814 | N/A | 10.195 | 13.8675 | 70.48 | 20 | 17 |
| DQ 880 | 754.841 | N/A | 10.293 | 14.3895 | 79.27 | 22 | 19 |
| DQ 881 | 768.868 | N/A | 10.246 | 14.9255 | 70.48 | 22 | 19 |
| DQ 11110 | 839.003 | N/A | 10.302 | 17.5635 | 79.27 | 28 | 25 |
| DQ 11111 | 853.03 | N/A | 10.256 | 18.0995 | 70.48 | 28 | 25 |

First Set of References Cited:
1. Lum J J, DeBerardinis R J, Thompson C B (2005) Autophagy in metazoans: cell survival in the land of plenty. Nat Rev Mol Cell Biol 6: 439-448.
2. Amaravadi R K, Thompson C B (2007) The roles of therapy-induced autophagy and necrosis in cancer treatment. Clin Cancer Res 13: 7271-7279.
3. Amaravadi R K, Yu D, Lum J J, Bui T, Christophorou M A, et al. (2007) Autophagy inhibition enhances therapy-induced apoptosis in a Myc-induced model of lymphoma. J Clin Invest 117: 326-336.

4. Degenhardt K, Mathew R, Beaudoin B, Bray K, Anderson D, et al. (2006) Autophagy promotes tumor cell survival and restricts necrosis, inflammation, and tumorigenesis. Cancer Cell 10: 51-64.
5. Amaravadi R K (2008) Autophagy-induced tumor dormancy in ovarian cancer. J Clin Invest.
6. Carew J S, Nawrocki S T, Kahue C N, Zhang H, Yang C, et al. (2007) Targeting autophagy augments the anticancer activity of the histone deacetylase inhibitor SAHA to overcome Bcr-Abl-mediated drug resistance. Blood.
7. Degtyarev M, De Maziere A, Orr C, Lin J, Lee B B, et al. (2008) Akt inhibition promotes autophagy and sensitizes PTEN-null tumors to lysosomotropic agents. J Cell Biol 183: 101-116.
8. Sotelo J, Briceno E, Lopez-Gonzalez M A (2006) Adding chloroquine to conventional treatment for glioblastoma multiforme: a randomized, double-blind, placebo-controlled trial. Ann Intern Med 144: 337-343.
9. Amaravadi R K, Lippincott-Schwartz J, Yin X M, Weiss W A, Takebe N, et al. (2011) Principles and Current Strategies for Targeting Autophagy for Cancer Treatment. Clin Cancer Res 17: 654-666.
10. Rebecca V W, Massaro R R, Fedorenko I V, Sondak V K, Anderson A R, et al. (2014) Inhibition of autophagy enhances the effects of the AKT inhibitor MK-2206 when combined with paclitaxel and carboplatin in BRAF wild-type melanoma. Pigment Cell Melanoma Res 27: 465-478.
11. Mahalingam D, Mita M, Sarantopoulos J, Wood L, Amaravadi R, et al. (2014) Combined autophagy and HDAC inhibition: A phase I safety, tolerability, pharmacokinetic, and pharmacodynamic analysis of hydroxychloroquine in combination with the HDAC inhibitor vorinostat in patients with advanced solid tumors. Autophagy 10.
12. Rangwala R, Chang Y C, Hu J, Algazy K, Evans T, et al. (2014) Combined MTOR and autophagy inhibition: Phase I trial of hydroxychloroquine and temsirolimus in patients with advanced solid tumors and melanoma. Autophagy 10.
13. Rangwala R, Leone R, Chang Y C, Fecher L, Schuchter L, et al. (2014) Phase I trial of hydroxychloroquine with dose-intense temozolomide in patients with advanced solid tumors and melanoma. Autophagy 10.
14. Rosenfeld M R, Ye X, Supko J G, Desideri S, Grossman S A, et al. (2014) A phase I/II trial of hydroxychloroquine in conjunction with radiation therapy and concurrent and adjuvant temozolomide in patients with newly diagnosed glioblastoma multiforme. Autophagy 10.
15. Vance D, Shah M, Joshi A, Kane R S (2008) Polyvalency: a promising strategy for drug design. Biotechnol Bioeng 101: 429-434.
16. Shrivastava A, Nunn A D, Tweedle M F (2009) Designer peptides: learning from nature. Curr Pharm Des 15: 675-681.
17. Girault S, Grellier P, Berecibar A, Maes L, Lemiere P, et al. (2001) Antiplasmodial activity and cytotoxicity of bis-, tris-, and tetraquinolines with linear or cyclic amino linkers. J Med Chem 44: 1658-1665.
18. Vennerstrom J L, Ager A L, Jr., Dorn A, Andersen S L, Gerena L, et al. (1998) Bisquinolines. 2. Antimalarial N,N-bis(7-chloroquinolin-4-yl)heteroalkanediamines. J Med Chem 41: 4360-4364.
19. Burnett J C, Schmidt J J, Stafford R G, Panchal R G, Nguyen T L, et al. (2003) Novel small molecule inhibitors of botulinum neurotoxin A metalloprotease activity. Biochem Biophys Res Commun 310: 84-93.

SECOND SET OF REFERENCES CITED

Aits, S., Kricker, J., Liu, B., Ellegaard, A. M., Hamalisto, S., Tvingsholm, S., Corcelle-Termeau, E., Hogh, S., Farkas, T., Holm Jonassen, A., et al. (2015). Sensitive detection of lysosomal membrane permeabilization by lysosomal galectin puncta assay. Autophagy 11, 1408-1424.

Bar-Peled, L., Schweitzer, L. D., Zoncu, R., and Sabatini, D. M. (2012). Ragulator is a GEF for the rag GTPases that signal amino acid levels to mTORC1. Cell 150, 1196-1208.

Carroll, B., Maetzel, D., Maddocks, O. D., Otten, G., Ratcliff, M., Smith, G. R., Dunlop, E. A., Passos, J. F., Davies, O. R., Jaenisch, R., et al. (2016). Control of TSC2-Rheb signaling axis by arginine regulates mTORC1 activity. eLife 5.

Efeyan, A., Zoncu, R., and Sabatini, D. M. (2012). Amino acids and mTORC1: from lysosomes to disease. Trends Mol Med 18, 524-533.

Egan, D. F., Chun, M. G., Vamos, M., Zou, H., Rong, J., Miller, C. J., Lou, H. J., Raveendra-Panickar, D., Yang, C. C., Sheffler, D. J., et al. (2015). Small Molecule Inhibition of the Autophagy Kinase ULK1 and Identification of ULK1 Substrates. Mol Cell 59, 285-297.

Eng, C. H., Wang, Z., Tkach, D., Toral-Barza, L., Ugwonali, S., Liu, S., Fitzgerald, S. L., George, E., Frias, E., Cochran, N., et al. (2016). Macroautophagy is dispensable for growth of KRAS mutant tumors and chloroquine efficacy. Proc Natl Acad Sci USA 113, 182-187.

Honda, A., Harrington, E., Cornella-Taracido, I., Furet, P., Knapp, M. S., Glick, M., Triantafellow, E., Dowdle, W. E., Wiedershain, D., Maniara, W., et al. (2016). Potent, Selective, and Orally Bioavailable Inhibitors of VPS34 Provide Chemical Tools to Modulate Autophagy in Vivo. ACS medicinal chemistry letters 7, 72-76.

Inoki, K., Ouyang, H., Zhu, T., Lindvall, C., Wang, Y., Zhang, X., Yang, Q., Bennett, C., Harada, Y., Stankunas, K., et al. (2006). TSC2 integrates Wnt and energy signals via a coordinated phosphorylation by AMPK and GSK3 to regulate cell growth. Cell 126, 955-968.

Jennings, B. R., and Ridler, P. J. (1983). Interaction of chromosomal stains with DNA. An electrofluorescence study. Biophysics of structure and mechanism 10, 71-79.

Jiang, X., Overholtzer, M., and Thompson, C. B. (2015). Autophagy in cellular metabolism and cancer. J Clin Invest 125, 47-54.

Kim, D. H., Sarbassov, D. D., Ali, S. M., King, J. E., Latek, R. R., Erdjument-Bromage, H., Tempst, P., and Sabatini, D. M. (2002). mTOR interacts with raptor to form a nutrient-sensitive complex that signals to the cell growth machinery. Cell 110, 163-175.

Kim, J., Kundu, M., Viollet, B., and Guan, K. L. (2011). AMPK and mTOR regulate autophagy through direct phosphorylation of Ulk1. Nature cell biology 13, 132-141.

Klionsky, D. J., and Zuckerbraun, B. (2012). Guidelines for the use and interpretation of assays for monitoring autophagy. Autophagy 8, 445-544.

Korfel, A., Schlegel, U., Herrlinger, U., Dreyling, M., Schmidt, C., von Baumgarten, L., Pezzutto, A., Grobosch, T., Kebir, S., Thiel, E., et al. (2016). Phase II Trial of Temsirolimus for Relapsed/Refractory Primary CNS Lymphoma. J Clin Oncol.

Liu, J., Xia, H., Kim, M., Xu, L., Li, Y., Zhang, L., Cai, Y., Norberg, H. V., Zhang, T., Furuya, T., et al. (2011). Beclin1 controls the levels of p53 by regulating the deubiquitination activity of USP10 and USP13. Cell 147, 223-234.

McAfee, Q., Zhang, Z., Samanta, A., Levi, S. M., Ma, X. H., Piao, S., Lynch, J. P., Uehara, T., Sepulveda, A. R., Davis, L. E., et al. (2012). Autophagy inhibitor Lys05 has single-agent antitumor activity and reproduces the phenotype of a genetic autophagy deficiency. Proc Natl Acad Sci USA 109, 8253-8258.

O'Reilly, K. E., Warycha, M., Davies, M. A., Rodrik, V., Zhou, X. K., Yee, H., Polsky, D., Pavlick, A. C., Rosen, N., Bhardwaj, N., et al. (2009). Phosphorylated 4E-BP1 is associated with poor survival in melanoma. Clinical cancer research: an official journal of the American Association for Cancer Research 15, 2872-2878.

Perera, R. M., Stoykova, S., Nicolay, B. N., Ross, K. N., Fitamant, J., Boukhali, M., Lengrand, J., Deshpande, V., Selig, M. K., Ferrone, C. R., et al. (2015). Transcriptional control of autophagy-lysosome function drives pancreatic cancer metabolism. Nature 524, 361-365.

Rangwala, R., Chang, Y. C., Hu, J., Algazy, K. M., Evans, T. L., Fecher, L. A., Schuchter, L. M., Torigian, D. A., Panosian, J. T., Troxel, A. B., et al. (2014). Combined MTOR and autophagy inhibition: phase I trial of hydroxychloroquine and temsirolimus in patients with advanced solid tumors and melanoma. Autophagy 10, 1391-1402.

Sancak, Y., Bar-Peled, L., Zoncu, R., Markhard, A. L., Nada, S., and Sabatini, D. M. (2010). Ragulator-Rag complex targets mTORC1 to the lysosomal surface and is necessary for its activation by amino acids. Cell 141, 290-303.

Twyman-Saint Victor, C., Rech, A. J., Maity, A., Rengan, R., Pauken, K. E., Stelekati, E., Benci, J. L., Xu, B., Dada, H., Odorizzi, P. M., et al. (2015). Radiation and dual checkpoint blockade activate non-redundant immune mechanisms in cancer. Nature 520, 373-377.

Vogl, D. T., Stadtmauer, E. A., Tan, K. S., Heitjan, D. F., Davis, L. E., Pontiggia, L., Rangwala, R., Piao, S., Chang, Y. C., Scott, E. C., et al. (2014). Combined autophagy and proteasome inhibition: a phase 1 trial of hydroxychloroquine and bortezomib in patients with relapsed/refractory myeloma. Autophagy 10, 1380-1390.

Wolpin, B. M., Rubinson, D. A., Wang, X., Chan, J. A., Cleary, J. M., Enzinger, P. C., Fuchs, C. S., McCleary, N. J., Meyerhardt, J. A., Ng, K., et al. (2014). Phase II and pharmacodynamic study of autophagy inhibition using hydroxychloroquine in patients with metastatic pancreatic adenocarcinoma. The oncologist 19, 637-638.

Yang, A., Rajeshkumar, N. V., Wang, X., Yabuuchi, S., Alexander, B. M., Chu, G. C., Von Hoff, D. D., Maitra, A., and Kimmelman, A. C. (2014). Autophagy is critical for pancreatic tumor growth and progression in tumors with p53 alterations. Cancer Discov 4, 905-913.

What is claimed is:

1. A compound having a chemical structure which is:

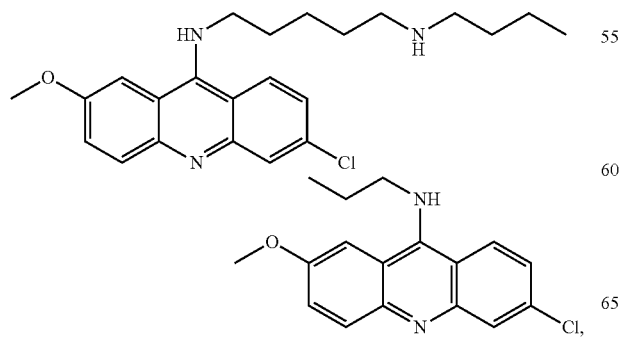

DQ550

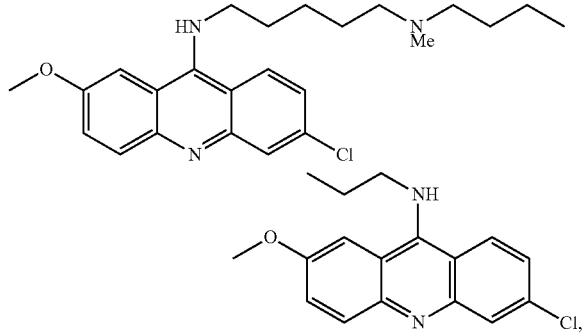

DQ551

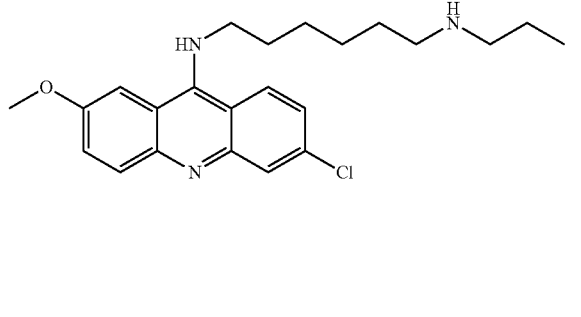

DQ660

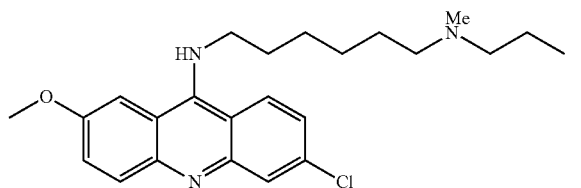

DQ661 or a pharmaceutically acceptable salt thereof.

2. A compound according to claim 1 which is:

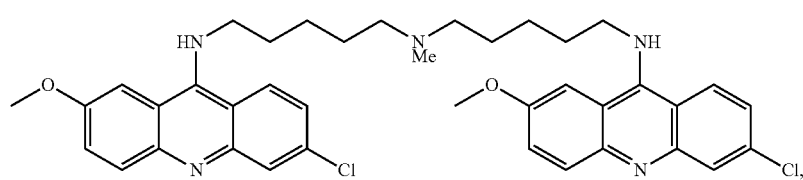

DQ551

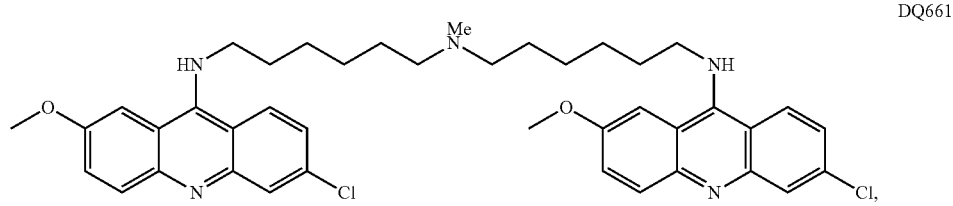 [SMILES: COc1ccc2nc3cc(Cl)ccc3c(NCCCCCCN(C)CCCCCCNc3c4ccc(Cl)cc4nc4ccc(OC)cc34)c2c1]

DQ661 a pharmaceutically acceptable salt thereof.

3. A compound according to claim 2, which is:

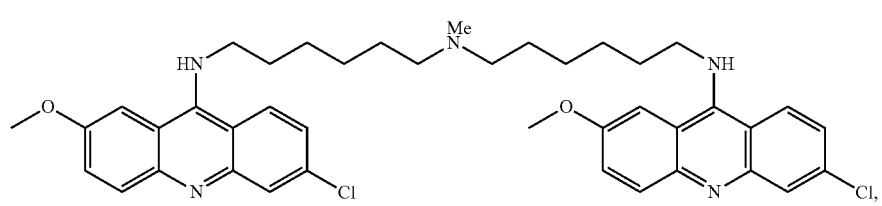

DQ661 or a pharmaceutically acceptable salt thereof.

4. A method of inhibiting autophagy in a biological system in which inhibition of autophagy is desired comprising exposing said biological system to an autophagy inhibiting effective amount of a compound according to claim 1.

* * * * *

UNITED STATES PATENT AND TRADEMARK OFFICE
CERTIFICATE OF CORRECTION

PATENT NO. : 10,774,047 B2
APPLICATION NO. : 15/567187
DATED : September 15, 2020
INVENTOR(S) : Amaravadi et al.

Page 1 of 1

It is certified that error appears in the above-identified patent and that said Letters Patent is hereby corrected as shown below:

In the Specification

In DETAILED DESCRIPTION OF THE INVENTION

Under heading Pharmaceutical Compositions, Column No. 18, Line No. 53, Replace:
"agents include the dimeric"
With:
--agents include the dimeric.--

Under heading General Reductive Alkylation Procedure, Column No. 37, Line no. 29, Replace:
"155.8, 156.5"
With:
--155.8, 156.5.--

Under heading General Reductive Alkylation Procedure, Column No. 41, Line no. 28, Replace:
"29.47, 27.77, 27.52, 27.06"
With:
--29.47, 27.77, 27.52, 27.06.--

Under heading Results, Column No. 46, Line No. 31, Replace:
"Lysosomal Surface"
With:
--Lysosomal Surface.--

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*